US009248136B2

(12) United States Patent
Bernick et al.

(10) Patent No.: US 9,248,136 B2
(45) Date of Patent: *Feb. 2, 2016

(54) TRANSDERMAL HORMONE REPLACEMENT THERAPIES

(71) Applicant: TherapeuticsMD, Inc., Boca Raton, FL (US)

(72) Inventors: Brian A. Bernick, Boca Raton, FL (US); Julia M. Amadio, Boca Raton, FL (US); Peter H. R. Persicaner, Boca Raton, FL (US); Janice Louise Cacace, Miami, FL (US); Neda Irani, Palm Beach Gardens, FL (US); Frederick D. Sancilio, Palm Beach Gardens, FL (US)

(73) Assignee: TherapeuticsMD, Inc., Boca Raton, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/125,554

(22) PCT Filed: Jan. 25, 2013

(86) PCT No.: PCT/US2013/023309
§ 371 (c)(1),
(2) Date: Dec. 12, 2013

(87) PCT Pub. No.: WO2013/112947
PCT Pub. Date: Aug. 1, 2013

(65) Prior Publication Data
US 2014/0329783 A1   Nov. 6, 2014

Related U.S. Application Data

(63) Continuation-in-part of application No. 13/684,002, filed on Nov. 21, 2012, now Pat. No. 8,633,178.

(60) Provisional application No. 61/563,408, filed on Nov. 23, 2011, provisional application No. 61/590,927, filed on Jan. 26, 2012, provisional application No. 61/661,302, filed on Jun. 18, 2012, provisional application No. 61/662,265, filed on Jun. 20, 2012.

(51) Int. Cl.
| | |
|---|---|
| A61K 31/56 | (2006.01) |
| A61K 31/57 | (2006.01) |
| A61K 9/16 | (2006.01) |
| A61K 31/565 | (2006.01) |
| A61K 9/48 | (2006.01) |
| A61K 9/70 | (2006.01) |

(52) U.S. Cl.
CPC . *A61K 31/57* (2013.01); *A61K 9/16* (2013.01); *A61K 9/4858* (2013.01); *A61K 9/7023* (2013.01); *A61K 31/565* (2013.01)

(58) Field of Classification Search
CPC ... A61K 31/565; A61K 31/57; A61K 9/0014; A61K 9/7023; A61K 9/7084

USPC .............................. 514/170, 177, 182
See application file for complete search history.

(56) References Cited

U.S. PATENT DOCUMENTS

| | | |
|---|---|---|
| 1,967,351 A | 7/1934 | Dolay |
| 2,232,438 A | 2/1941 | Butenandt |
| 2,379,832 A | 7/1945 | Serini et al. |
| 2,649,399 A | 8/1953 | Beall et al. |
| 3,198,707 A | 8/1965 | Nomine et al. |
| 3,478,070 A | 11/1969 | Stein et al. |
| 3,526,648 A | 9/1970 | Bertin et al. |
| 3,710,795 A | 1/1973 | Higuchi et al. |
| 3,729,560 A | 4/1973 | Hagerman |
| 3,729,566 A | 4/1973 | Ericsson et al. |
| 3,755,573 A | 8/1973 | Berman |
| 3,755,575 A | 8/1973 | Lerner |
| 3,903,880 A | 9/1975 | Higuchi et al. |
| 3,916,898 A | 11/1975 | Robinson |
| 3,916,899 A | 11/1975 | Theeuwes et al. |
| 3,921,636 A | 11/1975 | Zaffaroni |
| 3,923,997 A | 12/1975 | Meuly |
| 3,948,254 A | 4/1976 | Zaffaroni |
| 3,971,367 A | 7/1976 | Zaffaroni |
| 3,977,404 A | 8/1976 | Theeuwes |
| 3,993,072 A | 11/1976 | Zaffaroni |
| 4,008,719 A | 2/1977 | Theeuwes et al. |
| 4,012,496 A | 3/1977 | Schopflin et al. |
| 4,014,334 A | 3/1977 | Theeuwes et al. |
| 4,014,987 A | 3/1977 | Heller et al. |
| 4,016,251 A | 4/1977 | Higuchi et al. |
| 4,071,623 A | 1/1978 | van der Vies |

(Continued)

FOREIGN PATENT DOCUMENTS

| | | |
|---|---|---|
| BR | PI 1001367-9 A2 | 7/2012 |
| CN | 102258455 | 11/2011 |

(Continued)

OTHER PUBLICATIONS

International Search report for corresponding International Application No. PCT/US12/66406, mailed Jan. 24, 2013.
ACOG, McKinlay, et al., Practice Bulletin, Clinical Management Guidelines for Obstetrician-Gynecologists, ACOG, No. 141, Vol. 123, No. 1, Jan. 2014, Obstetrics & Gynecology.
Araya-Sibaja, Andrea M.A., Morphology Study of Progesterone Polymorphs Prepared by Polymer-Induced Heteronucleation (PIHn), Scanning vol. 35 pp. 213-221, 2013, Wiley Period., Inc.
Araya-Sibaja, Andrea Manela, et al., Polymorphism in Progesterone Selected References, SciFinder, Feb. 24, 2014, pp. 1-12, American Chem. Society & Natl. Lib. of Med.

(Continued)

*Primary Examiner* — My-Chau T Tran
(74) *Attorney, Agent, or Firm* — Kilpatrick Townsend & Stockton LLP

(57) ABSTRACT

Hormone replacement therapies are provided comprising solubilized progesterone alone and optionally with an estrogen, cyclic/sequential and continuous-combined dosing, and administered via transdermal HRT delivery systems.

20 Claims, 6 Drawing Sheets

(56) References Cited

U.S. PATENT DOCUMENTS

| | | |
|---|---|---|
| 4,093,709 A | 6/1978 | Choi et al. |
| 4,154,820 A | 5/1979 | Simoons |
| 4,155,991 A | 5/1979 | Schopflin et al. |
| 4,196,188 A | 4/1980 | Besins |
| 4,215,691 A | 8/1980 | Wong |
| 4,237,885 A | 12/1980 | Wong et al. |
| 4,310,510 A | 1/1982 | Sherman et al. |
| 4,327,725 A | 5/1982 | Cortese et al. |
| 4,372,951 A | 2/1983 | Vorys |
| 4,384,096 A | 5/1983 | Sonnabend |
| 4,393,871 A | 7/1983 | Vorhauer et al. |
| 4,402,695 A | 9/1983 | Wong |
| 4,423,151 A | 12/1983 | Baranczuk |
| 4,449,980 A | 5/1984 | Millar et al. |
| 4,610,687 A | 9/1986 | Fogwell |
| 4,629,449 A | 12/1986 | Wong |
| 4,732,763 A | 3/1988 | Beck et al. |
| 4,738,957 A | 4/1988 | Laurent et al. |
| 4,756,907 A | 7/1988 | Beck et al. |
| 4,762,717 A | 8/1988 | Crowley, Jr. |
| 4,788,062 A | 11/1988 | Gale et al. |
| 4,816,257 A | 3/1989 | Buster et al. |
| 4,822,616 A | 4/1989 | Zimmermann et al. |
| 4,865,848 A | 9/1989 | Cheng et al. |
| 4,900,734 A | 2/1990 | Maxson et al. |
| 4,906,475 A | 3/1990 | Kim |
| 4,942,158 A | 7/1990 | Sarpotdar et al. |
| 4,961,931 A | 10/1990 | Wong |
| 5,030,629 A | 7/1991 | Rajadhyaksha |
| 5,064,654 A | 11/1991 | Berner et al. |
| 5,108,995 A | 4/1992 | Casper |
| 5,128,138 A | 7/1992 | Blank |
| 5,130,137 A | 7/1992 | Crowley, Jr. |
| 5,140,021 A | 8/1992 | Maxson et al. |
| 5,211,952 A | 5/1993 | Spicer et al. |
| 5,252,334 A | 10/1993 | Chiang et al. |
| 5,280,023 A | 1/1994 | Ehrlich et al. |
| 5,288,496 A | 2/1994 | Lewis |
| 5,340,584 A | 8/1994 | Spicer et al. |
| 5,340,585 A | 8/1994 | Pike et al. |
| 5,340,586 A | 8/1994 | Pike et al. |
| 5,362,497 A | 11/1994 | Yamada et al. |
| 5,382,573 A | 1/1995 | Casper |
| 5,393,528 A | 2/1995 | Staab |
| 5,393,529 A | 2/1995 | Hoffmann et al. |
| 5,419,910 A | 5/1995 | Lewis |
| 5,468,736 A | 11/1995 | Hodgen |
| 5,474,783 A | 12/1995 | Miranda et al. |
| 5,480,776 A | 1/1996 | Dullien |
| 5,514,673 A | 5/1996 | Heckenmueller et al. |
| 5,516,528 A | 5/1996 | Hughes et al. |
| 5,527,534 A | 6/1996 | Myhling |
| 5,529,782 A | 6/1996 | Staab |
| 5,538,736 A | 7/1996 | Barth et al. |
| 5,543,150 A | 8/1996 | Bologna et al. |
| 5,547,948 A | 8/1996 | Barcomb |
| 5,556,635 A | 9/1996 | Grognet et al. |
| 5,565,199 A | 10/1996 | Page et al. |
| 5,567,831 A | 10/1996 | Li |
| 5,569,652 A | 10/1996 | Beier et al. |
| 5,580,572 A | 12/1996 | Liorzou et al. |
| 5,582,592 A | 12/1996 | Kendrick |
| 5,585,370 A | 12/1996 | Casper |
| 5,595,759 A | 1/1997 | Wright et al. |
| 5,595,970 A | 1/1997 | Garfield et al. |
| 5,605,702 A | 2/1997 | Math et al. |
| 5,607,691 A | 3/1997 | Solas et al. |
| 5,607,693 A | 3/1997 | Bonte et al. |
| 5,609,617 A | 3/1997 | Cady et al. |
| 5,620,705 A | 4/1997 | Dong et al. |
| 5,626,866 A | 5/1997 | Heiber et al. |
| 5,629,021 A | 5/1997 | Wright |
| 5,633,011 A | 5/1997 | Dong et al. |
| 5,633,242 A | 5/1997 | Oettel et al. |
| 5,639,743 A | 6/1997 | Kaswan et al. |
| 5,653,983 A | 8/1997 | Bonte et al. |
| 5,656,286 A | 8/1997 | Miranda et al. |
| 5,660,839 A | 8/1997 | Allec et al. |
| 5,662,927 A | 9/1997 | Ehrlich et al. |
| 5,663,160 A | 9/1997 | Dumas et al. |
| 5,676,968 A | 10/1997 | Lipp et al. |
| 5,677,292 A | 10/1997 | Li et al. |
| 5,686,097 A | 11/1997 | Crisologo et al. |
| 5,693,335 A | 12/1997 | Xia et al. |
| 5,694,947 A | 12/1997 | Lehtinen et al. |
| 5,700,480 A | 12/1997 | Hille et al. |
| 5,709,844 A | 1/1998 | Arbeit et al. |
| 5,719,197 A | 2/1998 | Mantelle et al. |
| 5,735,801 A | 4/1998 | Caillouette |
| 5,739,176 A | 4/1998 | Dunn et al. |
| 5,744,463 A | 4/1998 | Bair |
| 5,747,058 A | 5/1998 | Tipton et al. |
| 5,762,614 A | 6/1998 | Caillouette |
| 5,770,176 A | 6/1998 | Nargessi |
| 5,770,219 A | 6/1998 | Chiang et al. |
| 5,770,220 A | 6/1998 | Meconi et al. |
| 5,770,227 A | 6/1998 | Dong et al. |
| 5,776,495 A | 7/1998 | Duclos et al. |
| 5,780,044 A | 7/1998 | Tipton et al. |
| 5,780,050 A | 7/1998 | Jain et al. |
| 5,788,980 A | 8/1998 | Nabahi |
| 5,788,984 A | 8/1998 | Schmidt et al. |
| 5,789,442 A | 8/1998 | Garfield et al. |
| 5,811,416 A | 9/1998 | Chwalisz et al. |
| 5,811,547 A | 9/1998 | Nakamichi et al. |
| 5,814,329 A | 9/1998 | Shah |
| 5,820,878 A | 10/1998 | Shinmura et al. |
| 5,827,200 A | 10/1998 | Caillouette |
| 5,840,327 A | 11/1998 | Gale et al. |
| 5,843,468 A | 12/1998 | Yum et al. |
| 5,843,979 A | 12/1998 | Wille et al. |
| 5,858,394 A | 1/1999 | Lipp et al. |
| 5,863,552 A | 1/1999 | Yue |
| 5,866,603 A | 2/1999 | Li et al. |
| 5,882,676 A | 3/1999 | Yum et al. |
| 5,885,612 A | 3/1999 | Meconi et al. |
| 5,888,533 A | 3/1999 | Dunn |
| 5,891,462 A | 4/1999 | Carrara |
| 5,891,868 A | 4/1999 | Cummings et al. |
| 5,898,038 A | 4/1999 | Yallampalli et al. |
| 5,902,603 A | 5/1999 | Chen et al. |
| 5,904,931 A | 5/1999 | Gunther et al. |
| 5,906,830 A | 5/1999 | Farinas et al. |
| 5,912,010 A | 6/1999 | Wille et al. |
| 5,916,176 A | 6/1999 | Caillouette |
| RE36,247 E | 7/1999 | Plunkett et al. |
| 5,919,477 A | 7/1999 | Bevan et al. |
| 5,922,349 A | 7/1999 | Elliesen et al. |
| 5,928,666 A | 7/1999 | Farinas et al. |
| 5,942,243 A | 8/1999 | Shah |
| 5,942,531 A | 8/1999 | Diaz et al. |
| 5,952,000 A | 9/1999 | Fikstad et al. |
| 5,958,446 A | 9/1999 | Miranda et al. |
| 5,962,445 A | 10/1999 | Stewart |
| 5,968,919 A | 10/1999 | Gyurik et al. |
| 5,972,372 A | 10/1999 | Saleh et al. |
| 5,985,311 A | 11/1999 | Cordes et al. |
| 5,985,850 A | 11/1999 | Falk et al. |
| 5,985,861 A | 11/1999 | Levine et al. |
| 5,989,568 A | 11/1999 | De Lacharriere et al. |
| 5,993,856 A | 11/1999 | Ragavan et al. |
| 6,001,846 A | 12/1999 | Edwards et al. |
| 6,007,835 A | 12/1999 | Bon Lapillonne et al. |
| 6,010,715 A | 1/2000 | Pollock et al. |
| 6,013,276 A | 1/2000 | Teillaud et al. |
| 6,022,562 A | 2/2000 | Autant et al. |
| 6,024,974 A | 2/2000 | Li |
| 6,024,976 A | 2/2000 | Miranda et al. |
| 6,028,057 A | 2/2000 | Burns |
| 6,030,948 A | 2/2000 | Mann |
| 6,039,968 A | 3/2000 | Nabahi |
| 6,040,340 A | 3/2000 | Garfield et al. |
| 6,056,972 A | 5/2000 | Hermsmeyer |
| 6,060,077 A | 5/2000 | Meignant |

(56) References Cited

U.S. PATENT DOCUMENTS

| | | |
|---|---|---|
| 6,068,853 A | 5/2000 | Berner et al. |
| 6,074,625 A | 6/2000 | Hawthorne et al. |
| 6,077,531 A | 6/2000 | Salin-Drouin |
| 6,080,118 A | 6/2000 | Blythe |
| 6,083,178 A | 7/2000 | Caillouette |
| 6,086,916 A | 7/2000 | Agnus et al. |
| 6,087,352 A | 7/2000 | Trout |
| 6,090,404 A | 7/2000 | Meconi et al. |
| 6,096,338 A | 8/2000 | Lacy et al. |
| 6,106,848 A | 8/2000 | Wilcox et al. |
| 6,117,446 A | 9/2000 | Place |
| 6,117,450 A | 9/2000 | Dittgen et al. |
| 6,124,362 A | 9/2000 | Bradbury et al. |
| 6,133,251 A | 10/2000 | Dittgen et al. |
| 6,133,320 A | 10/2000 | Yallampalli et al. |
| 6,139,868 A | 10/2000 | Hoffmann |
| 6,139,873 A | 10/2000 | Hughes, Jr. et al. |
| 6,149,935 A | 11/2000 | Tenzel et al. |
| 6,153,216 A | 11/2000 | Cordes et al. |
| 6,165,491 A | 12/2000 | Grasset et al. |
| 6,165,975 A | 12/2000 | Adams et al. |
| 6,187,323 B1 | 2/2001 | Aiache et al. |
| 6,187,339 B1 | 2/2001 | de Haan et al. |
| 6,190,331 B1 | 2/2001 | Caillouette |
| 6,201,072 B1 | 3/2001 | Rathi et al. |
| 6,217,886 B1 | 4/2001 | Rubinstein et al. |
| 6,225,297 B1 | 5/2001 | Stockemann et al. |
| 6,227,202 B1 | 5/2001 | Matapurkar |
| 6,228,383 B1 | 5/2001 | Hansen et al. |
| 6,228,852 B1 | 5/2001 | Shaak |
| 6,242,509 B1 | 6/2001 | MacQueen et al. |
| 6,245,811 B1 | 6/2001 | Horrobin et al. |
| 6,262,115 B1 | 7/2001 | Guittard et al. |
| 6,267,984 B1 | 7/2001 | Hamlin et al. |
| 6,274,165 B1 | 8/2001 | Meconi et al. |
| 6,277,418 B1 | 8/2001 | Marakverich et al. |
| 6,283,927 B1 | 9/2001 | Caillouette |
| 6,287,588 B1 | 9/2001 | Shih et al. |
| 6,287,693 B1 | 9/2001 | Savoir et al. |
| 6,294,188 B1 | 9/2001 | Ragavan et al. |
| 6,294,192 B1 | 9/2001 | Patel et al. |
| 6,294,550 B1 | 9/2001 | Place et al. |
| 6,299,900 B1 | 10/2001 | Reed et al. |
| 6,303,132 B1 | 10/2001 | Nelson |
| 6,303,588 B1 | 10/2001 | Danielov |
| 6,306,841 B1 | 10/2001 | Place et al. |
| 6,306,914 B1 | 10/2001 | de Ziegler et al. |
| 6,309,669 B1 | 10/2001 | Setterstrom et al. |
| 6,309,848 B1 | 10/2001 | Howett et al. |
| 6,312,703 B1 | 11/2001 | Orthoefer |
| 6,328,987 B1 | 12/2001 | Marini |
| 6,342,491 B1 | 1/2002 | Dey et al. |
| 6,344,211 B1 | 2/2002 | Hille |
| 6,372,209 B1 | 4/2002 | Chrisope |
| 6,372,245 B1 | 4/2002 | Vo et al. |
| 6,372,246 B1 | 4/2002 | Wei et al. |
| 6,387,390 B1 | 5/2002 | Deaver et al. |
| 6,402,705 B1 | 6/2002 | Caillouette |
| 6,416,778 B1 | 7/2002 | Ragavan et al. |
| 6,420,352 B1 | 7/2002 | Knowles |
| 6,423,039 B1 | 7/2002 | Rathbone et al. |
| 6,423,683 B1 | 7/2002 | Heaton et al. |
| 6,432,438 B1 | 8/2002 | Shukla |
| 6,436,633 B1 | 8/2002 | Kreider et al. |
| 6,440,454 B1 | 8/2002 | Santoro et al. |
| 6,444,224 B1 | 9/2002 | Rathbone et al. |
| 6,444,234 B1 | 9/2002 | Kirby et al. |
| 6,451,300 B1 | 9/2002 | Leyba et al. |
| 6,451,339 B2 | 9/2002 | Patel et al. |
| 6,451,779 B1 | 9/2002 | Hesch |
| 6,455,246 B1 | 9/2002 | Howett et al. |
| 6,455,517 B1 | 9/2002 | Tanabe et al. |
| 6,465,004 B1 | 10/2002 | Houze et al. |
| 6,465,005 B1 | 10/2002 | Biali et al. |
| 6,465,006 B1 | 10/2002 | Zhang et al. |
| 6,468,526 B2 | 10/2002 | Chrisope |
| 6,469,016 B1 | 10/2002 | Place et al. |
| 6,472,434 B1 | 10/2002 | Place et al. |
| 6,479,232 B1 | 11/2002 | Howett et al. |
| 6,495,160 B2 | 12/2002 | Esposito et al. |
| 6,500,814 B1 | 12/2002 | Hesch |
| 6,503,896 B1 | 1/2003 | Tanabe et al. |
| 6,511,969 B1 | 1/2003 | Hermsmeyer |
| 6,521,250 B2 | 2/2003 | Seibertz et al. |
| 6,526,980 B1 | 3/2003 | Tracy et al. |
| 6,528,094 B1 | 3/2003 | Savoir et al. |
| 6,531,149 B1 | 3/2003 | Meconi et al. |
| 6,537,580 B1 | 3/2003 | Savoir et al. |
| 6,538,039 B2 | 3/2003 | Laurent |
| 6,544,196 B2 | 4/2003 | Caillouette |
| 6,544,553 B1 | 4/2003 | Hsia et al. |
| 6,548,053 B1 | 4/2003 | Murray et al. |
| 6,548,491 B2 | 4/2003 | Tanabe et al. |
| 6,551,611 B2 | 4/2003 | Elliesen et al. |
| 6,555,131 B1 | 4/2003 | Wolff et al. |
| 6,562,367 B1 | 5/2003 | Wolff et al. |
| 6,562,370 B2 | 5/2003 | Luo et al. |
| 6,562,790 B2 | 5/2003 | Chein |
| 6,569,463 B2 | 5/2003 | Patel et al. |
| 6,583,129 B1 | 6/2003 | Mazer et al. |
| 6,586,006 B2 | 7/2003 | Roser et al. |
| 6,589,549 B2 | 7/2003 | Shih et al. |
| 6,593,317 B1 | 7/2003 | de Ziegler et al. |
| 6,599,519 B1 | 7/2003 | Seo et al. |
| 6,610,652 B2 | 8/2003 | Adams et al. |
| 6,610,670 B2 | 8/2003 | Backensfeld et al. |
| 6,610,674 B1 | 8/2003 | Schreiber |
| 6,635,274 B1 | 10/2003 | Carter et al. |
| 6,638,528 B1 | 10/2003 | Kanios |
| 6,638,536 B2 | 10/2003 | Savoir et al. |
| 6,645,528 B1 | 11/2003 | Straub et al. |
| 6,649,155 B1 | 11/2003 | Dunlop et al. |
| 6,653,298 B2 | 11/2003 | Potter et al. |
| 6,656,929 B1 | 12/2003 | Agnus et al. |
| 6,660,726 B2 | 12/2003 | Hill et al. |
| 6,663,608 B2 | 12/2003 | Rathbone et al. |
| 6,663,895 B2 | 12/2003 | Savoir et al. |
| 6,682,757 B1 | 1/2004 | Wright |
| 6,692,763 B1 | 2/2004 | Cummings et al. |
| 6,708,822 B1 | 3/2004 | Muni |
| 6,720,001 B2 | 4/2004 | Chen et al. |
| 6,737,081 B2 | 5/2004 | Savoir et al. |
| 6,740,333 B2 | 5/2004 | Beckett et al. |
| 6,743,448 B2 | 6/2004 | Kryger |
| 6,743,815 B2 | 6/2004 | Huebner et al. |
| 6,747,018 B2 | 6/2004 | Tanabe et al. |
| 6,750,291 B2 | 6/2004 | Kim et al. |
| 6,756,208 B2 | 6/2004 | Griffin et al. |
| 6,776,164 B2 | 8/2004 | Bunt et al. |
| 6,787,152 B2 | 9/2004 | Kirby et al. |
| 6,805,877 B2 | 10/2004 | Massara et al. |
| 6,809,085 B1 | 10/2004 | Elson et al. |
| 6,818,226 B2 | 11/2004 | Reed et al. |
| 6,821,524 B2 | 11/2004 | Marini |
| 6,841,716 B1 | 1/2005 | Tsutsumi |
| 6,844,334 B2 | 1/2005 | Hill et al. |
| 6,855,703 B1 | 2/2005 | Hill et al. |
| 6,860,859 B2 | 3/2005 | Mehrotra et al. |
| 6,866,865 B2 | 3/2005 | Hsia et al. |
| 6,869,969 B2 | 3/2005 | Heubner et al. |
| 6,878,518 B2 | 4/2005 | Whitehead |
| 6,901,278 B1 | 5/2005 | Notelovitz |
| 6,905,705 B2 | 6/2005 | Palm et al. |
| 6,911,211 B2 | 6/2005 | Tamarkin et al. |
| 6,911,438 B2 | 6/2005 | Wright |
| 6,923,988 B2 | 8/2005 | Patel et al. |
| 6,924,274 B2 | 8/2005 | Lardy et al. |
| 6,932,983 B1 | 8/2005 | Straub et al. |
| 6,939,558 B2 | 9/2005 | Massara et al. |
| 6,943,021 B2 | 9/2005 | Klausner et al. |
| 6,958,327 B1 | 10/2005 | Hillisch et al. |
| 6,960,337 B2 | 11/2005 | Pike et al. |
| 6,962,691 B1 | 11/2005 | Lulla et al. |
| 6,962,908 B2 | 11/2005 | Aloba et al. |

(56) References Cited

U.S. PATENT DOCUMENTS

| | | |
|---|---|---|
| 6,967,194 B1 | 11/2005 | Matsuo et al. |
| 6,974,569 B2 | 12/2005 | Boyd et al. |
| 6,977,250 B2 | 12/2005 | Rodriguez |
| 6,978,945 B2 | 12/2005 | Wong et al. |
| 6,995,149 B1 | 2/2006 | Reilhac et al. |
| 7,004,321 B1 | 2/2006 | Hackbarth et al. |
| 7,005,429 B2 | 2/2006 | Dey et al. |
| 7,011,846 B2 | 3/2006 | Shojaei et al. |
| 7,018,992 B2 | 3/2006 | Koch et al. |
| 7,030,104 B2 | 4/2006 | Paris et al. |
| 7,030,157 B2 | 4/2006 | Ke et al. |
| RE39,104 E | 5/2006 | Duclos et al. |
| 7,074,779 B2 | 7/2006 | Sui et al. |
| 7,083,590 B1 | 8/2006 | Bunt et al. |
| 7,091,213 B2 | 8/2006 | Metcalf, III et al. |
| 7,094,228 B2 | 8/2006 | Zhang et al. |
| 7,097,853 B1 | 8/2006 | Keister et al. |
| 7,101,342 B1 | 9/2006 | Caillouette |
| 7,105,573 B2 | 9/2006 | Krajcik et al. |
| 7,135,190 B2 | 11/2006 | Piao et al. |
| 7,153,522 B1 | 12/2006 | Ikeura et al. |
| 7,163,681 B2 | 1/2007 | Giles-Komar et al. |
| 7,163,699 B2 | 1/2007 | Besse |
| 7,175,850 B2 | 2/2007 | Cevc |
| 7,179,799 B2 | 2/2007 | Hill et al. |
| 7,196,074 B2 | 3/2007 | Blye et al. |
| 7,198,800 B1 | 4/2007 | Ko |
| 7,198,801 B2 | 4/2007 | Carrara et al. |
| 7,226,910 B2 | 6/2007 | Wilson et al. |
| 7,247,625 B2 | 7/2007 | Zhang et al. |
| 7,250,446 B2 | 7/2007 | Sangita et al. |
| 7,267,829 B2 | 9/2007 | Kirby et al. |
| 7,300,926 B2 | 11/2007 | Prokai et al. |
| 7,303,763 B2 | 12/2007 | Ho |
| 7,317,037 B2 | 1/2008 | Fensome et al. |
| 7,329,654 B2 | 2/2008 | Kanojia et al. |
| 7,335,650 B2 | 2/2008 | Potter et al. |
| 7,374,779 B2 | 5/2008 | Chen et al. |
| 7,378,404 B2 | 5/2008 | Peters et al. |
| 7,381,427 B2 | 6/2008 | Ancira et al. |
| 7,387,789 B2 | 6/2008 | Klose et al. |
| 7,388,006 B2 | 6/2008 | Schmees et al. |
| 7,414,043 B2 | 8/2008 | Kosemund et al. |
| 7,427,413 B2 | 9/2008 | Savoir et al. |
| 7,427,609 B2 | 9/2008 | Leonard |
| 7,429,576 B2 | 9/2008 | Labrie |
| 7,431,941 B2 | 10/2008 | Besins et al. |
| 7,456,159 B2 | 11/2008 | Houze et al. |
| 7,459,445 B2 | 12/2008 | Hill et al. |
| 7,465,587 B2 | 12/2008 | Imrich |
| 7,470,433 B2 | 12/2008 | Carrara et al. |
| 7,485,666 B2 | 2/2009 | Villanueva et al. |
| 7,497,855 B2 | 3/2009 | Ausiello et al. |
| 7,498,303 B2 | 3/2009 | Arnold et al. |
| 7,534,765 B2 | 5/2009 | Gregg et al. |
| 7,534,780 B2 | 5/2009 | Ring et al. |
| 7,550,142 B2 | 6/2009 | Giles-Komar et al. |
| 7,563,565 B1 | 7/2009 | Matsuo et al. |
| 7,569,274 B2 | 8/2009 | Besse et al. |
| 7,572,779 B2 | 8/2009 | Aloba et al. |
| 7,572,780 B2 | 8/2009 | Hermsmeyer |
| 7,589,082 B2 | 9/2009 | Savoir et al. |
| 7,671,027 B2 | 3/2010 | Loumaye |
| 7,674,783 B2 | 3/2010 | Hermsmeyer |
| 7,687,281 B2 | 3/2010 | Roth et al. |
| 7,687,485 B2 | 3/2010 | Levinson et al. |
| 7,694,683 B2 | 4/2010 | Callister et al. |
| 7,704,983 B1 | 4/2010 | Hodgen et al. |
| 7,727,720 B2 | 6/2010 | Dhallan |
| 7,732,408 B2 | 6/2010 | Josephson et al. |
| 7,749,989 B2 | 7/2010 | Hill et al. |
| 7,767,656 B2 | 8/2010 | Shoichet et al. |
| 7,799,769 B2 | 9/2010 | White et al. |
| 7,815,936 B2 | 10/2010 | Hasenzahl et al. |
| 7,815,949 B2 | 10/2010 | Cohen |
| 7,829,115 B2 | 11/2010 | Besins et al. |
| 7,829,116 B2 | 11/2010 | Frye et al. |
| RE42,012 E | 12/2010 | Deaver et al. |
| 7,850,992 B2 | 12/2010 | Hwang et al. |
| 7,854,753 B2 | 12/2010 | Kraft et al. |
| 7,858,607 B2 | 12/2010 | Mamchur |
| RE42,072 E | 1/2011 | Deaver et al. |
| 7,862,552 B2 | 1/2011 | McIntyre et al. |
| 7,867,990 B2 | 1/2011 | Schultz et al. |
| 7,871,643 B2 | 1/2011 | Lizio et al. |
| 7,879,830 B2 | 2/2011 | Wiley |
| 7,884,093 B2 | 2/2011 | Creasy et al. |
| 7,925,519 B2 | 4/2011 | Greene |
| 7,939,104 B2 | 5/2011 | Barbera et al. |
| 7,943,602 B2 | 5/2011 | Bunschoten et al. |
| 7,943,604 B2 | 5/2011 | Coelingh Bennink et al. |
| 7,945,459 B2 | 5/2011 | Grace et al. |
| 7,960,368 B2 | 6/2011 | Rao et al. |
| 7,989,436 B2 | 8/2011 | Hill et al. |
| 7,989,487 B2 | 8/2011 | Welsh et al. |
| 8,022,053 B2 | 9/2011 | Mueller et al. |
| 8,048,017 B2 | 11/2011 | Xu |
| 8,048,869 B2 | 11/2011 | Bunschoten et al. |
| 8,063,030 B2 | 11/2011 | Ellman |
| 8,071,576 B2 | 12/2011 | Visser et al. |
| 8,071,729 B2 | 12/2011 | Giles-Komar et al. |
| 8,075,916 B2 | 12/2011 | Park et al. |
| 8,075,917 B2 | 12/2011 | Park et al. |
| 8,076,317 B2 | 12/2011 | Kulmann |
| 8,076,319 B2 | 12/2011 | Leonard |
| 8,080,553 B2 | 12/2011 | Auspitz et al. |
| 8,088,605 B2 | 1/2012 | Beaudet et al. |
| 8,096,940 B2 | 1/2012 | Iverson et al. |
| 8,101,209 B2 | 1/2012 | Legrand et al. |
| 8,101,773 B2 | 1/2012 | Smith et al. |
| 8,114,152 B2 | 2/2012 | Furst |
| 8,114,434 B2 | 2/2012 | Sasaki et al. |
| 8,114,442 B2 | 2/2012 | Tucker et al. |
| 8,119,741 B2 | 2/2012 | Pavlin |
| 8,121,886 B2 | 2/2012 | Azar |
| 8,124,118 B2 | 2/2012 | Lennernaes et al. |
| 8,124,595 B2 | 2/2012 | Boissonneault |
| 8,147,561 B2 | 4/2012 | Binmoeller |
| 8,148,546 B2 | 4/2012 | Baasner et al. |
| 8,158,613 B2 | 4/2012 | Staniforth et al. |
| 8,158,614 B2 | 4/2012 | Lambert et al. |
| 8,163,722 B2 | 4/2012 | Savoir et al. |
| 8,177,449 B2 | 5/2012 | Watkinson et al. |
| 8,182,833 B2 | 5/2012 | Hermsmeyer |
| 8,187,615 B2 | 5/2012 | Friedman |
| 8,187,640 B2 | 5/2012 | Dunn |
| 8,195,403 B2 | 6/2012 | Wood, Jr. et al. |
| 8,202,736 B2 | 6/2012 | Mousa et al. |
| 8,217,024 B2 | 7/2012 | Ahmed et al. |
| 8,221,785 B2 | 7/2012 | Chien |
| 8,222,008 B2 | 7/2012 | Thoene |
| 8,222,237 B2 | 7/2012 | Narkunan et al. |
| 8,227,454 B2 | 7/2012 | Hill et al. |
| 8,227,509 B2 | 7/2012 | Castro et al. |
| 8,241,664 B2 | 8/2012 | Dudley et al. |
| 8,247,393 B2 | 8/2012 | Ahmed et al. |
| 8,257,724 B2 | 9/2012 | Cromack et al. |
| 8,257,725 B2 | 9/2012 | Cromack et al. |
| 8,268,352 B2 | 9/2012 | Karan et al. |
| 8,268,806 B2 | 9/2012 | Labrie |
| 8,268,878 B2 | 9/2012 | Johnson et al. |
| 8,273,730 B2 | 9/2012 | Fernandez et al. |
| 8,287,888 B2 | 10/2012 | Song et al. |
| 8,288,366 B2 | 10/2012 | Gonzalez et al. |
| 8,318,898 B2 | 11/2012 | Fasel et al. |
| 8,324,193 B2 | 12/2012 | Lee Sepsick et al. |
| 8,329,680 B2 | 12/2012 | Evans et al. |
| 8,337,814 B2 | 12/2012 | Osbakken et al. |
| 8,344,007 B2 | 1/2013 | Chui et al. |
| 8,349,820 B2 | 1/2013 | Zeun et al. |
| 8,353,863 B2 | 1/2013 | Imran |
| 8,357,723 B2 | 1/2013 | Satyam |
| 8,361,995 B2 | 1/2013 | Schramm |
| 8,362,091 B2 | 1/2013 | Besonov et al. |

(56) References Cited

U.S. PATENT DOCUMENTS

| | | | |
|---|---|---|---|
| 8,372,424 B2 | 2/2013 | Berry et al. |
| 8,372,806 B2 | 2/2013 | Bragagna et al. |
| 8,377,482 B2 | 2/2013 | Laurie et al. |
| 8,377,994 B2 | 2/2013 | Drechsler et al. |
| 8,394,759 B2 | 3/2013 | Barathur et al. |
| 8,415,332 B2 | 4/2013 | Reape et al. |
| 8,420,111 B2 | 4/2013 | Hermsmeyer |
| 8,435,561 B2 | 5/2013 | Besins et al. |
| 8,435,972 B2 | 5/2013 | Sayeed et al. |
| 8,449,879 B2 | 5/2013 | Laurent Applegate et al. |
| 8,450,108 B2 | 5/2013 | Boyce |
| 8,454,945 B2 | 6/2013 | Narain et al. |
| 8,455,468 B2 | 6/2013 | Kellermann et al. |
| 8,461,138 B2 | 6/2013 | Boissonneault |
| 8,476,252 B2 | 7/2013 | Pickersgill et al. |
| 8,481,488 B2 | 7/2013 | Carter |
| 8,486,374 B2 | 7/2013 | Zlatkis et al. |
| 8,486,442 B2 | 7/2013 | Yamaji et al. |
| 8,492,368 B2 | 7/2013 | Lewandowski et al. |
| 8,507,467 B2 | 8/2013 | Ueda et al. |
| 8,512,693 B2 | 8/2013 | Azevedo et al. |
| 8,512,754 B2 | 8/2013 | Needham |
| 8,518,376 B2 | 8/2013 | Schuz et al. |
| 8,536,159 B2 | 9/2013 | Zeng et al. |
| 8,540,967 B2 | 9/2013 | Trivedi et al. |
| 8,541,400 B2 | 9/2013 | Joabsson et al. |
| 8,551,462 B2 | 10/2013 | Marenus et al. |
| 8,557,281 B2 | 10/2013 | Tuominen et al. |
| 8,568,374 B2 | 10/2013 | De Graaff et al. |
| 8,591,951 B2 | 11/2013 | Kohn et al. |
| 8,613,951 B2 | 12/2013 | Troiano et al. |
| 8,633,178 B2 * | 1/2014 | Bernick et al. ............... 514/169 |
| 8,633,180 B2 | 1/2014 | Zeng et al. |
| 8,636,787 B2 | 1/2014 | Sabaria |
| 8,636,982 B2 | 1/2014 | Schuz et al. |
| 8,653,129 B2 | 2/2014 | Fein et al. |
| 8,658,627 B2 | 2/2014 | Voskuhl |
| 8,658,628 B2 | 2/2014 | Baucom |
| 8,663,681 B2 | 3/2014 | Ahmed et al. |
| 8,663,692 B1 | 3/2014 | Mueller et al. |
| 8,663,703 B2 | 3/2014 | Moldavski et al. |
| 8,664,207 B2 | 3/2014 | Zheng et al. |
| 8,669,293 B2 | 3/2014 | Sharoni et al. |
| 8,679,552 B2 | 3/2014 | Guthery |
| 8,694,358 B2 | 4/2014 | Tryfon |
| 8,697,127 B2 | 4/2014 | Sah |
| 8,697,710 B2 | 4/2014 | Zeng |
| 8,703,105 B2 | 4/2014 | Besonov et al. |
| 8,709,385 B2 | 4/2014 | Schuz et al. |
| 8,709,451 B2 | 4/2014 | Rapoport et al. |
| 8,715,735 B2 | 5/2014 | Funke et al. |
| 8,721,331 B2 | 5/2014 | Raghuprasad |
| 8,722,021 B2 | 5/2014 | Eini et al. |
| 8,734,846 B2 | 5/2014 | Hrkach et al. |
| 8,735,381 B2 | 5/2014 | Podolski |
| 8,741,336 B2 | 6/2014 | Dipierro et al. |
| 8,741,373 B2 | 6/2014 | Rao et al. |
| 8,753,661 B2 | 6/2014 | Gassner et al. |
| 8,784,882 B2 | 7/2014 | Mattern |
| 8,846,648 B2 * | 9/2014 | Bernick et al. ............... 514/169 |
| 8,846,649 B2 * | 9/2014 | Bernick et al. ............... 514/169 |
| 8,933,059 B2 * | 1/2015 | Bernick et al. ............... 514/169 |
| 8,987,237 B2 * | 3/2015 | Bernick et al. ............... 514/169 |
| 8,987,238 B2 * | 3/2015 | Bernick et al. ............... 514/169 |
| 8,993,548 B2 * | 3/2015 | Bernick et al. ............... 514/169 |
| 8,993,549 B2 * | 3/2015 | Bernick et al. ............... 514/169 |
| 9,006,222 B2 * | 4/2015 | Bernick et al. ............... 514/169 |
| 9,012,434 B2 * | 4/2015 | Bernick et al. ............... 514/169 |
| 2001/0005728 A1 | 6/2001 | Guittard et al. |
| 2001/0009673 A1 | 7/2001 | Gunther et al. |
| 2001/0021816 A1 | 9/2001 | Caillouette |
| 2001/0023261 A1 | 9/2001 | Ryoo et al. |
| 2001/0027189 A1 | 10/2001 | Bennink et al. |
| 2001/0029357 A1 | 10/2001 | Bunt et al. |
| 2001/0031747 A1 | 10/2001 | deZiegler et al. |
| 2001/0032125 A1 | 10/2001 | Bhan et al. |
| 2001/0034340 A1 | 10/2001 | Pickar |
| 2001/0053383 A1 | 12/2001 | Sablotsky et al. |
| 2001/0056068 A1 | 12/2001 | Chwalisz et al. |
| 2002/0012710 A1 | 1/2002 | Lansky |
| 2002/0026158 A1 | 2/2002 | Rathbone et al. |
| 2002/0028788 A1 | 3/2002 | Bunt et al. |
| 2002/0035070 A1 | 3/2002 | Gardlik et al. |
| 2002/0058648 A1 | 5/2002 | Hammerly |
| 2002/0058926 A1 | 5/2002 | Rathbone et al. |
| 2002/0064541 A1 | 5/2002 | Lapidot et al. |
| 2002/0076441 A1 | 6/2002 | Shih et al. |
| 2002/0102308 A1 | 8/2002 | Wei et al. |
| 2002/0107230 A1 | 8/2002 | Waldon et al. |
| 2002/0114803 A1 | 8/2002 | Deaver et al. |
| 2002/0119174 A1 | 8/2002 | Gardlik et al. |
| 2002/0119198 A1 | 8/2002 | Gao et al. |
| 2002/0132801 A1 | 9/2002 | Heil et al. |
| 2002/0137749 A1 | 9/2002 | Levinson et al. |
| 2002/0142017 A1 | 10/2002 | Simonnet |
| 2002/0151530 A1 | 10/2002 | Leonard et al. |
| 2002/0156394 A1 | 10/2002 | Mehrotra et al. |
| 2002/0169150 A1 | 11/2002 | Pickar |
| 2002/0169205 A1 | 11/2002 | Garfield et al. |
| 2002/0173510 A1 | 11/2002 | Levinson et al. |
| 2002/0193356 A1 | 12/2002 | Van Beek et al. |
| 2002/0193758 A1 | 12/2002 | Sandberg |
| 2002/0197286 A1 | 12/2002 | Brandman et al. |
| 2003/0003139 A1 | 1/2003 | Gunther et al. |
| 2003/0004145 A1 | 1/2003 | Leonard |
| 2003/0007994 A1 | 1/2003 | Bunt et al. |
| 2003/0027772 A1 | 2/2003 | Breton |
| 2003/0044453 A1 | 3/2003 | Volkel et al. |
| 2003/0049307 A1 | 3/2003 | Gyurik |
| 2003/0064097 A1 | 4/2003 | Patel et al. |
| 2003/0072760 A1 | 4/2003 | Sirbasku |
| 2003/0073248 A1 | 4/2003 | Roth et al. |
| 2003/0073673 A1 | 4/2003 | Hesch |
| 2003/0077297 A1 | 4/2003 | Chen et al. |
| 2003/0078245 A1 | 4/2003 | Bennink et al. |
| 2003/0091620 A1 | 5/2003 | Venkateshwaran et al. |
| 2003/0091640 A1 | 5/2003 | Ramanathan et al. |
| 2003/0092691 A1 | 5/2003 | Besse et al. |
| 2003/0096012 A1 | 5/2003 | Besse et al. |
| 2003/0104048 A1 | 6/2003 | Patel et al. |
| 2003/0109507 A1 | 6/2003 | Beckmann et al. |
| 2003/0113268 A1 | 6/2003 | Buenafae et al. |
| 2003/0114420 A1 | 6/2003 | Salvati et al. |
| 2003/0114430 A1 | 6/2003 | MacLeod et al. |
| 2003/0124182 A1 | 7/2003 | Shojaei et al. |
| 2003/0124191 A1 | 7/2003 | Besse et al. |
| 2003/0130558 A1 | 7/2003 | Massara et al. |
| 2003/0144258 A1 | 7/2003 | Heil et al. |
| 2003/0157157 A1 | 8/2003 | Luo et al. |
| 2003/0166509 A1 | 9/2003 | Edwards et al. |
| 2003/0170295 A1 | 9/2003 | Yoon et al. |
| 2003/0175329 A1 | 9/2003 | Mak et al. |
| 2003/0175333 A1 | 9/2003 | Shefer et al. |
| 2003/0180352 A1 | 9/2003 | Patel et al. |
| 2003/0181353 A1 | 9/2003 | Nyce |
| 2003/0181728 A1 | 9/2003 | Salvati et al. |
| 2003/0191096 A1 | 10/2003 | Leonard et al. |
| 2003/0195177 A1 | 10/2003 | Leonard et al. |
| 2003/0215496 A1 | 11/2003 | Patel et al. |
| 2003/0219402 A1 | 11/2003 | Rutter |
| 2003/0220297 A1 | 11/2003 | Berstein et al. |
| 2003/0224057 A1 | 12/2003 | Martin-Letellier et al. |
| 2003/0224059 A1 | 12/2003 | Lerner et al. |
| 2003/0225047 A1 | 12/2003 | Friedman et al. |
| 2003/0225048 A1 | 12/2003 | Friedman et al. |
| 2003/0225050 A1 | 12/2003 | Eichardt et al. |
| 2003/0228686 A1 | 12/2003 | Klausner et al. |
| 2003/0229057 A1 | 12/2003 | Caubel et al. |
| 2003/0235596 A1 | 12/2003 | Gao et al. |
| 2003/0236236 A1 | 12/2003 | Chen et al. |
| 2004/0009960 A1 | 1/2004 | Heil et al. |
| 2004/0022820 A1 | 2/2004 | Anderson |
| 2004/0034001 A1 | 2/2004 | Karara |
| 2004/0037881 A1 | 2/2004 | Guittard et al. |

(56) References Cited

U.S. PATENT DOCUMENTS

| | | |
|---|---|---|
| 2004/0039356 A1 | 2/2004 | Maki et al. |
| 2004/0043043 A1 | 3/2004 | Schlyter et al. |
| 2004/0043943 A1 | 3/2004 | Guittard et al. |
| 2004/0044080 A1 | 3/2004 | Place et al. |
| 2004/0048900 A1 | 3/2004 | Flood |
| 2004/0052824 A1 | 3/2004 | Abou Chacra-Vernet et al. |
| 2004/0073024 A1 | 4/2004 | Metcalf, III et al. |
| 2004/0077605 A1 | 4/2004 | Salvati et al. |
| 2004/0077606 A1 | 4/2004 | Salvati et al. |
| 2004/0087548 A1 | 5/2004 | Salvati et al. |
| 2004/0087564 A1 | 5/2004 | Wright et al. |
| 2004/0089308 A1 | 5/2004 | Welch |
| 2004/0092494 A9 | 5/2004 | Dudley |
| 2004/0092583 A1 | 5/2004 | Shanahan-Prendergast |
| 2004/0093261 A1 | 5/2004 | Jain et al. |
| 2004/0097468 A1 | 5/2004 | Wimalawansa |
| 2004/0101557 A1 | 5/2004 | Gibson et al. |
| 2004/0106542 A1 | 6/2004 | Deaver et al. |
| 2004/0110732 A1 | 6/2004 | Masini Eteve et al. |
| 2004/0131670 A1 | 7/2004 | Gao |
| 2004/0138103 A1 | 7/2004 | Patt |
| 2004/0142012 A1 | 7/2004 | Bunt et al. |
| 2004/0146539 A1 | 7/2004 | Gupta |
| 2004/0146894 A1 | 7/2004 | Warrington et al. |
| 2004/0161435 A1 | 8/2004 | Gupta |
| 2004/0176324 A1 | 9/2004 | Salvati et al. |
| 2004/0176336 A1 | 9/2004 | Rodriguez |
| 2004/0185104 A1 | 9/2004 | Piao et al. |
| 2004/0191207 A1 | 9/2004 | Lipari et al. |
| 2004/0191276 A1 | 9/2004 | Muni |
| 2004/0198706 A1 | 10/2004 | Carrara et al. |
| 2004/0210280 A1 | 10/2004 | Liedtke |
| 2004/0213744 A1 | 10/2004 | Lulla et al. |
| 2004/0219124 A1 | 11/2004 | Gupta |
| 2004/0225140 A1 | 11/2004 | Sciano et al. |
| 2004/0234606 A1 | 11/2004 | Levine et al. |
| 2004/0241219 A1 | 12/2004 | Hille et al. |
| 2004/0243437 A1 | 12/2004 | Grace et al. |
| 2004/0253319 A1 | 12/2004 | Netke et al. |
| 2004/0259817 A1 | 12/2004 | Waldon et al. |
| 2004/0266745 A1 | 12/2004 | Schwanitz et al. |
| 2005/0003003 A1 | 1/2005 | Deaver et al. |
| 2005/0004088 A1 | 1/2005 | Hesch |
| 2005/0009800 A1 | 1/2005 | Thumbeck et al. |
| 2005/0014729 A1 | 1/2005 | Pulaski |
| 2005/0020550 A1 | 1/2005 | Latif et al. |
| 2005/0020552 A1 | 1/2005 | Aschkenasay et al. |
| 2005/0021009 A1 | 1/2005 | Massara et al. |
| 2005/0025833 A1 | 2/2005 | Aschkenasay et al. |
| 2005/0031651 A1 | 2/2005 | Gervais et al. |
| 2005/0042173 A1 | 2/2005 | Besse et al. |
| 2005/0042268 A1 | 2/2005 | Aschkenasay et al. |
| 2005/0048116 A1 | 3/2005 | Straub et al. |
| 2005/0054991 A1 | 3/2005 | Paterson et al. |
| 2005/0079138 A1 | 4/2005 | Chickering, III et al. |
| 2005/0085453 A1 | 4/2005 | Govindarajan |
| 2005/0101579 A1 | 5/2005 | Shippen |
| 2005/0113350 A1 | 5/2005 | Duesterberg et al. |
| 2005/0118244 A1 | 6/2005 | Theobald et al. |
| 2005/0118272 A1 | 6/2005 | Besse et al. |
| 2005/0129756 A1 | 6/2005 | Podhaisky et al. |
| 2005/0152956 A1 | 7/2005 | Dudley |
| 2005/0153946 A1 | 7/2005 | Hirsh et al. |
| 2005/0164977 A1 | 7/2005 | Coelingh Bennink |
| 2005/0182105 A1 | 8/2005 | Nirschl et al. |
| 2005/0186141 A1 | 8/2005 | Gonda et al. |
| 2005/0187267 A1 | 8/2005 | Hamann et al. |
| 2005/0192253 A1 | 9/2005 | Salvati et al. |
| 2005/0192310 A1 | 9/2005 | Gavai et al. |
| 2005/0196434 A1 | 9/2005 | Brierre |
| 2005/0207990 A1 | 9/2005 | Funke et al. |
| 2005/0214384 A1 | 9/2005 | Juturu et al. |
| 2005/0220825 A1 | 10/2005 | Funke et al. |
| 2005/0220900 A1 | 10/2005 | Wuttke et al. |
| 2005/0222106 A1 | 10/2005 | Bracht |
| 2005/0228692 A1 | 10/2005 | Hodgdon |
| 2005/0228718 A1 | 10/2005 | Austin |
| 2005/0239747 A1 | 10/2005 | Le et al. |
| 2005/0239758 A1 | 10/2005 | Roby |
| 2005/0244360 A1 | 11/2005 | Billoni |
| 2005/0244522 A1 | 11/2005 | Carrara et al. |
| 2005/0245902 A1 | 11/2005 | Cornish et al. |
| 2005/0250746 A1 | 11/2005 | Iammatteo |
| 2005/0250750 A1 | 11/2005 | Cummings et al. |
| 2005/0250753 A1 | 11/2005 | Fink et al. |
| 2005/0256028 A1 | 11/2005 | Yun et al. |
| 2005/0266078 A1 | 12/2005 | Jorda et al. |
| 2005/0266088 A1 | 12/2005 | Frijlink et al. |
| 2005/0271597 A1 | 12/2005 | Keith |
| 2005/0271598 A1 | 12/2005 | Friedman et al. |
| 2005/0272685 A1 | 12/2005 | Hung |
| 2005/0272712 A1 | 12/2005 | Grubb et al. |
| 2006/0009428 A1 | 1/2006 | Grubb et al. |
| 2006/0014728 A1 | 1/2006 | Chwalisz et al. |
| 2006/0018937 A1 | 1/2006 | Friedman et al. |
| 2006/0019978 A1 | 1/2006 | Balog |
| 2006/0020002 A1 | 1/2006 | Salvati et al. |
| 2006/0030615 A1 | 2/2006 | Fensome et al. |
| 2006/0034889 A1 | 2/2006 | Jo et al. |
| 2006/0034904 A1 | 2/2006 | Weimann |
| 2006/0040904 A1 | 2/2006 | Ahmed et al. |
| 2006/0051391 A1 | 3/2006 | Dvoskin et al. |
| 2006/0052341 A1 | 3/2006 | Cornish et al. |
| 2006/0069031 A1 | 3/2006 | Loumaye |
| 2006/0078618 A1 | 4/2006 | Constantinides et al. |
| 2006/0083778 A1 | 4/2006 | Allison et al. |
| 2006/0084704 A1 | 4/2006 | Shih et al. |
| 2006/0088580 A1 | 4/2006 | Seibertz et al. |
| 2006/0089337 A1 | 4/2006 | Casper et al. |
| 2006/0093678 A1 | 5/2006 | Chickering, III et al. |
| 2006/0100180 A1 | 5/2006 | Bohlmann et al. |
| 2006/0106004 A1 | 5/2006 | Brody et al. |
| 2006/0110415 A1 | 5/2006 | Gupta |
| 2006/0111424 A1 | 5/2006 | Salvati et al. |
| 2006/0121102 A1 | 6/2006 | Chiang |
| 2006/0121626 A1 | 6/2006 | Imrich |
| 2006/0134188 A1 | 6/2006 | Podhaisky et al. |
| 2006/0135619 A1 | 6/2006 | Kick et al. |
| 2006/0165744 A1 | 7/2006 | Anyarambhatla et al. |
| 2006/0193789 A1 | 8/2006 | Tamarkin et al. |
| 2006/0194775 A1 | 8/2006 | Tofovic et al. |
| 2006/0204557 A1 | 9/2006 | Gupta et al. |
| 2006/0233743 A1 | 10/2006 | Kelly |
| 2006/0233841 A1 | 10/2006 | Pushpala et al. |
| 2006/0235037 A1 | 10/2006 | Purandare et al. |
| 2006/0240111 A1 | 10/2006 | Fernandez et al. |
| 2006/0246122 A1 | 11/2006 | Langguth et al. |
| 2006/0247216 A1 | 11/2006 | Haj-Yehia |
| 2006/0247221 A1 | 11/2006 | Coelingh Bennink et al. |
| 2006/0251581 A1 | 11/2006 | Madenjian et al. |
| 2006/0252049 A1 | 11/2006 | Shuler et al. |
| 2006/0257472 A1 | 11/2006 | Nielsen |
| 2006/0275218 A1 | 12/2006 | Besonov et al. |
| 2006/0275360 A1 | 12/2006 | Ahmed et al. |
| 2006/0276414 A1 | 12/2006 | Coelingh Bennink et al. |
| 2006/0280771 A1 | 12/2006 | Groenewegen et al. |
| 2006/0280797 A1 | 12/2006 | Shoichet et al. |
| 2006/0280800 A1 | 12/2006 | Nagi et al. |
| 2006/0292223 A1 | 12/2006 | Mc Ilroy et al. |
| 2007/0004693 A1 | 1/2007 | Woolfson et al. |
| 2007/0004694 A1 | 1/2007 | Woolfson et al. |
| 2007/0009559 A1 | 1/2007 | Alosio et al. |
| 2007/0009594 A1 | 1/2007 | Grubb et al. |
| 2007/0010550 A1 | 1/2007 | McKenzie |
| 2007/0014839 A1 | 1/2007 | Bracht |
| 2007/0015698 A1 | 1/2007 | Goldstein et al. |
| 2007/0021360 A1 | 1/2007 | Nyce et al. |
| 2007/0027201 A1 | 2/2007 | McComas et al. |
| 2007/0031491 A1 | 2/2007 | Levine et al. |
| 2007/0037780 A1 | 2/2007 | Anigbogu et al. |
| 2007/0037782 A1 | 2/2007 | Suzuki et al. |
| 2007/0042038 A1 | 2/2007 | Besse |
| 2007/0060589 A1 | 3/2007 | Purandare et al. |
| 2007/0066628 A1 | 3/2007 | Zhang et al. |

(56) References Cited

U.S. PATENT DOCUMENTS

| | | |
|---|---|---|
| 2007/0066637 A1 | 3/2007 | Zhang et al. |
| 2007/0066675 A1 | 3/2007 | Zhang et al. |
| 2007/0078091 A1 | 4/2007 | Hubler et al. |
| 2007/0088029 A1 | 4/2007 | Balog et al. |
| 2007/0093548 A1 | 4/2007 | Diffendal et al. |
| 2007/0116729 A1 | 5/2007 | Palepu |
| 2007/0116829 A1 | 5/2007 | Prakash et al. |
| 2007/0128263 A1 | 6/2007 | Wall et al. |
| 2007/0154533 A1 | 7/2007 | Dudley |
| 2007/0167418 A1 | 7/2007 | Ferguson |
| 2007/0178166 A1 | 8/2007 | Bernstein et al. |
| 2007/0184558 A1 | 8/2007 | Roth et al. |
| 2007/0185068 A1 | 8/2007 | Ferguson et al. |
| 2007/0190022 A1 | 8/2007 | Chiao et al. |
| 2007/0191319 A1 | 8/2007 | Ke et al. |
| 2007/0196415 A1 | 8/2007 | Houston et al. |
| 2007/0196433 A1 | 8/2007 | Ron et al. |
| 2007/0207225 A1 | 9/2007 | Squadrito |
| 2007/0225281 A1 | 9/2007 | Zhang et al. |
| 2007/0232574 A1 | 10/2007 | Bernard et al. |
| 2007/0238713 A1 | 10/2007 | Gast et al. |
| 2007/0243229 A1 | 10/2007 | Smith et al. |
| 2007/0248658 A1 | 10/2007 | Bracht et al. |
| 2007/0254858 A1 | 11/2007 | Cronk |
| 2007/0255197 A1 | 11/2007 | Wilkins et al. |
| 2007/0264309 A1 | 11/2007 | Chollet et al. |
| 2007/0264345 A1 | 11/2007 | Eros et al. |
| 2007/0264349 A1 | 11/2007 | Lee et al. |
| 2007/0286819 A1 | 12/2007 | DeVries et al. |
| 2007/0287688 A1 | 12/2007 | Chan et al. |
| 2007/0287789 A1 | 12/2007 | Jones et al. |
| 2007/0292359 A1 | 12/2007 | Schuz et al. |
| 2007/0292387 A1 | 12/2007 | Jon et al. |
| 2007/0292461 A1 | 12/2007 | Danziger et al. |
| 2007/0292493 A1 | 12/2007 | Brierre |
| 2007/0298089 A1 | 12/2007 | Yoshinaga et al. |
| 2008/0026035 A1 | 1/2008 | Chollet et al. |
| 2008/0026040 A1 | 1/2008 | Rivera et al. |
| 2008/0026062 A1 | 1/2008 | Farr et al. |
| 2008/0038219 A1 | 2/2008 | Carlson et al. |
| 2008/0038350 A1 | 2/2008 | Gerecke et al. |
| 2008/0039405 A1 | 2/2008 | Joseph et al. |
| 2008/0050317 A1 | 2/2008 | Besonov et al. |
| 2008/0051351 A1 | 2/2008 | Ghisalberti |
| 2008/0063607 A1 | 3/2008 | Berman et al. |
| 2008/0069779 A1 | 3/2008 | Schuz et al. |
| 2008/0069791 A1 | 3/2008 | Beissert |
| 2008/0085877 A1 | 4/2008 | Bortz |
| 2008/0095831 A1 | 4/2008 | Mc Graw |
| 2008/0095838 A1 | 4/2008 | Abou Chacra-Vernet |
| 2008/0113953 A1 | 5/2008 | De Vries et al. |
| 2008/0114050 A1 | 5/2008 | Fensome et al. |
| 2008/0119537 A1 | 5/2008 | Zhang et al. |
| 2008/0125402 A1 | 5/2008 | Dilberti |
| 2008/0138379 A1 | 6/2008 | Jennings-Spring |
| 2008/0138390 A1 | 6/2008 | Gricenko et al. |
| 2008/0139392 A1 | 6/2008 | Yuan et al. |
| 2008/0145423 A1 | 6/2008 | Khan et al. |
| 2008/0153789 A1 | 6/2008 | Dmowski et al. |
| 2008/0175814 A1 | 7/2008 | Phiasivongsa et al. |
| 2008/0175905 A1 | 7/2008 | Baksh et al. |
| 2008/0175908 A1 | 7/2008 | Baksh et al. |
| 2008/0188829 A1 | 8/2008 | Creasy |
| 2008/0206156 A1 | 8/2008 | Cronk |
| 2008/0206159 A1 | 8/2008 | Schuz et al. |
| 2008/0206161 A1 | 8/2008 | Tamarkin et al. |
| 2008/0214512 A1 | 9/2008 | Seitz et al. |
| 2008/0220069 A1 | 9/2008 | Allison |
| 2008/0226698 A1 | 9/2008 | Beste et al. |
| 2008/0227763 A1 | 9/2008 | Paris et al. |
| 2008/0234199 A1 | 9/2008 | Katamreddy |
| 2008/0234240 A1 | 9/2008 | Duesterberg et al. |
| 2008/0255078 A1 | 10/2008 | Katamreddy |
| 2008/0255089 A1 | 10/2008 | Katamreddy |
| 2008/0261931 A1 | 10/2008 | Stenlof et al. |
| 2008/0299220 A1 | 12/2008 | Tamarkin et al. |
| 2008/0306036 A1 | 12/2008 | Katamreddy |
| 2008/0312197 A1 | 12/2008 | Rodriguez |
| 2008/0312198 A1 | 12/2008 | Rodriguez |
| 2008/0319078 A1 | 12/2008 | Katamreddy |
| 2009/0004246 A1 | 1/2009 | Woolfson et al. |
| 2009/0010968 A1 | 1/2009 | Peyrot et al. |
| 2009/0011041 A1 | 1/2009 | Musaeva et al. |
| 2009/0017120 A1 | 1/2009 | Brisco et al. |
| 2009/0022683 A1 | 1/2009 | Park et al. |
| 2009/0047357 A1 | 2/2009 | Tomohira et al. |
| 2009/0053294 A1 | 2/2009 | Prendergast |
| 2009/0060982 A1 | 3/2009 | Ron et al. |
| 2009/0060997 A1 | 3/2009 | Seitz et al. |
| 2009/0068118 A1 | 3/2009 | Eini et al. |
| 2009/0081206 A1 | 3/2009 | Leibovitz |
| 2009/0081278 A1 | 3/2009 | De Graaff et al. |
| 2009/0081303 A1 | 3/2009 | Savoir et al. |
| 2009/0092656 A1 | 4/2009 | Klamerus et al. |
| 2009/0093440 A1 | 4/2009 | Murad |
| 2009/0098069 A1 | 4/2009 | Vacca |
| 2009/0099106 A1 | 4/2009 | Phiasivongsa et al. |
| 2009/0099149 A1 | 4/2009 | Kresevic et al. |
| 2009/0130029 A1 | 5/2009 | Tamarkin et al. |
| 2009/0131385 A1 | 5/2009 | Voskuhl |
| 2009/0137478 A1 | 5/2009 | Bernstein et al. |
| 2009/0137538 A1 | 5/2009 | Klamerus et al. |
| 2009/0143344 A1 | 6/2009 | Chang |
| 2009/0164341 A1 | 6/2009 | Sunvold et al. |
| 2009/0175799 A1 | 7/2009 | Tamarkin et al. |
| 2009/0181088 A1 | 7/2009 | Song et al. |
| 2009/0186081 A1 | 7/2009 | Slot et al. |
| 2009/0197843 A1 | 8/2009 | Notelovitz et al. |
| 2009/0203658 A1 | 8/2009 | Rose et al. |
| 2009/0214474 A1 | 8/2009 | Jennings |
| 2009/0227025 A1 | 9/2009 | Nichols et al. |
| 2009/0227550 A1 | 9/2009 | Mattern |
| 2009/0232897 A1 | 9/2009 | Sahoo et al. |
| 2009/0258096 A1 | 10/2009 | Cohen |
| 2009/0264395 A1 | 10/2009 | Creasy |
| 2009/0269403 A1 | 10/2009 | Shaked et al. |
| 2009/0285772 A1 | 11/2009 | Phiasivongsa et al. |
| 2009/0285869 A1 | 11/2009 | Trimble |
| 2009/0318558 A1 | 12/2009 | Kim et al. |
| 2009/0324714 A1 | 12/2009 | Kresevic et al. |
| 2009/0325916 A1 | 12/2009 | Zhang et al. |
| 2010/0008985 A1 | 1/2010 | Vermeulen et al. |
| 2010/0028360 A1 | 2/2010 | Atwood |
| 2010/0034838 A1 | 2/2010 | Staniforth et al. |
| 2010/0034880 A1 | 2/2010 | Sintov et al. |
| 2010/0040671 A1 | 2/2010 | Ahmed et al. |
| 2010/0048523 A1 | 2/2010 | Bachman et al. |
| 2010/0055138 A1 | 3/2010 | Jacobs et al. |
| 2010/0074959 A1 | 3/2010 | Hansom et al. |
| 2010/0086501 A1 | 4/2010 | Chang et al. |
| 2010/0086599 A1 | 4/2010 | Huempel et al. |
| 2010/0092568 A1 | 4/2010 | Lerner et al. |
| 2010/0105071 A1 | 4/2010 | Laufer et al. |
| 2010/0119585 A1 | 5/2010 | Hille et al. |
| 2010/0129320 A1 | 5/2010 | Phiasivongsa et al. |
| 2010/0136105 A1 | 6/2010 | Chen et al. |
| 2010/0137265 A1 | 6/2010 | Leonard |
| 2010/0137271 A1 | 6/2010 | Chen et al. |
| 2010/0143420 A1 | 6/2010 | Lee et al. |
| 2010/0143481 A1 | 6/2010 | Shenoy et al. |
| 2010/0150993 A1 | 6/2010 | Theobald et al. |
| 2010/0152144 A1 | 6/2010 | Hermsmeyer |
| 2010/0168228 A1 | 7/2010 | Bose et al. |
| 2010/0183723 A1 | 7/2010 | Laurent-Applegate et al. |
| 2010/0184736 A1 | 7/2010 | Coelingh Bennink et al. |
| 2010/0190758 A1 | 7/2010 | Fauser et al. |
| 2010/0204326 A1 | 8/2010 | D Souza |
| 2010/0210994 A1 | 8/2010 | Zarif |
| 2010/0221195 A1 | 9/2010 | Ziv et al. |
| 2010/0227797 A1 | 9/2010 | Danielsson et al. |
| 2010/0240626 A1 | 9/2010 | Kulkarni et al. |
| 2010/0247482 A1 | 9/2010 | Chen et al. |
| 2010/0247632 A1 | 9/2010 | Dong et al. |
| 2010/0247635 A1 | 9/2010 | Schmidt et al. |

(56) References Cited

U.S. PATENT DOCUMENTS

| | | |
|---|---|---|
| 2010/0255085 A1 | 10/2010 | Liu et al. |
| 2010/0273730 A1 | 10/2010 | Hsu et al. |
| 2010/0278759 A1 | 11/2010 | Murad |
| 2010/0279988 A1 | 11/2010 | Setiawan et al. |
| 2010/0291191 A1 | 11/2010 | Lapitsky et al. |
| 2010/0292199 A1 | 11/2010 | Leverd et al. |
| 2010/0303825 A9 | 12/2010 | Sirbasku |
| 2010/0312137 A1 | 12/2010 | Gilmour et al. |
| 2010/0316724 A1 | 12/2010 | Whitfield et al. |
| 2010/0322884 A1 | 12/2010 | Wilkins et al. |
| 2010/0330168 A1 | 12/2010 | Gicquel et al. |
| 2011/0028439 A1 | 2/2011 | Witt-Enderby et al. |
| 2011/0039814 A1 | 2/2011 | Ross et al. |
| 2011/0053845 A1 | 3/2011 | Levine et al. |
| 2011/0066473 A1 | 3/2011 | Bernick et al. |
| 2011/0076775 A1 | 3/2011 | Stewart et al. |
| 2011/0076776 A1 | 3/2011 | Stewart et al. |
| 2011/0086825 A1 | 4/2011 | Chatroux |
| 2011/0087192 A1 | 4/2011 | Uhland et al. |
| 2011/0091555 A1 | 4/2011 | De Luigi Bruschi et al. |
| 2011/0098258 A1 | 4/2011 | Canet et al. |
| 2011/0098631 A1 | 4/2011 | McIntyre et al. |
| 2011/0104268 A1 | 5/2011 | Segot et al. |
| 2011/0104289 A1 | 5/2011 | Savoir Vilboeuf et al. |
| 2011/0130372 A1 | 6/2011 | Marliani et al. |
| 2011/0135719 A1 | 6/2011 | Besins et al. |
| 2011/0142945 A1 | 6/2011 | Chen et al. |
| 2011/0152840 A1 | 6/2011 | Lee et al. |
| 2011/0158920 A1 | 6/2011 | Fisher et al. |
| 2011/0171140 A1 | 7/2011 | Illum et al. |
| 2011/0182997 A1 | 7/2011 | Lewis et al. |
| 2011/0190201 A1 | 8/2011 | Wood, Jr. et al. |
| 2011/0195031 A1 | 8/2011 | Du Tao |
| 2011/0195114 A1 | 8/2011 | Carrara et al. |
| 2011/0195944 A1 | 8/2011 | Mura et al. |
| 2011/0217341 A1 | 9/2011 | Sah |
| 2011/0238003 A1 | 9/2011 | Karabelas Argeris et al. |
| 2011/0244043 A1 | 10/2011 | Wang et al. |
| 2011/0250256 A1 | 10/2011 | Hyun Oh et al. |
| 2011/0250259 A1 | 10/2011 | Buckman |
| 2011/0250274 A1 | 10/2011 | Shaked et al. |
| 2011/0256092 A1 | 10/2011 | Phiasivongsa et al. |
| 2011/0262373 A1 | 10/2011 | Umbert Millet |
| 2011/0262494 A1 | 10/2011 | Achleitner et al. |
| 2011/0268665 A1 | 11/2011 | Tamarkin et al. |
| 2011/0275584 A1 | 11/2011 | Volkmann et al. |
| 2011/0281832 A1 | 11/2011 | Wennogle et al. |
| 2011/0287094 A1 | 11/2011 | Penhasi et al. |
| 2011/0293720 A1 | 12/2011 | General et al. |
| 2011/0294738 A1 | 12/2011 | Kuliopulos et al. |
| 2011/0300167 A1 | 12/2011 | Covic et al. |
| 2011/0301087 A1 | 12/2011 | McBride et al. |
| 2011/0306579 A1 | 12/2011 | Stein |
| 2011/0311592 A1 | 12/2011 | Birbara |
| 2011/0312927 A1 | 12/2011 | Nachaegari et al. |
| 2011/0312928 A1 | 12/2011 | Nachaegari et al. |
| 2011/0318405 A1 | 12/2011 | Erwin |
| 2011/0318431 A1 | 12/2011 | Gulati |
| 2012/0009276 A1 | 1/2012 | De Groote |
| 2012/0015350 A1 | 1/2012 | Nabatiyan et al. |
| 2012/0021041 A1 | 1/2012 | Rossi et al. |
| 2012/0028888 A1 | 2/2012 | Janz et al. |
| 2012/0028910 A1 | 2/2012 | Takruri et al. |
| 2012/0028936 A1 | 2/2012 | Popova et al. |
| 2012/0045532 A1 | 2/2012 | Cohen |
| 2012/0046264 A1 | 2/2012 | Lieb et al. |
| 2012/0046518 A1 | 2/2012 | Yoakum et al. |
| 2012/0052077 A1 | 3/2012 | Truitt, III et al. |
| 2012/0058171 A1 | 3/2012 | Zeeman et al. |
| 2012/0058962 A1 | 3/2012 | Sparrow et al. |
| 2012/0058979 A1 | 3/2012 | Auspitz et al. |
| 2012/0064135 A1 | 3/2012 | Harms et al. |
| 2012/0065179 A1 | 3/2012 | Andersson |
| 2012/0065221 A1 | 3/2012 | Babul |
| 2012/0087872 A1 | 4/2012 | Schuz et al. |
| 2012/0101073 A1 | 4/2012 | Mannion et al. |
| 2012/0121517 A1 | 5/2012 | Kim et al. |
| 2012/0121692 A1 | 5/2012 | Fang et al. |
| 2012/0122829 A1 | 5/2012 | Masini et al. |
| 2012/0128625 A1 | 5/2012 | Shalwitz et al. |
| 2012/0128654 A1 | 5/2012 | Terpstra et al. |
| 2012/0128683 A1 | 5/2012 | Shantha |
| 2012/0128733 A1 | 5/2012 | Perrin et al. |
| 2012/0128777 A1 | 5/2012 | Keck et al. |
| 2012/0129773 A1 | 5/2012 | Geier et al. |
| 2012/0129819 A1 | 5/2012 | Vancaillie et al. |
| 2012/0136013 A1 | 5/2012 | Wennogle et al. |
| 2012/0142645 A1 | 6/2012 | Marx |
| 2012/0148670 A1 | 6/2012 | Lee et al. |
| 2012/0149748 A1 | 6/2012 | Shanler et al. |
| 2012/0172343 A1 | 7/2012 | Schuermann et al. |
| 2012/0184515 A1 | 7/2012 | Schwede et al. |
| 2012/0231052 A1 | 9/2012 | Brinton et al. |
| 2012/0232011 A1 | 9/2012 | Kneissel et al. |
| 2012/0232042 A1 | 9/2012 | Krenz et al. |
| 2012/0263679 A1 | 10/2012 | Wallace et al. |
| 2012/0269721 A1 | 10/2012 | Weng et al. |
| 2012/0269878 A2 | 10/2012 | Cantor et al. |
| 2012/0277249 A1 | 11/2012 | Tarrand et al. |
| 2012/0277727 A1 | 11/2012 | Doshi et al. |
| 2012/0283671 A1 | 11/2012 | Shibata et al. |
| 2012/0295911 A1 | 11/2012 | Mannion et al. |
| 2012/0301517 A1 | 11/2012 | Warner et al. |
| 2012/0301538 A1 | 11/2012 | Latere Dwan Isa et al. |
| 2012/0302535 A1 | 11/2012 | Caufriez et al. |
| 2012/0316130 A1 | 12/2012 | Hendrix |
| 2012/0316496 A1 | 12/2012 | Horres et al. |
| 2012/0321579 A1 | 12/2012 | Edelson et al. |
| 2012/0322779 A9 | 12/2012 | Voskuhl |
| 2012/0328549 A1 | 12/2012 | Edelson et al. |
| 2012/0329738 A1 | 12/2012 | Liu |
| 2013/0004619 A1 | 1/2013 | Goh et al. |
| 2013/0011342 A1 | 1/2013 | Hazot et al. |
| 2013/0017239 A1 | 1/2013 | Fernandez et al. |
| 2013/0022674 A1 | 1/2013 | Dudley et al. |
| 2013/0023505 A1 | 1/2013 | Garfield et al. |
| 2013/0023823 A1 | 1/2013 | Volland et al. |
| 2013/0028850 A1 | 1/2013 | Hazot et al. |
| 2013/0029947 A1 | 1/2013 | Nachaegari et al. |
| 2013/0029957 A1 | 1/2013 | Venkateshwaran et al. |
| 2013/0045266 A1 | 2/2013 | Kang et al. |
| 2013/0045953 A1 | 2/2013 | Grenier et al. |
| 2013/0059795 A1 | 3/2013 | Lo et al. |
| 2013/0064897 A1 | 3/2013 | Binay |
| 2013/0072466 A1 | 3/2013 | Choi et al. |
| 2013/0084257 A1 | 4/2013 | Ishida et al. |
| 2013/0085123 A1 | 4/2013 | Zhao et al. |
| 2013/0089574 A1 | 4/2013 | Stock et al. |
| 2013/0090318 A1 | 4/2013 | Gainer et al. |
| 2013/0102781 A1 | 4/2013 | Ely et al. |
| 2013/0108551 A1 | 5/2013 | Gruell et al. |
| 2013/0116215 A1 | 5/2013 | Lleo et al. |
| 2013/0116222 A1 | 5/2013 | Altomari et al. |
| 2013/0122051 A1 | 5/2013 | Gullapalli et al. |
| 2013/0123175 A1 | 5/2013 | McKee et al. |
| 2013/0123220 A1 | 5/2013 | Queiroz |
| 2013/0123351 A1 | 5/2013 | Dewitt |
| 2013/0129818 A1 | 5/2013 | Bernick et al. |
| 2013/0131027 A1 | 5/2013 | Schmitz et al. |
| 2013/0131028 A1 | 5/2013 | Snyder et al. |
| 2013/0131029 A1 | 5/2013 | Baltussen et al. |
| 2013/0149314 A1 | 6/2013 | Bullerdiek et al. |
| 2013/0164225 A1 | 6/2013 | Bes0nov et al. |
| 2013/0164346 A1 | 6/2013 | Son et al. |
| 2013/0165744 A1 | 6/2013 | Carson et al. |
| 2013/0178452 A1 | 7/2013 | King |
| 2013/0183254 A1 | 7/2013 | Cochran et al. |
| 2013/0183325 A1 | 7/2013 | Sforzini et al. |
| 2013/0189193 A1 | 7/2013 | Besonov et al. |
| 2013/0189196 A1 | 7/2013 | Tamarkin et al. |
| 2013/0189230 A1 | 7/2013 | Kooy et al. |
| 2013/0189368 A1 | 7/2013 | Mosqueira et al. |
| 2013/0210709 A1 | 8/2013 | Covic et al. |
| 2013/0216550 A1 | 8/2013 | Penninger et al. |

(56) References Cited

U.S. PATENT DOCUMENTS

| | | |
|---|---|---|
| 2013/0216596 A1 | 8/2013 | Fernandez et al. |
| 2013/0224177 A1 | 8/2013 | Kim et al. |
| 2013/0224257 A1 | 8/2013 | Sah et al. |
| 2013/0224268 A1 | 8/2013 | Jaikaria et al. |
| 2013/0224300 A1 | 8/2013 | Maggio |
| 2013/0225412 A1 | 8/2013 | Sardari Lodriche et al. |
| 2013/0225542 A1 | 8/2013 | Frick et al. |
| 2013/0226113 A1 | 8/2013 | Langguth et al. |
| 2013/0243696 A1 | 9/2013 | Wang et al. |
| 2013/0245253 A1 | 9/2013 | Mook et al. |
| 2013/0245570 A1 | 9/2013 | Jackson |
| 2013/0261096 A1 | 10/2013 | Merian et al. |
| 2013/0266645 A1 | 10/2013 | Schoenecker et al. |
| 2013/0267485 A1 | 10/2013 | Da Silva Maia Filho |
| 2013/0273167 A1 | 10/2013 | Kim et al. |
| 2013/0274211 A1 | 10/2013 | Prusthy et al. |
| 2013/0280213 A1 | 10/2013 | Voskuhl |
| 2013/0316374 A1 | 11/2013 | Menon et al. |
| 2013/0317065 A1 | 11/2013 | Seto et al. |
| 2013/0317315 A1 | 11/2013 | Tsang et al. |
| 2013/0324565 A1 | 12/2013 | Zhao et al. |
| 2013/0331363 A1 | 12/2013 | Zhao et al. |
| 2013/0338122 A1* | 12/2013 | Bernick et al. ............... 514/170 |
| 2013/0338123 A1* | 12/2013 | Bernick et al. ............... 514/170 |
| 2013/0338124 A1 | 12/2013 | Zhao et al. |
| 2013/0345187 A1 | 12/2013 | Rodriguez Oquendo |
| 2014/0018335 A1 | 1/2014 | Seto et al. |
| 2014/0024590 A1 | 1/2014 | Taylor et al. |
| 2014/0031289 A1 | 1/2014 | Kim et al. |
| 2014/0031323 A1 | 1/2014 | Perez |
| 2014/0066416 A1 | 3/2014 | Leunis et al. |
| 2014/0072531 A1 | 3/2014 | Oh et al. |
| 2014/0079686 A1 | 3/2014 | Prouty et al. |
| 2014/0088051 A1 | 3/2014 | Bernick et al. |
| 2014/0088058 A1 | 3/2014 | Maurizio |
| 2014/0088059 A1 | 3/2014 | Santha et al. |
| 2014/0094426 A1 | 4/2014 | Drummond et al. |
| 2014/0094440 A1 | 4/2014 | Bernick et al. |
| 2014/0094441 A1 | 4/2014 | Bernick et al. |
| 2014/0099362 A1 | 4/2014 | Bernick et al. |
| 2014/0100159 A1 | 4/2014 | Conrad |
| 2014/0100204 A1 | 4/2014 | Bernick et al. |
| 2014/0100205 A1 | 4/2014 | Bernick et al. |
| 2014/0100206 A1 | 4/2014 | Cacace et al. |
| 2014/0113889 A1 | 4/2014 | Haine et al. |
| 2014/0127185 A1 | 5/2014 | Sayeed et al. |
| 2014/0127280 A1 | 5/2014 | Jukarainen et al. |
| 2014/0127308 A1 | 5/2014 | Opara et al. |
| 2014/0128798 A1 | 5/2014 | Malanchin et al. |
| 2014/0148491 A1 | 5/2014 | Valia et al. |
| 2014/0186332 A1 | 7/2014 | Ezrin et al. |
| 2014/0187487 A1 | 7/2014 | Shoichet et al. |
| 2014/0193523 A1 | 7/2014 | Henry |
| 2014/0194396 A1 | 7/2014 | Wennogle et al. |
| 2014/0206616 A1 | 7/2014 | Ko et al. |
| 2014/0213565 A1 | 7/2014 | Bernick et al. |
| 2014/0371182 A1 | 12/2014 | Bernick et al. |
| 2014/0371183 A1 | 12/2014 | Bernick et al. |
| 2014/0371184 A1* | 12/2014 | Bernick et al. ............... 514/170 |
| 2014/0371185 A1* | 12/2014 | Bernick et al. ............... 514/170 |
| 2015/0031654 A1* | 1/2015 | Amadio ....................... 514/170 |
| 2015/0045335 A1* | 2/2015 | Bernick et al. ............... 514/182 |
| 2015/0133421 A1 | 5/2015 | Bernick et al. |

FOREIGN PATENT DOCUMENTS

| | | |
|---|---|---|
| EP | 0275716 A1 | 7/1988 |
| EP | 0279977 A2 | 8/1988 |
| EP | 0622075 A1 | 11/1994 |
| EP | 0785211 A1 | 1/1996 |
| EP | 0785212 A1 | 1/1996 |
| EP | 0811381 A1 | 6/1997 |
| EP | 1094781 B1 | 7/2006 |
| EP | 1094781 B1 | 7/2008 |
| EP | 2191833 A1 | 6/2010 |
| GB | 452238 A | 8/1936 |
| GB | 720561 | 12/1954 |
| GB | 848881 A | 9/1960 |
| GB | 874368 | 8/1961 |
| GB | 1589946 A | 5/1981 |
| IN | 216026 | 3/2008 |
| IN | 2005KO00053 | 9/2009 |
| IN | 244217 | 11/2010 |
| WO | 9011064 A1 | 10/1990 |
| WO | 9317686 A1 | 9/1993 |
| WO | 9422426 A1 | 3/1994 |
| WO | 9530409 A1 | 11/1995 |
| WO | 9609826 A2 | 4/1996 |
| WO | 9619975 | 7/1996 |
| WO | 9630000 | 10/1996 |
| WO | 9705491 | 2/1997 |
| WO | 9743989 A1 | 11/1997 |
| WO | 9810293 A1 | 3/1998 |
| WO | 9832465 A1 | 7/1998 |
| WO | 9851280 A1 | 11/1998 |
| WO | 9939700 A1 | 2/1999 |
| WO | 9932072 A1 | 7/1999 |
| WO | 9939700 A1 | 8/1999 |
| WO | 9942109 A1 | 8/1999 |
| WO | 9943304 | 9/1999 |
| WO | 9948477 A1 | 9/1999 |
| WO | 9953910 A2 | 10/1999 |
| WO | 9963974 A2 | 12/1999 |
| WO | 0001351 A1 | 1/2000 |
| WO | 0006175 A1 | 2/2000 |
| WO | 0038659 A1 | 7/2000 |
| WO | 0045795 A2 | 8/2000 |
| WO | 0050007 A1 | 8/2000 |
| WO | 0059577 A1 | 10/2000 |
| WO | 0076522 A1 | 12/2000 |
| WO | 0137808 A1 | 5/2001 |
| WO | 0154699 A1 | 8/2001 |
| WO | 0160325 A1 | 8/2001 |
| WO | 0187276 A1 | 11/2001 |
| WO | 0207700 A2 | 1/2002 |
| WO | 0211768 A1 | 2/2002 |
| WO | 0222132 A2 | 3/2002 |
| WO | 0240008 A2 | 5/2002 |
| WO | 0241878 | 5/2002 |
| WO | 02053131 A1 | 7/2002 |
| WO | 02078602 A3 | 2/2003 |
| WO | 03028667 | 4/2003 |
| WO | 03041718 A1 | 5/2003 |
| WO | 03041741 A1 | 5/2003 |
| WO | 03068186 A1 | 8/2003 |
| WO | 03077923 A1 | 9/2003 |
| WO | 03082254 A1 | 10/2003 |
| WO | 02078604 A3 | 11/2003 |
| WO | 03092588 A2 | 11/2003 |
| WO | 2004014397 A1 | 2/2004 |
| WO | 2004014432 | 2/2004 |
| WO | 2004017983 A1 | 3/2004 |
| WO | 2004032897 A2 | 4/2004 |
| WO | 2004052336 A2 | 6/2004 |
| WO | 2004054540 A2 | 7/2004 |
| WO | 2004080413 A2 | 9/2004 |
| WO | 2005027911 A1 | 3/2005 |
| WO | 2005030175 A1 | 4/2005 |
| WO | 2005081825 | 9/2005 |
| WO | 2005087194 A1 | 9/2005 |
| WO | 2005087199 A1 | 9/2005 |
| WO | 2005105059 A1 | 11/2005 |
| WO | 2005115335 A1 | 12/2005 |
| WO | 2005120470 A1 | 12/2005 |
| WO | 2005120517 A1 | 12/2005 |
| WO | 2006013369 A1 | 2/2006 |
| WO | 2006034090 A1 | 3/2006 |
| WO | 2006036899 A2 | 4/2006 |
| WO | 2006053172 A2 | 5/2006 |
| WO | 2006105615 A1 | 10/2006 |
| WO | 2006113505 A2 | 10/2006 |
| WO | 2006138686 A1 | 12/2006 |
| WO | 2006138735 A2 | 12/2006 |

(56) References Cited

FOREIGN PATENT DOCUMENTS

| | | |
|---|---|---|
| WO | 2007045027 A1 | 4/2007 |
| WO | 2007103294 A2 | 9/2007 |
| WO | 2006138735 A3 | 10/2007 |
| WO | 2007120868 | 10/2007 |
| WO | 2007123790 A1 | 11/2007 |
| WO | 2007124250 A2 | 11/2007 |
| WO | 2007124250 A3 | 12/2007 |
| WO | 2007144151 A1 | 12/2007 |
| WO | 2007103294 A3 | 4/2008 |
| WO | 2008049516 A3 | 5/2008 |
| WO | 2008049516 A3 | 6/2008 |
| WO | 2008152444 A2 | 12/2008 |
| WO | 2009002542 A1 | 12/2008 |
| WO | 2009036311 A1 | 3/2009 |
| WO | 2009040818 | 4/2009 |
| WO | 2008152444 A3 | 6/2009 |
| WO | 2009069006 A2 | 6/2009 |
| WO | 2009098072 A2 | 8/2009 |
| WO | 2009098072 A3 | 10/2009 |
| WO | 2009133352 A2 | 11/2009 |
| WO | 2009069006 A3 | 12/2009 |
| WO | 2010033188 A2 | 3/2010 |
| WO | 2009133352 A3 | 10/2010 |
| WO | 2010146872 | 12/2010 |
| WO | 2011000210 A1 | 1/2011 |
| WO | 2011073995 A2 | 6/2011 |
| WO | 2011073995 A3 | 8/2011 |
| WO | 2011120084 A1 | 10/2011 |
| WO | 2011128336 A1 | 10/2011 |
| WO | 2010033188 A3 | 11/2011 |
| WO | 2012009778 A2 | 1/2012 |
| WO | 2012024361 A1 | 2/2012 |
| WO | 2012055814 A1 | 5/2012 |
| WO | 2012055840 A1 | 5/2012 |
| WO | 2012065740 | 5/2012 |
| WO | 2012098090 A1 | 7/2012 |
| WO | 2012116277 A1 | 8/2012 |
| WO | 2012118563 A2 | 9/2012 |
| WO | 2012120365 A1 | 9/2012 |
| WO | 2012127501 A2 | 9/2012 |
| WO | 2012156561 A1 | 11/2012 |
| WO | 2012156822 A1 | 11/2012 |
| WO | 2012158483 A2 | 11/2012 |
| WO | 2012166909 A1 | 12/2012 |
| WO | 2012170578 A1 | 12/2012 |
| WO | 2013011501 A1 | 1/2013 |
| WO | 2012009778 A3 | 2/2013 |
| WO | 2013025449 A1 | 2/2013 |
| WO | 2013028639 A1 | 2/2013 |
| WO | 2013035101 A1 | 3/2013 |
| WO | 2013044067 A1 | 3/2013 |
| WO | 2013045404 A2 | 4/2013 |
| WO | 2013059285 A1 | 4/2013 |
| WO | 2013063279 A1 | 5/2013 |
| WO | 2013064620 A1 | 5/2013 |
| WO | 2013071281 A1 | 5/2013 |
| WO | 2013088254 | 6/2013 |
| WO | 2013102665 A1 | 7/2013 |
| WO | 2013106437 A1 | 7/2013 |
| WO | 2013113690 | 8/2013 |
| WO | 2013124415 A1 | 8/2013 |
| WO | 2013127727 A1 | 9/2013 |
| WO | 2013127728 A1 | 9/2013 |
| WO | 2013144356 A1 | 10/2013 |
| WO | 2013149258 A2 | 10/2013 |
| WO | 2013158454 A2 | 10/2013 |
| WO | 2013170052 A1 | 11/2013 |
| WO | 2013178785 A1 | 12/2013 |
| WO | 2013181449 A1 | 12/2013 |
| WO | 2013192248 A1 | 12/2013 |
| WO | 2013192249 A1 | 12/2013 |
| WO | 2013192250 A1 | 12/2013 |
| WO | 2013192251 A1 | 12/2013 |
| WO | 2014001904 A | 1/2014 |
| WO | 2014004424 A1 | 1/2014 |
| WO | 2014009434 A1 | 1/2014 |
| WO | 2014018569 A1 | 1/2014 |
| WO | 2014018570 A1 | 1/2014 |
| WO | 2014018571 A2 | 1/2014 |
| WO | 2014018856 A1 | 1/2014 |
| WO | 2014018932 A2 | 1/2014 |
| WO | 2014031958 A1 | 2/2014 |
| WO | 2014041120 A1 | 3/2014 |
| WO | 2014052792 A1 | 4/2014 |
| WO | 2014056897 A1 | 4/2014 |
| WO | 2014066442 A2 | 5/2014 |
| WO | 2014074846 A1 | 5/2014 |
| WO | 2014076231 A1 | 5/2014 |
| WO | 2014076569 A2 | 5/2014 |
| WO | 2014081598 A1 | 5/2014 |
| WO | 2014086739 A1 | 6/2014 |
| WO | 2014093114 A1 | 6/2014 |
| WO | 2014104784 A1 | 7/2014 |

OTHER PUBLICATIONS

Banerjee, Sila, et al., On the Stability of Salivary Progesterone Under Various Conditions of Storage, Steroids, vol. 46(6), pp. 967-974, Dec. 1985.

Barnett, Steven M, Pressure-tuning infared and solution Raman spectroscopic studies of 17B-estradiol and several A-ring . . . , Vibrational Spectroscopy 8, Elsevier, pp. 263, 1995.

Bernabei, M.T., et al., Release of progesterone polymorphs from dimethylpolysiloxane polymeric matrixes, Bollettino Chimico Farmaceutico, vol. 122(1) pp. 20-26, 1983 SciFinder.

Bhavnani, B.R., Stanczyk, F.Z., Pharmacology of conjugated equine estrogens: Efficacy, safety and mechanism of action, J. Steroid Biochem. Mol. Biol. (2013), Elsevier.

Bhavnani, B.R., Stanczyk, F.Z., Use of medroxyprogesterone acetate for hormone therapy in postmenopausal women: Is it safe? J. Steroid Biochem. Mol. Biol. (2013), Elsevier.

Brandstatter-Kuhnert, M, Zur mikroskopischen Identitatsprufing und zur Polymorphie der Sexualhormone, Acta, vol. 6, pp. 847-853, 1959, Univ. Innsbruck.

Brinton, L.A., Felix, A.S., Menopausal hormone therapy and risk of endometrial cancer, J. Steroid Biochem. Mol. Biol. (2013), Elsevier.

Burry, Kenneth A, Percutaneous absorption of progesterone in postmenopausal women treated with transdermal estrogen, Am J Obstet Gynecol, vol. 180(6) part 1, pp. 1504-1511, 1999.

Busetta, Par Bernard, Structure Cristalline et Moleculair de l'Oestradiol Hemihydrate, Acta Cryst., B28 pp. 560, 1972, Bis(dimethyl-o-thiolophenylarsine)palladium(II).

Busetta, Par Bernard, Structure Cristalline et Moleculaire du Complexe Oestradiol-Propanol, Acta Cryst., B28 pp. 1349, 1972, J.A. Kanters and J. Kroon.

Campsteyn, Par H, et al., Structure Cristalline et Molcculaire de la Progesterone C21H30O2, Acta Cryst., B28 pp. 3032-3042, 1972.

Cendejas-Santana, G, et al., Growth and characterization of progesterone crystallites, Revista Mexicana de Fisica, 50, Suplemento 1 pp. 1-3, 2004.

Cole, Wayne & Julian, Percy L, Sterols. I. A Study of the 22-Ketosteroids, Cont. of the Research Lab. of the Glidden Co., Soya Prod. Div., vol. 67 pp. 1369-1375, Aug. 1945, Chicago.

Commodari, Fernando, Comparison of 17B-estradiol structures from x-ray diffraction and solution NMR, Magn. Reson. Chem., vol. 43, pp. 444-450, 2005, Wiley InterScience.

Cooper, A, et al., Systemic absorption of progesterone from Progest cream in postmenopausal women, The Lancet, vol. 351, pp. 1255-1256, Research Letters, Apr. 25, 1998.

Dideberg, O, et al., Crystal data on progesterone (C21H30O2), desoxycorticosterone (C21H30O3), corticosterone (C21H30O4) and aldosterone . . . , J. Appl. Cryst. vol. 4 pp. 80, 1971.

Drakulic, Branko J, Role of complexes formation between drugs and penetration enhancers in transdermal . . . , Inter. Journal of Pharmaceutics, Elsevier, vol. 363, pp. 40-49, 2009.

Duax, William L, et al., Conformation of Progesterone Side Chain: Conflict between X-ray Data and Force-Field Calculations, J. Am. Chem. Soc., vol. 103 pp. 6705-6712, Jun. 1981.

(56) References Cited

OTHER PUBLICATIONS

Duclos, R, et al., Polymorphism of Progesterone: Influence of the carrier and of the solid dispersion manufacturing . . . , J. Thermal Anal., vol. 37 pp. 1869-1875, 1991, Wiley.
Ebian, A.R., Ebian Article: Polymorphism and solvation of ethinyl estradiol, SciFinder, Pharmaceutica Acta Helvetiae, vol. 54(4), pp. 111-114, 1979, Alexandria, Egypt.
Eisenberger, A., Westhoff, C., Hormone replacement therapy and venous thromboembolism, J. Steroid Biochem. Mol. Biol. (2013), Elsevier.
Faassen, Fried, Physicochemical Properties and Transport of Steroids across Caco-2 Cells, Pharmaceutical Research, vol. 20(2), 2003, Plenum Pub. Corp.
FDA, Draft Guidance on Progesterone, Recommended Apr. 2010, Revised Feb. 2011 http://www.fda.gov/downloads/Drugs/GuidanceComplianceRegulatoryInformation/Guidances/UCM209294.pdf.
Freedman, R.R., Menopausal hot flashes: Mechanisms, endocrinology, treatment, J. Steroid Biochem. Mol. Biol. (2013), Elsevier.
Fugh-Berman, Adriane, Bioidentical Hormones for Menopausal Hormone Therapy: Variation on a Theme, Journal of General Internal Medicine, vol. 22, pp. 1030-1034, 2007.
Giron, D, Thermal analysis and calorimetric methods in the characterisation of polymorphs and solvates, Thermochimica Acta, vol. 248 pp. 1-59, 1995, Elsevier.
Giron-Forest, D, et al., Thermal analyis methods for pharmacopoeial materials, J. Pharmaceutical & Biomedical Anal., vol. 7(12) pp. 1421-1433, 1989, Pergamon Press, Gr. Britain.
Gurney, E.P., et al., The Women's Health Initiative trial and related studies: 10 years later: A clinician's view, J. Steroid Biochem. Mol. Biol. (2013), Elsevier.
Haner, Barbara A., Crystal data (I) for some pregnenes and pregnadienes, Acta Cryst., vol. 17 pp. 1610, 1964.
Hapgood, J.P., et al., Potency of progestogens used in hormonal therapy: Toward understanding differential actions, J. Steroid Biochem. Mol. Biol. (2013), Elsevier.
Helbling, Ignacio M, et al., The Optimization of an Intravaginal Ring Releasing Progesterone Using a Mathematical Model, Pharm Res, vol. 31 pp. 795-808, 2014, Springer Science.
Henderson, V.W., Alzheimer's disease: Review of hormone therapy trials and implications for treatment and prevention after . . . , J. Steroid Biochem. Mol. Biol. (2013), Elsevier.
Henriksen, Thormod, et al., An ENDOR Sturdy of Radiation-Induced Molecular Damage to Progesterone, Jour. of Mag. Resonance, vol. 63, pp. 333-342, 1985, Acedemic Press, Inc.
Hodis, H.N., Mack, W.J., Hormone replacement therapy and the association with heart disease and overall mortality: Clinical . . . , J. Steroid Biochem. Mol. Biol. (2013), Elsevier.
Hospital, Michel, et al., X-ray Crystallography of Estrogens and Their Binding to Receptor Sites, Mol. Pharmacology, vol. 8 pp. 438-445, Acedemic Press, Inc., 1972.
Hulsmann, Stefan, Stability of Extruded 17B-Estradiol Solid Dispersions, Pharmaceutical Development and Tech., vol. 6(2) pp. 223-229, 2001, Marcel Dekker, Inc.
Idder, Salima, et al., Physicochemical properties of Progesterone, SciFinder, pp. 1-26, Feb. 24, 2014, American Chem. Society & US Natl. Lib. of Med.
Johnson, William S, et al., Racemic Progesterone, Tetrahedron Letters No. 4, pp. 193-196, 1963, Pergamon Press Ltd., Great Britain.
Khalil, Sah, Stability and Dissolution Rates of Corticosteroids in Polyethylene Glycol Solid Dispersions, Drug Dev. & Indus. Pharm., vol. 10(5) pp. 771-787, 1984, Marcel Dekker.
Korkmaz, Filiz, Byophysical Studies of Progesterone—Model Membrane Interactions, Thesis, Grad. School of Nat. and App. Sci. of the Middle East Tech. University, Sep. 2003.
Kotiyan, P.N., Stability indicating HPTLC method for the estimation of estradiol, Journal of Pharmaceutical and Biomedical Analysis, vol. 22 pp. 667-671, 2000, Elsevier.

Krzyminiewski, R, et al., EPR Study of the Stable Radical in a γ-Irradiated Single Crystal of Progesterone, Jour. of Mag. Resonance, vol. 46 pp. 300-305, 1982, Acedemic Press.
Stein, Emily A, et al., Progesterone Physical Properties, SciFinder, pp. 1-46, Feb. 24, 2014, American Chem. Society & US Natl. Lib. of Med.
Stein, Emily A, et al., Progesterone Physical Properties, SciFinder, pp. 1-46, Mar. 3, 2014, American Chem. Society & US Natl. Lib. of Med.
Stein, Emily A, et al., Progesterone, SciFinder Scholar Search, pp. 1-46, Feb. 24, 2014, American Chem. Society & Natl. Lib. of Med.
Tait, Alex D, Characterization of the Prod. from the Oxidation of Progesterone with Osmium Tetroxide, Dept of Investigative Med., Univ. Cambridge, Gt. Britain pp. 531-542, 1972.
Takacs M, et al., The light sensitivity of corticosteroids in crystalline form, Pharmaceutica acta Helvetiae, vol. 66 (5-6) pp. 137-140, 1991, Hardin Library.
Tella, S.H., Gallagher, J.C., Prevention and treatment of postmenopausal osteoporosis, J. Steroid Biochem. Mol. Biol. (2013), Elsevier.
Thomas, Joshua, et al., The effect of water solubility of solutes on their flux through human skin in vitro: An . . . , Intl. J. of Pharmaceut., vol. 339 pp. 157-167, 2007, Elsevier.
Tripathi, R, et al., Study of Polymorphs of Progesterone by Novel Melt Sonocrystallization Technique: A Technical Note, AAPS PhamSciTech, vol. 11, No. 3, Sep. 2010.
USP Monographs: Progesterone, USP29, www.pharmacopeia.cn/v29240/usp29nf24s0_m69870.html, search done: Feb. 25, 2014.
Utian, Wulf H, et al., Relief of vasomotor symptoms and vaginal atrophy with lower doses of conjugated equine estrogens . . . Fertility and Sterility, vol. 75(6) pp. 1065, Jun. 2001.
Weber, M.T., et al., Cognition and mood in perimenopause: A systematic review and meta-analysis, J. SteroidBiochem. Mol. Biol. (2013), Elsevier.
Wiranidchapong, Chutima, Method of preparation does not affect the miscibility between steroid hormone and polymethacrylate, Thermochimica Acta 485, Elsevier, pp. 57, 2009.
Yalkowsky, Samuel H, & Valvani, Shri C, Solubility and Partitioning I: Solubility of Nonelectrolytes in Water, J. of Pharmaceutical Sciences, vol. 69(8) pp. 912-922, 1980.
Yue, W.,Genotoxic metabolites of estradiol in breast: potential mechanism of estradiol induced carcinogenesis, Journal of Steroid Biochem & Mol Biology, vol. 86 pp. 477-486, 2003.
Kubli-Garfias, C, et al., Ab initio calculations of the electronic structure of glucocorticoids, Jour. of Mol. Structure, Theochem, vol. 454 pp. 267-275, 1998, Elsevier.
Kubli-Garfias, Carlos, Ab initio study of the electronic structure of progesterone and related progestins, Jour. of Mol. Structure, Theochem vol. 425, pp. 171-179, 1998, Elsevier.
Kuhnert-Brandstaetter, M & Kofler, A, Zur Unterscheidung von losungsmittelhaltigen pseudopolymorphen Kristallformen und polymorphen Modifikationen bei Steroidhormonen.II. vol. 1 pp. 127-139, 1968, Mikrochimica Acta.
Kuhnert-Brandstaetter, M & Lnder, R, Zur Hydratbildung bei Steroidhormonen, Sci. Pharm., vol. 41(2) pp. 109-116, 1973.
Kuhnert-Brandstatter, M, Thermo-microscopic and spectrophotometric: Determination of steroid hormones, Microchemical Journal 9, pp. 105-133, 1965.
Labrie, et al., Intravaginal prasterone (DHEA) provides local action without clinically significant changes in serum concentrations of estrogens or androgens, Journal of Steroid Biochemistry & Molecular Biology, vol. 138, pp. 359-367, 2013, Elsevier.
Lacey, J.V. Jr., The WHI ten year's later: An epidemiologist's view, J. Steroid Biochem. Mol. Biol. (2013), Elsevier.
Lahiani-Skiba, Malika, Solubility and Dissolution Rate of Progesterone-Cyclodextrin . . . , Drug Development and Industrial Pharmacy, Informa Healthcare vol. 32, pp. 1043-1058, 2006.
Lancaster, Robert W, et al., The Polymorphism of Progesterone: Stabilization of a 'Disappearing' Polymorph by . . . , Jour. of Pharm. Sci., vol. 96(12) pp. 3419-3431, 2007, Wiley-Liss.
Land, Laura M, The influence of water content of triglyceride oils on the solubility of steriods, Pharmaceutical Research, vol. 22(5) May 2005, Springer Science+Business Media.

(56) References Cited

OTHER PUBLICATIONS

Leonetti, Helene B, et al., Topical progesterone cream has an antiproliferative effect on estrogen-stimulated endometrium, Fertility and Sterility, vol. 79(1), Jan. 2003.
Lewis, John G., et al., Caution on the use of saliva measurements to monitor absorption of progesterone . . . , Maturitas, The European Menopaus Journal, vol. 41, pp. 1-6, 2002.
Li, Guo-Chian, Solid-state NMR analysis of steroidal conformation of 17a- and 17B-estradiol in the absence and presence of lipi . . . , Steroids, Elsevier, vol. 77, pp. 185-192, 2012.
Lobo, R.A., Foreword, J. Steroid Biochem. Mol. Biol. (2014), Elsevier.
Lvova, M. SH., et al., Thermal Analysis in the Quality Control and Standardization of Some Drugs, J Thermal Anal., vol. 40 pp. 405-411, 1993, Wiley.
Magness, R.R., et al., Estrone, Estradiol-17b and Progesterone Concentrations in Uterine Lymph and Systematic Blood . . . , Journal of Animal Science, vol. 57, pp. 449-455, ISU, 1983.
McGuffy, Irena, Softgel Technology as a Lipid-Based Delivery Tool for Bioavailability Enhancement, Catalent Pharma Solutions, Somerset, NJ, Mar. 2011.
Merck Index Online, Progesterone, Royal Society of Chemistry, 2013, search Feb. 24, 2014 https://www.rsc.org/Merck-Index/monograph/print/mono1500007889/progesterone?q=authorize.
Merck Index, Estradiol, The Merck Index Online, Royal Society of Chemistry 2014, MONO1500003758.
Mesley, R.J., Clathrate Formation from Steroids, Chemistry and Industry, vol. 37 pp. 1594-1595, Sep. 1965.
Mueck, A.O., et al., Genomic and non-genomic actions of progestogens in the breast, J. Steroid Biochem. Mol.Biol. (2013), Elsevier.
Muramatsu, Mitsuo, Thermodynamic Relationship between a- and B- Forms of Crystalline Progesterone, J. Pharmaceutical Sciences, vol. 68(2) pp. 175-178, 1979, Amer. Pharm. Assoc.
Nicklas, Martina, Preparation and characterization of marine sponge collagen nanoparticles and employment for the trans . . . , Drug Devel. & Indust. Pharmacy,35(9) pp. 1035, 2009.
O'Leary, Peter, Salivary, but not serum or urinary levels of progesterone are elevated after topical . . . , Clinical Endocrinology, vol. 53 pp. 615-620, Blackwell Science 2000.
Open Notebook, Science Solubility Challenge, Jul. 16, 2013, Solubility of progesterone in organic solvents, http://Ixsrv7.oru.edu/~alang/onsc/solubility/allsolvents.php?solute=progesterone.
Park, Jeong-Sook, Solvent effects on physicochemical behavior of estradiols recrystalized for transdermal delivery, Arch Pharm Res, vol. 31(1), pp. 111-116, 2008.
Park, Jeong-Sook, Use of CP/MAS solid-state NMR for the characterization of solvate . . . , European Journal of Pharmaceutics and Biopharmaceutics, vol. 60, pp. 407-412, 2005.
Parrish, Damon A., A new estra-1,3,5(10)-triene-3,17b-diol solvate: estradiol-methanol-water, Crystal Structure Comm., Intn'l Union of Crystallography, ISSN 0108-2701, 2003.
Payne, R.S., et al., Examples of successful crystal structure prediction: polymorphs of primidone and progesterone, Intl. Jour. of Pharma., vol. 177 pp. 231-245, 1999, Elsevier.
Pinkerton, J.V., Thomas, S., Use of SERMs for treatment in postmenopausal women, J. Steroid Biochem. Mol. Biol. (2014), Elsevier.
Pisegna, Gisia L, A High-pressure Vibrational Spectroscopic Study of Polymorphism in Steroids . . . , Thesis, McGill University, Dept. of Chem, Nov. 1999, Natl. Lib. of Canada.
Price, Sarah L, The computational prediction of pharmaceutical crystal structures and polymorphism, Adv. Drug Delivery Reviews, vol. 56 pp. 301-319, 2004, Elsevier.
Progynova TS 100, available online at file:///C:/Users/Call%20Family/Desktop/Progynova%20TS%20100%2012%20Patches_Pack%20%28Estradiol%20Hemihydrate%29.html, 2010.
Rosilio, V, et al., Physical Aging of Progesterone-Loaded Poly(D,L,-lactide-co-glycolide) Microspheres, Pharmaceutical Research, vol. 15(5) pp. 794-799,1998, Plenum Pub. Corp.
Santen, R.J., Menopausal hormone therapy and breast cancer, J. Steroid Biochem. Mol. Biol. (2013), Elsevier.
Sarkar, Basu, et al., Chemical Stability of Progesterone in Compounded Topical Preparations using PLO Transdermal Cream™ and HRT Cream™ Base . . . , J Steroids Horm Sci, 4:2, 2013.
Satyanarayana, D, et al., Aqueous Solubility Predictions of Aliphatic Alcohols, Alkyl Substituted Benzoates and Steroids, Asian J. Chem., vol. 9 (3) pp. 418-426, 1997.
Schindler, A. E., The "newer" progestogens and postmenopausal hormone therapy (HRT), J. Steroid Biochem.Mol. Biol. (2013), Elsevier.
SciFinder Scholar Prednisone Chemical Properties, SciFinder, 2014, pp. 1-7, National Library of Medicine.
SciFinder Scholar Prednisone Physical Properties, SciFinder, 2014, pp. 1-10, Natioinal Library of Medicine.
SciFinder Scholar Progesterone Experimental Properties, SciFinder, pp. 1-9, Feb. 24, 2014, American Chem. Society.
Azeem et al., "Microemulsions as a Surrogate Carrier for Dermal Drug Delivery," Drug Development and Industrial Pharmacy, 35(5):525-547. 2009. Abstract Only.
Azure Pharma, Inc., "ELESTRIN™—Estradiol Gel" Drug Info, http://dailymed.nlm.nih.gov/dailymed/archives/fdaDrugInfo.cfm?archiveid=11885, 26 pages, 2009.
Chun et al., "Transdermal Delivery of Estradiol and Norethindrone Acetate: Effect of Vehicles and Pressure Sensitive Adhesive Matrix," J. Kor. Pharm. Sci., 35(3):173-177, 2005.
Committee of Obstetric Practice, Committee Opinion—No. 522, Obstetrics & Gynecology, 119(4):879-882, 2012.
Diramio, "Polyethylene Glycol Methacrylate/Dimetacrylate Hydrogels for Controlled Release of Hydrophobic Drugs," The University of Georgia-Masters of Science Thesis, 131 pages, 2004. http://athenaeum.libs.uga.edu/bitstream/handle/10724/7820/diramio_jackie_a_200412_ms.pdf?sequence=1.
Ganem-Quintanar et al., "Evaluation of the transepidermal permeation of diethylene glycol monoethyl ether and skin water loss," International Journal of Pharmaceutics, 147(2):165-171, 1997. Abstract Only.
Knuth et al., "Hydrogel delivery systems for vaginal and oral applications: Formulation and biological considerations," Advanced Drug Delivery Reviews, 11(1-2):137-167, 1993. Abstract Only.
Lucy et al., "Gonadotropin-releasing hormone at estrus: luteinizing hormone, estradiol, and progesterone during the periestrual and postinsemination periods in dairy cattle," Biol Reprod., 35(2):300-11, 1986. Abstract Only.
NuGen, "What is NuGen HP Hair Growth System?" http://www.skinenergizer.com/Nugen-HP-Hair-Growth-System-p/senusystem.htm, 3 pages, undated.
NuGest 900™, http://www.thehormoneshop.net/nugest900.htm, 4 pages, undated.
Panchagnula et al., "Development and evaluation of an intracutaneous depot formulation of corticosteroids using Transcutol as a cosolvent: in-vitro, ex-vivo and in-vivo rat studies," J Pharm Pharmacol.;43(9):609-14, 1991. Abstract Only.
Salole, "The physiochemical properties of oestradiol," Journal of Pharmaceutical & Biomedical Analysis, 5(7):635-648, 1987.
Strickley, "Solubilizing Excipients in Oral and Injectable Formulations," Pharmaceutical Research, 21(2):201-230. 2004.
Tahition Noni, "Body Balance Cream," http://products.tni.com/dominican_republic/sa_spanish/nonistore/product/3438/3416/, 1 page, undated.
Trommer et al., "Overcoming the Stratum Corneum: The Modulation of Skin Penetration," Skin Pharmacol Physiol., 19:106-121, 2006. http://www.nanobiotec.iqm.unicamp.br/download/Trommer_skin%20penetration-2006rev.pdf.
Abitec, CapmulMCM, EP, Technical Data Sheet, version 10, 2014, Columbus, OH.
Abitec, CapmulMCM, NF, Technical Data Sheet, version 6, 2014, Columbus, OH.
Abitec, CapmulMCM, Saftey Data Sheet, 2011, Janesville, WI.

(56) References Cited

OTHER PUBLICATIONS

Abitec, CapmulMCM, Technical Data Sheet, version 17, 2014, Columbus, OH.
Abitec, CapmulPG8, CAS No. 31565-12-5, version 11, 2006, Columbus, OH.
Alabi, K. A., et al., Analysis of Fatty Acid Composition of Thevetia peruviana and Hura crepitans Seed oils using GC-FID, Fountain Journal of Nat. and Appl. Sciences, vol. 2(2), pp. 32-37, 2013, Osogbo.
Alexander, KS, Corn Oil, CAS No. 8001-30-7, Jan. 2009.
British Pharmacopocia 2014 Online, Refined Maize Oil, Ph. Eur. Monograph 1342, vol. I & II, Monographs: Medicinal and Pharmaceutical Substances, http://www.pharmacopoeia.co.uk/bp2014/ixbin/bp.cgi?a=print&id=7400&tab=a-z%20index[Feb. 3, 2014 1:37:50 PM].
ChemPro, Top-Notch Technology in Production of Oils and Fats, Chempro-Edible-Oil-Refining-ISO-TUV-Austria.
Corn Refiners Assoc, Corn Oil, 5th Edition, Washington, D.C., 2006.
Dauqan, Eqbal M. A., et al., Fatty Acids Composition of Four Different Vegetable Oils (Red Palm Olein, Palm Olein, Corn Oil, IPCBEE, vol. 14, 2011, IACSIT Press, Singapore.
Ferrari, Roseli AP., et al., Oxidative Stability of Biodiesel From Soybean Oil Fatty Acid Ethyl Esters, Sci. Agric., vol. 62(3), pp. 291-295, 2005, Piracicaba, Braz.
Ng, Jo-Han, et al., Advances in biodiesel fuel for application in compression ignition engines, Clean Techn Environ Policy, vol. 12, pp. 459-493, 2010, Springer-Verlag.
Notelovitz, Morris, et al., Initial 17-b-Estradiol Dose for Treating Vasomotor Symptoms, Obstetrics & Gynecology, vol. 95(5), pp. 726-731, part 1, May 2000, Elsevier.
Prajapati, Hetal N, et al., A comparative Evaluation of Mono-, Di- and Triglyceride of Medium Chain Fatty Acids by Lipid/Surfactant/Water, Springerlink.com, pp. 1-21, Apr. 2011.
Strocchi, Antonino, Fatty Acid Composition, and Triglyceride Structure of Corn Oil, Hydrogenated Corn Oil, and Corn Oil Margarine, Journal of Food Science, vol. 47, pp. 36-39, 1981.
USP, 401 Fats and Fixed Oils, Chemical Tests, Second Suplement to USP36-NF 31, pp. 6141-6151, 2013.
USP, Lauroyl Polyoxylglycerides, Saftey Data Sheet, US, 5611 Version #02, pp. 1-9, 2013.
USP, Official Monographs, Corn Oil, NF 31, pp. 1970-1971, Dec. 2013.
USP, Official Monographs, Lauroyl Polyoxylglycerides, NF 31, pp. 2064-2066, Dec. 2013.
USP, Official Monographs, Medium Chain Triglycerides, NF 31, pp. 2271-2272, Dec. 2013.
USP, Official Monographs, Mono- and Di-glycerides, NF 31, pp. 2101, Dec. 2013.
USP, USP Certificate—Corn Oil, Lot G0L404, Jul. 2013.
Weber, E.J., Corn Lipids, Cereal Chem., vol. 55(5), pp. 572-584, The American Assoc of Cereal Chem, Sep.-Oct. 1978.
Araya-Sibaja, et al., Crystallization of progesterone polymorphs using polymer-induced heteronucleation (PIHn) method, Drug Development and Industrial Pharmacy, Early Online, pp. 1-8, 2014, Informa Healthcare.
PCCA, Apothogram, PCCA, May 2014, Houston, TX.
International Search Report and Written Opinion for related International Application No. PCT/US13/023309 mailed Apr. 9, 2013.
Acarturk, Fusun, Mucoadhesive Vaginal Drug Delivery Systems, Recent Patents on Drug Delivery & Formulation, vol. 3, pp. 193-205, 2009, Bentham Science Publishers, Ltd.
Bhavnani, Bhagu R., et al., Misconception and Concerns about Bioidentical Hormones Used for Custom-Compounded Hormone Therapy, J Clin Endocrin Metab., vol. 97(3), Mar. 2012, The Endocrine Society 2011.
Bhavnani, Bhagu R., et al., Structure Activity Relationships and Differential Interactions and Functional Activity of Various Equine Estrogens Mediated via Estrogen Receptors (ER) and ERa and ERB, Endocrinology, Oct. 2008, vol. 149(10), pp. 4857-4870, The Endocrine Society 2008.
Du, Joanna Y., et al., Percutaneous progesterone delivery via cream or gel application in postmenopausal women: a randomized cross-over study of progesterone levels in serum, whole blood, saliva, and capillary blood, Menopause: The Journal of the North American Menopause Society, vol. 20(11), pp. 000-000, The North American Menopause Society 2013.
Fotherby, K, Bioavailability of Orally Administered Sex Steroids Used in Oral Contraception and Hormone Replacement Therapy, Contraception, vol. 54, pp. 59-69, Elsevier Science, Inc. 1996.
Fuchs, Katie O., et al., The Effects of an Estrogen and Glycolic Acid Cream on the Facial Skin of Postmenopausal Women: A Randomized Histologic Study, Pharmacology/Cosmetology, vol. 5(1), 2006.
Hargrove, Joel T., et al., Menopausal Hormone Replacement Therapy With Continuous Daily Oral Micronized Estradiol and Progesterone, Estrogen Replacement Therapy, Obstetrics & Gynecology, vol. 73(4), pp. 606-612, Apr. 1989, The American College of Obstetricians and Gynecologists.
ISR and written opinion for PCT/US/13/46442, dated Nov. 1, 2013.
ISR and written opinion for PCT/US/13/46443, dated Oct. 31, 2013.
ISR and written opinion for PCT/US/13/46444, dated Oct. 31, 2013.
ISR and written opinion for PCT/US/13/46445, dated Nov. 1, 2013.
Kincl, Fred A., et al., Short Communication, Increasing Oral Bioavailability of Progesterone by Formulation, Journal of Steroid Biochemistry, vol. 9, pp. 83-84 Pergamon Press 1978, Great Britain.
The Journal of the North American Menopause Society (NAMS), Management of symptomatic vulvovaginal atrophy: 2013 position statement of The North American Menopause Society, Menopause, vol. 20(9), pp. 888-902, The North American Menopause Society 2013.
Panay, Nick, The 2013 British Menopause Society & women's Health Concern recommendations on hormone replacement therapy, Menopause International, The Integrated Journal of Postreproductive Health, vol. 0(0), Sage 2013.
Patel, Dipen, et al., Transdermal Drug Delivery System: A Review, The Pharma Innovation, The Pharma Journal, vol. 1 (4), 2012.
Sarrel, Philip M., et al., The Mortality Toll of Estrogen Avoidance: An Analysis of Excess Deaths Among Hysterectomized Women Aged 50 to 59 Years, American Journal of Public Health, Research and Practice, pp. e1-e6, Published online ahead of print Jul. 18, 2013.
Shufelt, Chrisandra L., et al., Hormone therapy dose, formulation, route of delivery, and risk of cardiovascular events in women: findings from the Women's Health Initiative Observational Study, Menopause: The Journal of The North American Menopause Society (NAMS), vol. 21(3), pp. 000-000, The North American Menopause Society 2013.
Simon, James, et al., Effective Treatment of Vaginal Atrophy With an Ultra-Low-Dose Estradiol Vaginal Tablet, Obstetrics & Gynecology, vol. 112(5), pp. 1053-1060, pp. 373-402, Nov. 2008.
Sitruk-Ware, Regine, et al., Oral Micronized Progesterone, Contraception, vol. 36(4), Oct. 1987.
Sitruk-Ware, Regine, Progesterones in hormonal replacement therapy: new molecules, risks, and benefits, Menopause: The Journal of the North American Menopause Society (NAMS), vol. 9(1), pp. 6-15, The North American Menopause Society 2002.
Smith, Nicholas L., et al., Lower Risk of Cardiovascular Events in Postmenopausal Women Taking Oral Estradiol Compared with Oral Conjugated Equine Estrogens, JAMA Intern Med, pp. e1-e7, published online Sep. 30, 2013.
Stanczyk, Frank, et al., Ethinyl estradiol and 17B-estradiol in combined oral contraceptives: pharmacokinetics, pharmacodynamics and risk assessment, Contraception, vol. 87, pp. 706-727, Elsevier 2013.
USPTO, Final Office Action dated Jul. 16, 2013 for U.S. Appl. No. 13/684,002.
USPTO, Non-Final Office Action dated Mar. 20, 2013 for U.S. Appl. No. 13/684,002.
USPTO, Notice of allowance dated Dec. 6, 2013 for U.S. Appl. No. 13/684,002.
USPTO, Non-Final Office Action dated Feb. 18, 2014 for U.S. Appl. No. 14/099,545.
USPTO, Restriction/Election Requirement dated Feb. 20, 2014 for U.S. Appl. No. 14/099,562.

(56) References Cited

OTHER PUBLICATIONS

USPTO, Restriction/Election Requirement dated Mar. 5, 2014 for U.S. Appl. No. 14/099,623.
Whitehead, M. I., et al., Absorption and Metabolism of Oral Progesterone, The British Medical Journal, vol. 280(6217), pp. 825-827, Mar. 22, 1980, BMJ Publishing Group, JSTOR.
Wood, Charles E., et al., Effects of estradiol with micronized progesterone or medroxyprogesterone acetate on risk markers for breast cancer in postmenopausal monkeys, Breast Cancer Res Treat, vol. 101, pp. 125-134, published online Jul, 14, 2006, Springer Science + Business Media B.V. 2006.
Acarturk, "Mucoadhesive Vaginal Drug Delivery System," Recent Patents on Drug Delivery & Formulation, 3 (3):193-205, 2009.
Fuchs et al., "The Effects of an Estrogen and Glycolic Acid Cream on the Facial Skin of Postmenopausal Women: A Randomized Histologic Study," Aesthetic Dermatology, 8(1):14-19, 2006.
Panay et al., "The 2013 British Menopause Society & Women's Health Concern recommendations on hormone replacement therapy," DOI: 0.1177/1754045313489645, min.sagepub.com. Menopause International: The Integrated Journal of Postreproductive Health 0(0):1-10, 2013.
Extended European Search Report for European Application No. EP13741053.6, dated Jul. 1, 2015.
Abbas et al., Regression of endometrial implants treated with vitamin D3 in a rat model of endometriosis, European J of Pharma, 715 (2013) 72-75, Elsevier.
Abitec, Excipients for the Pharmaceutical Industry—Regulatory and Product Information, 2013, 2 pages.
Alvarez et al., Ectopic uterine tissue as a chronic pain generator, Neuroscience, Dec. 6, 2012 225: 269-272.
Application Note FT-IR: JI-AP-FT0508-008, CD Spectra of Pharmaceuticals Substances—Steroids (2), JASCO International Co., Ltd., 2 Pages.
Archer et al., Effects of Ospemifene on the Female Reproductive and Urinary Tracts: Translation From Preclinical Models Into Clinical Evidence, Menopause: The Journal of the North American Menopause Society, vol. 22, No. 77, pp. 1-11 (2015).
Archer et al., Estrace® vs Premarin® for Treatment of Menopausal Symptoms: Dosage Comparison Study, Advances in Therapy®, vol. 9 No. 1, Jan./Feb. 1992.
Ashburn et al., Cardiovascular, Hepatic and Renal Lesions in Mice Receiving Cortisone, Estrone and Progesterone, Yale J Bilogy and Medicine, vol. 35, Feb. 1963, pp. 329-340.
Bartosova, Transdermal Drug Delivery In Vitro Using Diffusion Cells, Current Medicinal Chemistry, 2012, 19, 4671-4677, Bentham Science Publishers.
Benbow et al., Distribution and Metabolism of Maternal Progesterone in the Uterus, Placenta, and Fetus during Rat Pregnancy, Biology of Reproduction 52, 1327-1333 (1995).
Blake et al., Single and multidose pharmacokinetic study of a vaginal micronized progesterone insert (Endometrin) compared with vaginal gel in healthy reproductiveaged female subjects, Fertility and Sterility# vol. 94, No. 4, Sep. 2010, Elsevier.
Christen et al., Phase I/Pharmacokinetic Study of High-Dose Progesterone and Doxorubicin, J Clin Oncol 11:2417-2426, 1993.
Christensson et al., Limonene hydroperoxide analogues differ in allergenic activity, Contact Dermatitis 2008: 59: 344-352.
Christensson et al., Limonene hydroperoxide analogues show specific patch test reactions, Contact Dermatitis, 70, 291-299, 2014.
Christensson et al., Positive patch test reactions to oxidized limonene: exposure and relevance, Contact Dermatitis, 71, 264-272, 2014.
Cicinelli et al., Direct Transport of Progesterone From Vagina to Uterus, Obstetrics & Gynecology, vol. 95, No. 3, March 2000, pp. 403-406.
Committee Opinion, Incidentally Detected Short Cervical Length, Committee of Obstetric Practice, Obstetrics & Gynecology, ACOG, vol. 119, No. 4, Apr. 2012, pp. 879-882.

Corbett et al., "Trends in Pharmacy Compounding for Women's Health in North Carolina: Focus on Vulvodynia," Southern Medical Journal, Vol. 107, No. 7, Jul. 2014, pp. 433-436.
Critchley et al., Estrogen Receptor β, But Not Estrogen Receptor α, Is Present in the Vascular Endothelium of the Human and Nonhuman Primate Endometrium, The Journal of Clinical Endocrinology & Metabolism, 2001, vol. 86, No. 3, pp. 1370-1378.
Engelhardt et al., Conceptus Influences the Distribution of Uterine Leukocytes During Early Porcine Pregnancy, Biology of Reproduction 66, 1875-1880 (2002).
Ettinger et al., Comparison of Endometrial Growth Produced by Unopposed Conjugated Estrogens or by Micronized Estradiol in Postmenopausal Women, Am J Obstet Gynecol 1997; 176:112-117.
Excipients for Pharmaceuticals, Sasol Olefins & Surfactants GmbH, 2010, 28 pages.
Filipsson et al., Concise International Chemical Assessment Document 5: Limonene, first draft, World Health Organization, Geneva, 1998, 36 pages.
Final Report on the Safety Assessment of BHT, International Journal of Toxicology, 21(Suppl. 2):19-94, 2002/.
Flyvholm, Sensitizing risk of butylated hydroxytoluene based on exposure and effect data, Contact Dermatitis 1990: 23: 341-345.
Franklin et al., Characterization of immunoglobulins and cytokines in human cervical mucus: influence of exogenous and endogenous hormones, Journal of Reproductive Immunology 42 (1999) 93-106, Elsevier.
Franz et al., Use of Excised Human Skin to Assess the Bioequivalence of Topical Products, Skin Pharmacol Physiol 2009;22:276-286.
Furness et al., Hormone therapy in postmenopausal women and risk of endometrial hyperplasia (Review), 2012, pp. 1-204, The Cochrane Collaboration. Published by JohnWiley & Sons, Ltd.
Gäfvert et al., Free radicals in antigen formation: reduction of contact allergic response to hydroperoxides by epidermal treatment with antioxidants, British Journal of Dermatology 2002; 146: 649-656.
Gattefossé SAS, Material Safety Data Sheet, Gelot 64, 2012, 8 pages.
Gattefossé SAS, Regulatory Data Sheet, Gelot 64, 2012, 6 pages.
Gattefossé SAS, Regulatory Data Sheet, Lauroglycol 90, 2012, 5 pages.
Gattefossé, "Excipients for Safe and Effective Topical Delivery, Drug Development and Delivery" Jul./Aug. 2012, http://drug-dev.com/Main/Back-Issues/Transdermal-Topical-Subcutaneous-NonInvasive-Deliv-5.aspx#.
Geelen, Math J.H. et al., "Dietary medium-chain fatty acids raise and (n-3) polyunsaturated fatty acids lower hepatic triacylglycerol synthesis in rats," The Journal of Nutrition, 1995, 125(10):2449-2456.
Gillet et al., Induction of amenorrhea during hormone replacement therapy: optimal micronized progesterone dose. A multicenter study, Maturitas 19 (1994) 103-115.
Glaser et al, Pilot Study: Absorption and Efficacy of Multiple Hormones Delivered in a Single Cream Applied to the Mucous Membranes of the Labia and Vagina, Gynecol Obstet Invest 2008;66:111-118.
Golatowski et al., Comparative evaluation of saliva collection methods for proteome analysis, Clinica Chimica Acta 419 (2013) 42-46.
Graham et al, Physiological Action of Progesterone in Target Tissues, Endocrine Reviews, 1997, vol. 18, No. 4, pp. 502-519.
Groothuis et al., Estrogen and the endometrium: lessons learned from gene expression profiling in rodents and human, Human Reproduction Update, vol. 13, No. 4 pp. 405-417, 2007.
Hamid et al., The effects of common solubilizing agents on the intestinal membrane barrier functions and membrane toxicity in rats, International Journal of Pharmaceutics 379 (2009) 100-108, Elsevier.
Hatton et al., "Safety and efficacy of a lipid emulsion containing medium-chain triglycerides," Clinical Pharmacy, 1990, vol. 9, No. 5, pp. 366-371.
He et al., Apoptotic Signaling Pathways in Uteri of Rats with Endometrial Hyperplasia Induced by Ovariectomy Combined with Estrogen, Gynecol Obstet Invest 2013;76:51-56.
Helmy et al., Estrogenic Effect of Soy Phytoestrogens on the Uterus of Ovariectomized Female Rats, Clinic Pharmacol Biopharmaceut, 2014, S2, 7 pages.

(56) References Cited

OTHER PUBLICATIONS

Herman, Anna et al., "Essential oils and their constituents as skin penetration enhancer for transdermal drug delivery: a review," 2014 Royal Pharmaceutical Society, Journal of Pharmacy and Pharmacology, pp. 1-13.
Hostynek, JJ, Predictinga bsorptiono f fragrancec hemicalst hrough human skin, j. Soc.C osmeCt. hem.,4 6, 221-229 (Jul./Aug. 1995).
Hurn et al., Estrogen as a Neuroprotectant in Stroke, Journal of Cerebral Blood Flow and Metabolism 20:631-652, 2000, Lippincott Williams & Wilkins, Inc., Philadelphia.
Hyder et al., Synthetic Estrogen 17α-Ethinyl Estradiol Induces Pattern of Uterine Gene Expression Similar to Endogenous Estrogen 17β-Estradiol, JPET 290(2):740-747, 1999.
Joshi et al., Detection and synthesis of a progestagen-dependent protein in human endometrium, J Reprod Fert (1980) 59, 273-285.
Kanno et al., The OECD Program to Validate the Rat Uterotrophic Bioassay to Screen Compounds for in Vivo Estrogenic Responses: Phase 1, Environmental Health Perspectives • vol. 109 | No. 8 | Aug. 2001, pp. 785-794.
Karlberg et al., Air oxidation of d-limonene (the citrus solvent) creates potent allergens, Contact Dermatitis, 1992: 26: 332-340.
Karlberg et al., Influence of an Anti-Oxidant on the Formation of Allergenic Compounds During Auto-Oxication of d-Limonene, Ann. Occup. Hyg., vol. 38, No. 2, pp. 199-207, 1994.
Kaunitz, Andrew M., Extended duration use of menopausal hormone therapy, Menopause: The Journal of The North American Menopause Society, 2014, vol. 21, No. 6, pp. 1-3.
Kharode et al., The Pairing of a Selective Estrogen Receptor Modulator, Bazedoxifene, with Conjugated Estrogens as a New Paradigm for the Treatment of Menopausal Symptoms and Osteoporosis Prevention, Endocrinology 149(12):6084-6091, 2008.
Kim et al., Safety Evaluation and Risk Assessment of d-Limonene, Journal of Toxicology and Environmental Health, Part B: Critical Reviews, 2013, 16:1, 17-38 http://dx.doi.org/10.1080/10937404.2013.769418.
Koga et al., Enhancing mechanism of Labrasol on intestinal membrane permeability of the hydrophilic drug gentamicin sulfate, European Journal of Pharmaceutics and Biopharmaceutics 64 (2006) 82-91.
Komm et al., Bazedoxifene Acetate: A Selective Estrogen Receptor Modulator with Improved Selectivity, Endocrinology 146(9):3999-4008, 2005.
Kumasaka et al., Effects of Various Forms of Progestin on the the Estrogen-Primed, Ovariectomized Rat, Endocrine Journal 1994, 41(2), 161-169.
Kuon et al., A Novel Optical Method to Assess Cervical Changes during Pregnancy and Use to Evaluate the Effects of Progestins on Term and Preterm Labor, Am J Obstet Gynecol. Jul. 2011; 205(1): 82.e15-82.e20.
Kuon et al., Actions of progestins for the inhibition of cervical ripening and uterine contractions to prevent preterm birth, FVV in OBGYN, 2012, 4 (2): 110-119.
Kuon et al., Pharmacological actions of progestins to inhibit cervical ripening and prevent delivery depend upon their properties, the route of administration and the vehicle, Am J Obstet Gynecol. May 2010; 202(5): 455.e1-455.e9.
Lauer et al., "Evaluation of the hairless rat as a model for in vivo percutaneous absorption," Journal of Pharmaceutical Sciences, vol. 86, No. 1, Jan. 1997, pp. 13-18.
Leonetti et al., Transdermal progesterone cream as an alternative progestin in hormone therapy, Alternative Therapies, Nov./Dec. 2005, vol. 11, No. 6, pp. 36-38.
López-Belmonte, Corrigendum to "Comparative uterine effects on ovariectomized rats after repeated treatment with different vaginal estrogen formulations" [Maturitas 72 (2012) 353-358], Maturitas 74 (2013) 393, Elsevier.
Madishetti et al., Development of domperidone bilayered matrix type transdermal patches: physicochemical, in vitro and ex vivo characterization, DARU vol. 18, No. 3, 2010, pp. 221-229.

Manson, JoAnn E. et al., "Menopausal hormone therapy and health outcomes during the intervention and extended poststopping phases of the women's health initiative randomized trials," JAMA, Oct. 2, 2013, vol. 310, No. 13, pp. 1353-1368.
Miles et al., Pharmacokinetics and endometrial tissue levels of progesterone after administration bv'Intramuscular and vaginal routes: a comparative study, Fertility and Sterility, vol. 62, No. 3, Sep. 1994, pp. 485-490.
Miller et al., Safety and Feasibility of Topical Application of Limonene as a Massage Oil to the Breast, Journal of Cancer Therapy, 2012, 3, 749-754.
Nilsson et al., Analysis of Contact Allergenic Compounds in Oxidized d-Limonene, Chromatographia vol. 42, No. 3/4, Feb. 1996, pp. 199-205.
Opinion on the Diethylene Glycol Momoethyl Ether (DEGEE), Scientific Committee on Consumer Products, Dec. 19, 2006, 27 pages.
Outterson, K., The Drug Quality and Security Act—Mind the Gaps, n engl j med 370;2 nejm.org Jan. 9, 2014, pp. 97-99.
Palamakula et al., Preparation and In Vitro Characterization of Self-Nanoemulsified Drug Delivery Systems of Coenzyme Q10 Using Chiral Essential Oil Components, Pharmaceutical Technology Oct. 2004, pp. 74-88.
Parasuraman et al., Blood sample collection in small laboratory animals, Journal of Pharmacology & Pharmacotherapeutics | Jul.-Dec. 2010 | vol. 1 | Issue 2, pp. 87-93.
Pfaus et al., Selective facilitation of sexual solicitation in the female rat by a melanocortin receptor agonist, PNAS, Jul. 6, 2004, vol. 101, No. 27, pp. 10201-10204.
Pickles, VR, Cutaneous reactions to injection of progesterone solutions into the skin, BR Med Journal, Aug. 16, 1952, pp. 373-374.
Pinkerton et al., What are the concerns about custom-compounded "bioidentical" hormone therapy? Menopause: The Journal of The North American Menopause Society, vol. 21, No. 12, 2014,pp. 1-3.
Portman, David et al., One-year treatment persistence with local estrogen therapy in postmenopausal women diagnosed as having vaginal atrophy, Menopause, vol. 22, No. 11, 2015, pp. 000/000 (8 pages).
Prausnitz et al., Transdermal drug delivery, Nat Biotechnol. Nov. 2008; 26(11): 1261-1268.
Product Safety Assessment: Diethylene Glycol Monoethyl Ether, Created: Sep. 24, 2007 The Dow Chemical Company Page, 5 pages.
Provider Data Sheet, About Dried Blood Spot Testing, ZRT Laboratory, 2014, 3 pages.
Rahn et al., Vaginal Estrogen for Genitourinary Syndrome of Menopause a Systematic Review, Obstet Gynecol 2014;124(6):1147-56.
Rao, Rajeswara et al., "Intra Subject Variability of Progesterone 200 mg Soft Capsules in Indian Healthy Adult Postmenopausal Female Subjects under Fasting Conditions," J Bioequiv Availab. 2014,6: 139-143.
Reisman et al., Topical Application of the Synthetic Triterpenoid RTA 408 Protects Mice from Radiation-Induced Dermatitis, Radiation Research 181, 512-520 (2014).
Ross et al., Randomized, double-blind, dose-ranging study of the endometrial effects of a vaginal progesterone gel in estrogen-treated postmenopausal women, AnnJ Obstet Gynecol, Oct. 1997, vol. 177, No. 4, pp. 937-941.
Ruan et al., Systemic progesterone therapy—Oral, vaginal, injections and even transdermal? Maturitas 79 (2014) 248-255, Elsevier.
Salem, HF, Sustained-release progesterone nanosuspension following intramuscular injection in ovariectomized rats, International Journal of Nanomedicine 2010:5 943-954, Dove Press.
Salole, Eugene G., Estradiol, Analytical Profiles of Drug Substances, vol. 15, pp. 283-318, 1986.
Santen, RJ, Vaginal administration of estradiol: effects of dose, preparation and timing on plasma estradiol levels, Climacteric 2014;17:1-14.
Schindler, Aldof E. et al., Classification and pharmacology of progestins, Maturitas 46S1 (2003) S7-S16.
Schutte et al., A tissue engineered human endometrial stroma that responds to cues for secretory differentiation, decidualization and menstruation, Fertil Steril. Apr. 2012; 97(4): 997-1003, Elsevier.

(56) References Cited

OTHER PUBLICATIONS

Schweikart et al., Comparative Uterotrophic Effects of Endoxifen and Tamoxifen in Ovariectomized Sprague-Dawley Rats, Toxicologic Pathology, 42: 1188-1196, 2014.
Shao et al., REVIEW Open Access Direct effects of metformin in the endometrium: a hypothetical mechanism for the treatment of women with PCOS and endometrial carcinoma, Journal of Experimental & Clinical Cancer Research 2014, 33(1):41, 11 pages.
Shrier et al., "Mucosal Immunity of the Adolescent Female Genital Tract," Journal of Adolescent Health, 2003; 32:183-186.
Siew, Adeline, moderator, Bioavailability Enhancement with Lipid-Based Drug-Delivery Systems, Pharmaceutical Technology, Aug. 2014, pp. 28, 30-31.
Simon, James A., What if the Women's Health Initiative had used transdermal estradiol and oral progesterone instead? Menopause: The Journal of the North American Menopause Society, 2014, vol. 21, No. 7, pp. 1-15.
Sitruk-Ware, Regine, "Pharmacological profile of progestins," Maturitas 47 (2004) 277-283.
Smyth et al., Summary of Toxicological Data, a 2-Yr Study of Diethylene Glycol Monoethyl Ether in Rats, Fd Cosmet. Toxicol. vol. 2, pp. 641-642, 1964.
Stanczyk et al., Thereaputically equivalent pharmacokinetic profile across three application sistes for AG200-15, a novel low-estrogen dose contraceptive patch, Contraception, 87 (2013) pp. 744-749.
Stanczyk, F.Z. et al., "Percutaneous administration of progesterone: blood levels and endometrial protection," Menopause: The Journal of The North American Menopause Society, 2005, vol. 12, No. 2, pp. 232-237.
Stanczyk, F.Z., "All progestins are not created equal," Steroids 68 (2003) 879-880.
Stanczyk, F.Z., "Treatment of postmenopausal women with topical progesterone creams and gels: are they effective?" Climacteric 2014; 17(Suppl 2):8-11.
Stephenson et al., "Transdermal progesterone: Effects on Menopausal symptoms and on thrombotic, anticoagulant, and inflammatory factors in postmenopausal women," Int J Pharmaceutical Compounding, vol. 12, No. 4, Jul./Aug. 2008, pp. 295-304.
Sullivan et al., "A review of the nonclinical safety of Transcutol®, a highly purified form of diethylene glycol monoethyl ether (DEGEE) used as a pharmaceutical excipient," Food and Chemical Toxicology, 72 (2014) pp. 40-50.
Sun, Jidong, D-Limonene: Safety and Clinical Applications, Alternative Medicine Review vol. 12, No. 3, 2007, pp. 259-264.
Tang et al., Effect of Estrogen and Progesterone on the Development of Endometrial Hyperplasia in the Fischer Rat, Biology of Reproduction 31, 399-413 (1984).
Tas et al., Comparison of antiproliferative effects of metformine and progesterone on estrogen-induced endometrial hyperplasia in rats, Gynecol Endocrinol, Early Online: 1-4, 2013. http://informahealthcare.com/gye.
Thomas, Peter, Characteristics of membrane progestin receptor alpha (mPRα) and progesterone membrane receptor component 1 (PGMRC1) and their roles in mediating rapid progestin actions, Frontiers in Neuroendocrinology 29 (2008) 292-312.
Tuleu et al., "Comparative Bioavailability Study in Dogs of a Self-Emulsifying Formulation of Progesterone Presented in a Pellet and Liquid Form Compared with an Aqueous Suspension of Progesterone," Journal of Pharmaceutical Sciences, vol. 93, No. 6, Jun. 2004, pp. 1495-1502.
Ueda et al., Topical and Transdermal Drug Products, Pharmacopeial Forum, vol. 35(3) [May-Jun. 2009], 750-754.
U.S. Appl. No. 12/561,515 Jan. 29, 2013 Advisory Action (Opera 1.1).
U.S. Appl. No. 12/561,515 Final Office Action dated Oct. 26, 2012 in U.S. Appl. No. 12/561,515 (Opera 1.1).
U.S. Appl. No. 12/561,515 Notice of Allowance dated Sep. 11, 2013 in U.S. Appl. No. 12/561,515 (Opera 1.1).
U.S. Appl. No. 12/561,515 Office Action dated Dec. 12, 2011 in U.S. Appl. No. 12/561,515 (Opera 1.1).
U.S. Appl. No. 13/843,428 Apr. 14, 2015 Restriction Requirement.
U.S. Appl. No. 14/099,545 Jul. 14, 2014 Notice of Allowance.
U.S. Appl. No. 14/099,562 Mar. 27, 2014 Non-Final Office Action.
U.S. Appl. No. 14/099,562 Jul. 2, 2014 Final Office Action.
U.S. Appl. No. 14/099,562 Dec. 10, 2014 Notice of Allowance.
U.S. Appl. No. 14/099,571 Mar. 28, 2014 Restriction Requirement.
U.S. Appl. No. 14/099,571 Jul. 15, 2014 Notice of Allowance.
U.S. Appl. No. 14/099,582 Apr. 29, 2014 Restriction Requirement.
U.S. Appl. No. 14/099,582 Jun. 17, 2014 Non-Final Office Action.
U.S. Appl. No. 14/099,582 Nov. 7, 2014 Notice of Allowance.
U.S. Appl. No. 14/099,582 Jan. 22, 2015 Notice of Allowance.
U.S. Appl. No. 14/099,598 May 13, 2014 Restriction Requirement.
U.S. Appl. No. 14/099,598 Jul. 3, 2014 Non-Final Office Action.
U.S. Appl. No. 14/099,598 Dec. 10, 2014 Notice of Allowance.
U.S. Appl. No. 14/099,612 Mar. 20, 2014 Restriction Requirement.
U.S. Appl. No. 14/099,612 Jul. 30, 2014 Non-Final Office Action.
U.S. Appl. No. 14/099,612 Nov. 26, 2014 Notice of Allowance.
U.S. Appl. No. 14/099,623 Jul. 18, 2014 Non-Final Office Action.
U.S. Appl. No. 14/099,623 Dec. 25, 2014 Notice of Allowance.
U.S. Appl. No. 14/103,355 Dec. 8, 2014 Non-Final Office Action.
U.S. Appl. No. 14/106,655 Jul. 3, 2014 Restriction Requirement.
U.S. Appl. No. 14/125,554 Dec. 5, 2014 Restriction Requirement.
U.S. Appl. No. 14/125,554 Apr. 14, 2015 Non-Final Office Action.
U.S. Appl. No. 14/136,048 Nov. 4, 2014 Restriction Requirement.
U.S. Appl. No. 14/136,048 Mar. 12, 2015 Non-Final Office Action.
U.S. Appl. No. 14/475,814 Oct. 1, 2014 Non-Final Office Action.
U.S. Appl. No. 14/475,814 Feb. 13, 2015 Notice of Allowance.
U.S. Appl. No. 14/475,864 Feb. 11, 2014 Notice of Allowance.
U.S. Appl. No. 14/475,864 Oct. 2, 2014 Non-Final Office Action.
U.S. Appl. No. 14/521,230 Dec. 5, 2014 Restriction Requirement.
U.S. Appl. No. 14/521,230 Feb. 18, 2015 Non-Final Office Action.
U.S. Appl. No. 14/624,051 Apr. 7, 2015 Non-Final Office Action.
Voegtline et al., Dispatches from the interface of salivary bioscience and neonatal research, Frontiers in Endocrinology, Mar. 2014, vol. 5, article 25, 8 pages.
Waddell et al., Distribution and metabolism of topically applied progesterone in a rat model, Journal of Steroid Biochemistry & Molecular Biology 80 (2002) 449-455.
Waddell et al., The Metabolic Clearance of Progesterone in the Pregnant Rat: Absence of a Physiological Role for the Lung, Biology of Reproduction 40, 1188-1193 (1989).
Walter et al., The role of progesterone in endometrial angiogenesis in pregnant and ovariectomised mice, Reproduction (2005) 129 765-777.
Weintraub, Arlene, "Women fooled by untested hormones from compounding pharmacies," Forbes, Feb. 20, 2015; retrieved online at http://onforb.es/1LIUm1V on Feb. 23, 2015, 3 pages.
Wren et al., Effect of sequential transdermal progesterone cream on endometrium, bleeding pattern, and plasma progesterone and salivary progesterone levels in postmenopausal women, Climacteric, 2000, 3(3), pp. 155-160. http://dx.doi.org/10.1080/13697130008500109.
Wu et al., Gene Expression Profiling of the Effects of Castration and Estrogen Treatment in the Rat Uterus, Biology of Reproduction 69, 1308-1317 (2003).
Zava, David T. et al., Percutaneous absorption of progesterone, Maturitas 77 (2014) 91-92, Elsevier.
Zava, David T., Topical Progesterone Delivery and Levels in Serum, Saliva, Capillary Blood, and Tissues, Script, ZRT Laboratory, pp. 4-5. http://www.zrtlab.com/component/docman/cat_view/10-publications?Itemid.
US 6,214,374, 04/2001, Schmirler et al. (withdrawn)

\* cited by examiner

| 1 | 2 | 3 | 4 | 5 | 6 | 7 |
|---|---|---|---|---|---|---|
| storage element (3-4 day E) ||| storage element (3-4 day E) ||||
| 8 | 9 | 10 | 11 | 12 | 13 | 14 |
| storage element (3-4 day E) ||| storage element (3-4 day E) ||||
| 15 | 16 | 17 | 18 | 19 | 20 | 21 |
| storage element (3-4 day E+P) ||| storage element (3-4 day E+P) ||||
| 22 | 23 | 24 | 25 | 26 | 27 | 28 |
| storage element (3-4 day E+P) ||| storage element (3-4 day E+P) ||||

FIG. 4

| 1 | 2 | 3 | 4 | 5 | 6 | 7 |
|---|---|---|---|---|---|---|
| storage element (3-4 day E) | spacer element | spacer element | storage element (3-4 day E) | spacer element | spacer element | spacer element |
| 8 | 9 | 10 | 11 | 12 | 13 | 14 |
| storage element (3-4 day E) | spacer element | spacer element | storage element (3-4 day E) | spacer element | spacer element | spacer element |
| 15 | 16 | 17 | 18 | 19 | 20 | 21 |
| storage element (3-4 day E+P) | spacer element | spacer element | storage element (3-4 day E+P) | spacer element | spacer element | spacer element |
| 22 | 23 | 24 | 25 | 26 | 27 | 28 |
| storage element (3-4 day E+P) | spacer element | spacer element | storage element (3-4 day E+P) | spacer element | spacer element | spacer element |

FIG. 5

TRANSDERMAL HORMONE REPLACEMENT THERAPIES

CROSS REFERENCE TO RELATED APPLICATIONS

This application is a National Stage application under 35 U.S.C. §371 of International Application Serial No. PCT/US2013/023309, entitled "TRANSDERMAL HORMONE REPLACEMENT THERAPIES" which was filed on 25 Jan. 2013, and claims priority to the following: U.S. Provisional Application Ser. No. 61/590,927, entitled "TRANSDERMAL COMBINATION HORMONE REPLACEMENT THERAPIES" which was filed on 26 Jan. 2012; U.S. Provisional Application Ser. No. 61/661,302, entitled "ESTRADIOL FORMULATIONS" which was filed on 18 Jun. 2012; U.S. Provisional Application Ser. No. 61/662,265, entitled "PROGESTERONE FORMULATIONS" which was filed on 20 Jun. 2012; U.S. application Ser. No. 13/684,002, entitled "NATURAL COMBINATION HORMONE REPLACEMENT FORMULATIONS AND THERAPIES" which was filed on 21 Nov. 2012; and U.S. Provisional Application Ser. No. 61/563,408, entitled "NATURAL COMBINATION HORMONE REPLACEMENT THERAPIES" which was filed on 23 Nov. 2011. All of the aforementioned applications are hereby incorporated by reference herein in their entirety.

FIELD

This disclosure relates to natural estrogen and progesterone replacement therapies, with transdermal formulations provided for each estrogen and progesterone alone and in combination for the treatment of pre-menopausal, peri-menopausal, menopausal and post-menopausal females in relation to the treatment of estrogen- and progesterone-deficient states, each as herein defined below.

BACKGROUND

Hormone replacement therapy (HRT) is a medical treatment that involves the use of one or more of a group of medications designed to increase hormone levels in women who lack adequate hormone production. HRT can mitigate and prevent symptoms caused by diminished circulating estrogen and progesterone hormones regardless as to whether the subject is pre-menopausal, peri-menopausal, menopausal or post-menopausal. However, specific disease states can exist during each stage of menopausal progression.

HRT via transdermal delivery is presently available in various forms. One therapy involves administration of one or more estrogens. Another involves administration of a chemical analogue of naturally occurring progesterone, called a progestin. Progesterone administration acts, in addition to treating other disease states, to mitigate certain undesirable side effects from estrogen administration including, for example, endometrial hyperplasia (thickening), and reducing the incidence of endometrial cancer.

Reference to progesterone, both naturally-occurring and bio-identical, is generally collectively referred to herein as "progesterone."

Various references generally suggest the use of the progestogen class of hormones for inclusion in transdermal therapies, typically in combination with an estrogen. The teachings within such references are generally limited to progestins however. Progestins are sometimes confused in the literature with progesterone or progestogens generally. Yet progestins are a distinct subclass of progestogens; a synthetic progestogen that has progestational effects similar to progesterone. Typically, synthetic progestins have higher activity and are administered at significantly lower dosages relative to natural progesterone.

The term "progestogen(s)," as used herein, is inclusive of naturally-occurring and bio-identical progesterone and all synthetic progestins. The term "bio-identical" hormones, as used herein, refers to hormones which are identical in chemical structure to the hormones naturally produced by mammals, including humans, and can be used, and are often referred to as, natural hormone replacement therapy, or "NHRT."

Prevailing transdermal patch technologies utilize progestins over progesterone. This is due to, among others, the difficulty with solubilizing natural progesterone which is relatively insoluble, particularly at high dosages. Solubilized drug substances are preferred in the manufacture of the various patch technologies, particularly matrix and reservoir technologies. Synthetic progestins typically have greater potency and therefore lower dosage requirements. The reduced amount of progestin drug substance relative to a given volume of drug product generally affords relatively easier formulation solubility. For example, a drug load of 2.7 mg of norethethindrone acetate is provided within a 9 square cm round CombiPatch® product; a drug load of 4.8 mg of norethindrone acetate within the 16 square cm patch product.

Progesterone, on the other hand, is defined by a lower potency and therefore a higher dosage requirement. A much larger amount of progesterone drug substance is required, up to 200 mg, in a patch product. Given the higher dosage requirements and relative insolubility of progesterone, no transdermal patch employing a natural progesterone drug substance has been successfully commercialized.

Considering the current trend towards natural and bio-identical products, particularly with human hormones, the present disclosure provides, among other aspects, solubilized progesterone that can be used with transdermal patch technologies, and transdermal patches comprising progesterone, alone or in combination with at least one estrogen drug substance including, without limitation, estradiol, and other drug substances having estradiol or estradiol-like biological activity that are well known in the art.

Timing for HRT dosage administration is often varied cyclically, with estrogens taken daily and progesterone taken for approximately two weeks of every month; a method often referred to as "cyclic-sequential" or "sequentially-combined" HRT. This method is intended to mimic the natural menstrual cycle and typically causes menstruation similar to a period after the progesterone is stopped. This regime is most typically used in peri-menopausal or newly menopausal women as the alternative continuous method often resulting in irregular bleeding. An alternate method involving a constant dosage with both estrogen and progesterone delivered daily is called "continuous-combined" HRT. This method usually results in no menstruation and is used most often after a woman has been menopausal for some time.

With each of the cyclic-sequential or continuous combined methods, each of an estrogen and progesterone, as used herein, may be administered in the same or different dosage forms. When used in the same dosage form, the present disclosure includes each of an estrogen and progesterone in a transdermal patch. When administered in different dosage forms, the present disclosure provides for progesterone administered in a transdermal patch.

There is also a need for a pre-packaged cyclic-HRT with combination estrogen and progesterone. By way of example, doctors desiring to prescribe cyclic-HRT are required to prescribe two separate products, namely, an estrogen patch and a combination estrogen/progesterone patch or an estrogen patch along with another form of progesterone including oral or topical. Such separate dosing regimes often result in poor patient compliance due to, among others, confusion as to how and when to take each of the medications throughout the prescribed therapy period. Increased patient morbidity may result.

SUMMARY

According to various embodiments of the disclosure, hormone replacement therapies are provided comprising solubilized progesterone alone and optionally with an estrogen, cyclic/sequential and continuous-combined dosing regimes, and administered via transdermal HRT delivery systems. When solubilized progesterone is delivered alone via a transdermal patch, one or more estrogen compounds may be delivered concurrently on the same transdermal patch, or via any other known method of delivery.

A 28-day or monthly regime of transdermal patches can be packaged in a single package having delivery days identified to improve and optimize compliance. Various examples of such HRT transdermal delivery systems and uses thereof, each in accordance with the present invention, are set forth below.

BRIEF DESCRIPTION OF THE DRAWINGS

The accompanying drawings are included to provide a further understanding of the disclosure and are incorporated in and constitute a part of this specification, to illustrate embodiments of the disclosure and, together with the description, serve to explain the principles of the disclosure.

FIGS. 4, 5, 6, and 7 each illustrate a different sequence control device for a cyclic/sequential hormone replacement therapy regime in accordance with the present disclosure.

DETAILED DESCRIPTION OF THE ILLUSTRATED EMBODIMENTS

Definitions

Figure 1:
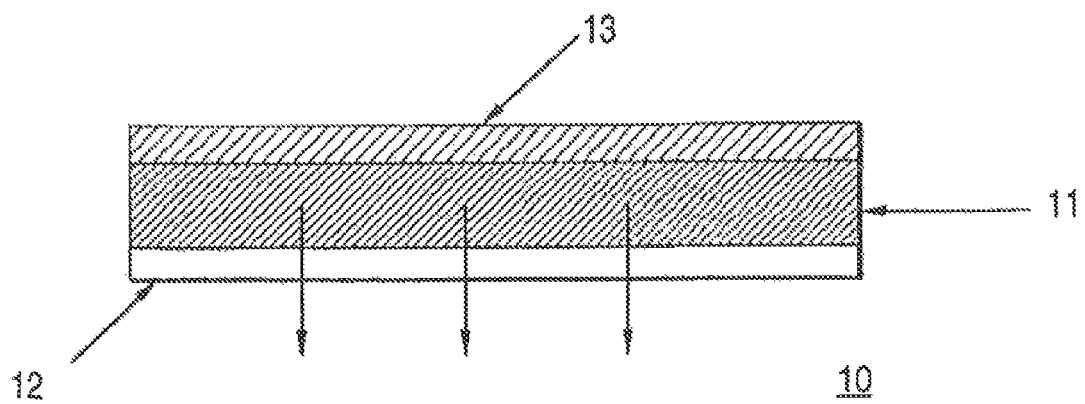
FIG. 1 illustrates a cross-sectional view of an embodiment of a transdermal patch in accordance with the present disclosure.

The term "excipients," as used herein, refers to non-active pharmaceutical ingredients such as carriers, solvents, oils, lubricants and others used in formulating pharmaceutical products. They are generally safe for administering to mammals, including humans, according to established governmental standards, including those promulgated by the United States Food and Drug Administration.

The term "medium chain," as used herein means any medium chain carbon-containing substance, including C4-C18, and including C6-C12 substances, fatty acid esters of glycerol, fatty acids, and mono-, di-, and tri-glycerides of such substances.

The term "micronized progesterone," as used herein, includes micronized progesterone having an X50 particle size value below about 15 microns and/or having an X90 particle size value below about 25 microns.

The term "micronized estradiol," as used herein, includes micronized estradiol having an X90 particle size value below about 7 microns.

Unless otherwise specified, "natural," as used herein with reference to certain hormones discussed herein, means bioidentical hormones prepared to match the chemical structure and effect of those that occur naturally in mammalian bodies, including humans (i.e., endogenous). An exemplary natural estrogen is estradiol (also described as 17 13-estradiol and E2) and a natural progestogen is progesterone.

The term "oil," as used herein may be any pharmaceutically acceptable substance, other than peanut oil, that would suspend and/or solubilize any suitable progestogen, including progesterone, starting material, or precursor, including micronized progesterone as described herein. More specifically, oils may include, for example and without limitation, medium chain fatty acids, generally of the group known as medium chain fatty acids consisting of at least one mono-, di-, and triglyceride, or derivatives thereof, or combinations thereof.

The term "pharmaceutically acceptable," indicates that the designated carrier, vehicle, diluent, excipient(s), and/or salts and other derivatives is generally chemically and/or physically compatible with the other ingredients comprising the formulation, and physiologically compatible with the recipient thereof. The term "solubilizer," as used herein, means any substance or mixture of substances that may be used to enhance the solubility of estrogen and progesterone, including, for example and without limitation, appropriate pharmaceutically acceptable excipients, such as solvents, co-solvents, surfactants, emulsifiers, oils and carriers.

The term "transdermal patch," as used herein, refers to any adhesive construct suitable to adhere to the skin of a mammal, and to deliver, among one or more drug substances, physiologically effective amounts of solubilized progesterone through the skin of a mammal, including, for example and without limitation, a human. The construct may be in the form of a flexible strip, comprising the desired amount of solubilized progesterone and one or more optional additional drug substances including estrogen.

As used herein, the term "treatment", or a derivative thereof, contemplates partial or complete inhibition of the disease state when a formulation as described herein is administered prophylactically or following the onset of the disease state for which such formulation is administered. For the purposes of the present disclosure, "prophylaxis," refers to administration of the drug substance(s) to a mammal, including human, to protect the mammal from any of the disorders set forth herein, as well as others.

The term "drug load," as used herein means the amount of drug substance in a given formulation as described herein.

The term "daily dose," as used herein means the nominal transdermal delivery rate (mg per day) of a drug substance; for example delivery of a drug substance via skin of average permeability.

The term "X50," as used herein, means that one-half of the particles in a sample are smaller in diameter than a given number. For example, micronized progesterone having an X50 of 15 microns means that, for a given sample of micronized progesterone, one-half of the particles have a diameter of less than 15 microns. Similarly, the term "X90" means that ninety percent (90%) of the particles in a sample are smaller in diameter than a given number.

Description

Provided herein are transdermal pharmaceutical formulations comprising solubilized progesterone and transdermal pharmaceutical formulations comprising solubilized progesterone and at least one estrogen compound. Generally, the transdermal patches are prepared by methods well known in the art, limited only by the drug load capacity of the respective technology.

For example, one common transdermal technology comprises a polymer matrix (or matrices) design wherein the polymer matrix can be prepared using natural polymers including, for example and without limitation, cellulose derivatives, zein, gelatin, shellac, waxes, proteins, gums and their derivatives, natural rubber, starch and the like; synthetic elastomers including, for example and without limitation, polybutadiene, polyisobutylene, hydrin rubber, polysiloxane and other silicone pressure sensitive adhesives available from Dow Corning (Elizabethtown, Ky.), silicone rubber, nitrile-containing compounds, acrylonitrile, butyl rubber, styrenebutadieine rubber, neoprene and the like; and/or synthetic homopolymers or copolymers including, for example and without limitation, polyvinyl alcohol, polyvinyl chloride, polyethylene, polypropylene, polyacrylate, polystyrene, polyamide, polyurea, polyvinylpyrrolidone, polymethylmethacrylate, epoxy, polyethylene/vinyl acetate, and the like. To this matrix is applied/incorporated at least one drug substance and, frequently, penetration enhancers, commonly used one or more solvents and/or one or more surfactants. An adhesive is used to affix the transdermal patch. Such adhesives can be affixed as a layer to the drug substance-containing matrix, or as one of the ingredients used to prepare the matrix. Other matrix technologies can include crystallization inhibitors and other pharmaceutically acceptable excipients. Matrix technology can also be developed into single or multi-layer patches. See, for example, U.S. Pat. Nos. 5,474,783, 5,958,446, and 6,440,454, and PCT Application Publication No. WO 97/43989, each of which are incorporated herein by reference.

Also well known in the transdermal pharmaceutical delivery art is a reservoir system, typically characterized by the inclusion of a reservoir: a compartment containing solubilized or suspended drug substance or substances, which is separate and distinct from the release liner. Various adhesive systems are also available for reservoir-type systems. Reservoir systems are frequently the system of choice when substantial drug loads are required. See, for example, U.S. Pat. Nos. 7,387,789, 5,656,286, 8,114,434, 6,024,976, and U.S. Patent Publication Nos.: 2012/0269878, and 2012/0283671, each of which are incorporated herein by reference.

Other transdermal patch technologies include, for example and without limitation, iontophoresis, electroporation, ultrasound/sonophoresis, and microscopic projection (e.g., microneedles) (see, e.g., Patel, D., et al., *The Pharma Innovation, Transdermal Drug Delivery System: A Review*, Vol. 1, No. 4, pg. 66-75 (2012)).

Such transdermal systems as described herein can be used for the preparation of solubilized progesterone transdermal patches, with or without the addition of at least one estrogen drug substance or other compatible drug substance(s).

Other aspects of the present disclosure includes the use of formulations as described herein, wherein a therapeutically effective amount of solubilized progesterone is at least one drug substance in said formulation for the treatment of a mammal, including humans: for endometrial hyperplasia; for secondary amenorrhea; as a method of treatment for preterm birth when said mammal has a shortened cervix; and other disease states or conditions treated with supplemental progesterone (collectively, "progesterone-deficient states"); and wherein an estrogen drug substance is optionally included in said formulations.

Additional aspects of the present disclosure include the use of formulations as described herein, wherein a therapeutically effective amount of solubilized progesterone and at least one solubilized estrogen drug substance, typically estradiol, are included in said formulations for the treatment of a mammal, including humans, having those disease states treated by the administration of progesterone and, menopause-related symptoms including, for example, vasomotor symptoms; in relation to treatment of hypoestrogenism related symptoms including, for example and without limitation, hot flashes and night sweats (vasomotor symptoms), sleep disturbances, mood changes and vulvo-vaginal atrophy; and osteoporosis and other non-menopausal disease states or conditions treated with supplemental estrogen (collectively, "estrogen-deficient states"). As such, the transdermal patches described herein that contain both progesterone and an estrogen drug substance can be used for the treatment of one or more progesterone-deficient states and one or more estrogen-deficient states.

For formulations described herein, each drug substance is administered to a mammal, including humans, in need of treatment.

An exemplary cyclic/sequential regime comprises daily delivery of from about 0.01 mg to about 2.0 mg of estradiol for 14-18 days, followed by daily delivery of from about 0.01 mg to about 2.0 mg of estradiol per day, and about 10 mg to about 200 mg of progesterone for 10-14 days. Cyclic/sequential regimes may be especially useful for menopausal females.

Other exemplary delivery dosages include one or more estrogen drug substances, typically estradiol (i.e., 17β-estradiol), for use in the formulations described herein include, without limitation, 0.01 mg, 0.025 mg, 0.05 mg, 0.0625 mg, 0.1 mg 0.125 mg, 0.25 mg, 0.375 mg, 0.50 mg, 0.625 mg, 0.75 .mg, 1.0 mg, 1.125 mg, 1.25 mg, 1.375 mg, 1.50 mg, 1.625 mg, 1.75 mg and 2.0 mg per day. In further embodiments, the daily delivery dosage estradiol is from about 0.01 mg to about 0.1 mg, from about 0.05 mg to about 0.5 mg, from about 0.1 mg to about 1.0 mg, from about 0.625 mg to about 2.0 mg, from about 0.5 mg to about 2.0 mg, from about 0.01 mg per day, and from about 0.05 mg per day.

Other exemplary delivery dosages of progesterone for use in the formulations described herein include, without limitation, 10 mg, 12.5 mg, 20 mg, 25 mg, 30 mg, 50 mg, 75 mg, 100 mg, 125 mg, 150 mg, 175 mg and 200 mg per day. In further embodiments, the daily delivery dosage of progesterone is from about 10 mg to about 100 mg, from about 20 mg to about 80 mg, from about 20 mg to about 30 mg, from about 20 mg to about 50 mg, from about 25 mg to about 75 mg, from about 100 mg to about 150 mg, from about 100 mg to about 125 mg, from about 125 mg to 150 mg, from about 10 mg, from about 20 mg, and from about 30 mg per day.

These dosage strengths for each of estradiol and progesterone can be administered in formulations described herein either alone or in combination. These dosage strengths, as used herein in transdermal delivery systems, are limited only by the drug load capacity of the respective technology. Estrogen drug substances other than estradiol may also be used in the present transdermal formulation, at the indicated label dose or as otherwise prescribed by physicians.

Accordingly, drug loads for the present transdermal pharmaceutical formulations can contain any amount necessary for partial-daily, daily, or multi-daily patches to provide the daily required doses, including the exemplary doses set forth herein.

Drug loads for patches of the present disclosure for solubilized progesterone include, for example and without limitation, about 10 mg, 12.5 mg, 20 mg, 25 mg, 30 mg, 50 mg, 75 mg, 100 mg, 125 mg, 150 mg, 175 mg and 200 mg, 250 mg, 300 mg, 350 mg, 400 mg, 450 mg, 500 mg, 550 mg, 600 mg, 650 mg, and 700 mg per patch. In further embodiments, the drug load of progesterone is not less than about 10 mg, 20 mg, 30 mg, 100 mg, 200 mg, 300 mg, 200 mg, 400 mg, and 600 mg per day.

In further embodiments, the drug load for one or more estrogen drug substances, typically estradiol (i.e., 17β-estradiol), include, for example and without limitation, about 0.01 mg, 0.025 mg, 0.05 mg, 0.0625 mg, 0.1 mg 0.125 mg, 0.25 mg, 0.375 mg, 0.50 mg, 0.625 mg, 0.75 .mg, 1.0 mg, 1.125 mg, 1.25 mg, 1.375 mg, 1.50 mg, 1.625 mg, 1.75 mg and 2.0 mg. In further embodiments the drug load for one or more estrogen drug substance is from about 0.01 mg to about 0.1 mg, from about 0.05 mg to about 0.5 mg, from about 0.1 mg to about 1.0 mg, from about 0.625 mg to about 2.0 mg, from about 0.5 mg to about 2.0 mg, from about 0.5 mg to 0.6 mg, from about 0.01 mg, and from about 0.05 mg per day.

Progesterone formulations of the present disclosure are prepared by solubilizing progesterone drug substance via blending with a pharmaceutically acceptable oil; generally, the oil comprises at least one medium chain fatty acid such as medium chain fatty acids consisting of at least one mono-, di-, or triglyceride, or derivatives thereof, or combinations thereof. Sufficient oil is used to form a solubilized progesterone. Optionally added are other excipients including, for example and without limitation, anti-oxidants, permeability enhancers, crystallization inhibitors and the like.

In another embodiment, a patch in accordance with the present disclosure is administered every three to four days in postmenopausal women, and may produce the following target absorption profile for estradiol and progesterone. For estradiol, a target steady-state serum concentration of about 30 to 60 pg/mL may be achieved. In another embodiment a target average steady-state serum concentration of about 45 to 50 pg/mL may be achieved, which is equivalent to the normal ranges observed at the early follicular phase in premenopausal women. These concentrations may be achieved within 12 to 24 hours following patch delivery. The patch may be configured so that minimal fluctuation in serum estradiol concentrations is achieved following patch application, which indicates a consistent hormone delivery over the application interval. For progesterone, a target average steady-state serum concentration may be achieved within 12 to 24 hours following patch delivery system.

In other aspects and embodiments, progesterone is fully solubilized using, for example and without limitation, sufficient amounts of: Transcutol and Miglyol; Transcutol, Miglyol and Capmul PG 8 and/or PG 10; Campul MCM; Capmul MCM and a non-ionic surfactant; and Campul MCM and Gelucire.

Various ratios of these oils can be used for full solubilization of progesterone. Capmul MCM and a non-ionic surfactant can be used at ratios including, for example and without limitation: 65:35, 70:30, 75:25, 80:20, 85:15 and 90:10. Campul MCM and Gelucire can be used at ratios including, for example and without limitation, 6:4, 7:3, 8:2, and 9:1. Among other combinations, these oils and/or solubilizers, as defined herein, and combinations thereof, can be used to form combination estradiol and progesterone formulations of the present disclosure. In accordance with various embodiments, formulations do not include peanut oil. The lack of peanut oil obviates the risk posed to those having peanut-based allergies.

Pharmaceutically acceptable oils include, without limitation, the use of at least one of a caproic fatty acid; a caprylic fatty acid; a capric fatty acid; a tauric acid; a myristic acid; a linoleic acid; a succinic acid; a glycerin; mono-, di-, or triglycerides and combinations and derivatives thereof; a polyethylene glycol; a polyethylene glycol glyceride (Gelucire®; GATTEFOSSE SAS, Saint-Priest, France); a propylene glycol; a caprylic/capric triglyceride (Miglyol®; SASOL Germany GMBH, Hamburg; Miglyol includes Miglyol 810, 812, 816 and 829); a caproic/caprylic/capric/lauric triglyceride; a caprylic/capric/linoleic triglyceride; a caprylic/capric/succinic triglyceride; a propylene glycol monocaprylate; propylene glycol monocaprate; (Capmul® PG-8 and 10; the Capmul brands are owned by ABITEC (Columbus Ohio); a propylene glycol dicaprylate; a propylene glycol dicaprate; medium chain mono- and di-glycerides (Capmul MCM); a diethylene glycol mono ester (including 2-(2-ethoxyethoxy) ethanol: Transcutol); a diethylene glycol monoethyl ether; esters of saturated coconut and palm kernel oil and derivatives thereof; triglycerides of fractionated vegetable fatty acids, and combinations and derivatives thereof.

Progesterone and estrogen, in particular estradiol, may be micronized to facilitate solubilization. Progesterone and estrogen may be micronized by any one of the multiple methods typically utilized by one skilled in the art. In various embodiments, micronized progesterone has an X50 particle size value of less than about 15 microns, less than about 10 microns, less than about 5 microns and/or less than about 3 microns. In various embodiments, micronized progesterone has an X90 particle size value of less than about 25 microns, less than about 20 microns, and/or less than about 15 microns. In various embodiments, micronized estradiol has an X90 particle size value of less than about 10 microns, less than about 8 microns, and/or less than about 7 microns.

Particle size may be determined in any suitable manner. For example, a Beckman Coulter LS 13 320 Laser Diffraction Particle Size Analyzer (the "Beckman Device") may be used to determine particle size. As described above, particle size may be represented by various metrics, for example, through an X50 particle size, and/or X90 particle size, or any similar descriptions of particle size.

In various embodiments, at least one estrogen drug substance, typically estradiol, is solubilized and then combined with solubilized progesterone, or may be co-solubilized with progesterone as taught herein.

In various embodiments, the solubilizing agent for an estrogen drug substance, typically estradiol, is selected from at least one of a solvent or co-solvent. Suitable solvents and co-solvents include any mono-, di- or triglyceride and glycols, and combinations thereof. More specifically, other solubilizers include, for example and without limitation, glyceryl mono- and di-caprylates, propylene glycol and 1,2,3-propanetriol (glycerol, glycerin, glycerine).

Anionic and/or non-ionic surfactants can be used in other embodiments of the presently disclosed formulations containing solubilized progesterone or a combination of such progesterone and at least one solubilized estrogen drug substance. In certain embodiments, a non-ionic surfactant is used. Exemplary non-ionic surfactants may include, for example and without limitation, one or more of oleic acid, linoleic acid, palmitic acid, and stearic acid. In further embodiments, the non-ionic surfactant may comprise polyethylene sorbitol esters, including polysorbate 80, which is commercially available under the trademark TWEEN 80® (Sigma Aldrich, St. Louis, Mo.). Polysorbate 80 comprises approximately 60%-70% oleic acid with the remainder comprising primarily linoleic acids, palmitic acids, and stearic acids. Polysorbate 80 may be used in amounts ranging from about 5 to 50%, and in certain embodiments, about 30% of the formulation total mass.

In various other embodiments, the non-ionic surfactant is selected from one or more of glycerol and polyethylene glycol esters of long chain fatty acids, for example, lauroyl macrogol-32 glycerides and/or lauroyl polyoxyl-32 glycerides, commercially available as Gelucire, including, for example, Gelucire 39/01, 43/01, 44/11 and 50/13. These surfactants may be used at concentrations greater than about 0.01%, and, in some embodiments in amounts of about 0.01%-10.0%, 10.1%-20%, and 20.1%-30% may be used.

Other exemplary non-ionic surfactants include PEG-6 palmitostearate and ethylene glycol palmitostearate, which is available commercially as TEFOSE 63® ("Tefose 63") (GATTEFOSSE SAS, Saint-Priest, France) which can be used with, for example, Capmul MCM having ratios of MCM to Tefose 63 of, for example, 8:2 and 9:1. Additional examples of solubilizing agents with non-ionic surfactants include, for example, Miglyol:Gelucire 50/13 and Miglyol: Tefose 63.

Anionic surfactants are well known and can include, for example and without limitation: ammonium lauryl sulfate, dioctyl sodium sulfosuccinate, perfluoro-octane sulfonic acid, potassium lauryl sulfate and sodium stearate.

As such, non-ionic and/or anionic surfactants can be used alone or with at least one solubilizing agent or can be used in combination with other surfactants. Accordingly, such surfactants, or any other excipient as set forth herein, should be used to provide a solubilized progesterone drug substance; to provide a solubilized estrogen drug substance; or optionally a solubilized progesterone drug substance with at least one estrogen drug substance; upon release from a transdermal patch of the present disclosure, with consistency of dissolution and/or delivery of the solubilized progesterone drug substance and solubilized estrogen drug substance, or optionally a solubilized progesterone drug substance with estrogen drug substance, that promotes transdermal absorption.

In additional embodiments, an antioxidant is used. Any suitable anti-oxidant may be used such as, for example and without limitation butylated hydroxytoluene.

Permeability enhancers are chemical substances that increase the flux of a drug substance through the skin. These substances may include, for example, various glycols such as dipropylene or propylene glycol, oils such as olive oil, squalene or lanolin, long chain ethers and esters, urea and various urea derivatives, solvents such as dimethylsulfoxide (DMSO) and dimethylformamide (DMF), salicylic acid, various amino acids, Vitamin-C, Vitamin-A, and Vitamin-E, and the like.

As is with all oils, solubilizers, excipients, antioxidants, permeability enhancers, crystallization inhibitors and any other additives used in intermediate formulations (e.g., during production during solublization) and during production of the resulting transdermal drug products described herein, each is to pharmaceutically acceptable.

The embodiments herein provide for the preparation and use of a solubilized progesterone transdermal patch. Such patch can be used by itself or as concomitant administration with an estrogen drug substance which can be administered via various dosage forms and via various routes of administration. Such patches can also co-administer solubilized progesterone and at least one solubilized estrogen drug substance.

Transdermal patches according to the present disclosure will vary by patch surface area, as dependent upon the dosage concentration required over the desired time for release, the actual release mechanism, and shape. Transdermal patch surface area can range, for example and without limitation, from less than about 10 $cm^2$ to greater than about 100 $cm^2$. For example, a transdermal patch may be from about 2.0, 2.5 $cm^2$, 3.0 $cm^2$, 3.5 $cm^2$, 4.0 $cm^2$, 4.5 $cm^2$, 5.0 $cm^2$, 5.5 $cm^2$, 6.0 $cm^2$, 6.5 $cm^2$, 7.0 $cm^2$, 7.5 $cm^2$, 8.0 $cm^2$, 8.5 $cm^2$, 9.0 $cm^2$, 9.5 $cm^2$, or about 10 $cm^2$. In various embodiments, a patch may be from about 9 $cm^2$ to about 16 $cm^2$ in surface area.

The transdermal patches of the present disclosure can include any conventional form such as, for example, adhesive matrix, polymeric matrix, reservoir patch, matrix or monolithic-type laminated structure, or other release-rate modifying mechanisms known in the art, and are generally comprised of one or more backing layers, adhesives, permeation enhancers, an optional rate controlling membrane and a release liner which is removed to expose the adhesives prior to application. Polymeric matrix patches also comprise a polymeric-matrix forming material.

Various delivery systems can be used to administer the formulations of the present disclosure, including, for example, encapsulation in liposomes, microbubbles, emulsions, microparticles, microcapsules, nanoparticles, microneedles and the like.

According to additional embodiments described herein, a 28-day or monthly regime of transdermal patches can be packaged in a single kit having administration days identified to improve compliance and reduce associated symptoms, among others. One or more of the transdermal patches may contain no estradiol, for example, and/or no progesterone. Transdermal patches that comprise no estrogen or progesterone drug substance may be referred to as placebos.

Transdermally administered formulations of the present disclosure containing solubilized progesterone are used for the treatment of endometrial hyperplasia, secondary amenorrhea and other disease states treated with supplemental progesterone. Generally, progesterone-containing formulations described herein are used to treat the effects of the administration of supplemental estrogen whether administered alone or in combination with solubilized estradiol of the present disclosure or other estrogen-containing formulations.

Transdermally administered formulations of the present disclosure containing solubilized estradiol are used to treat estrogen-deficient states, including vasomotor symptoms, for example, in relation to treatment of hypoestrogenism related symptoms including, for example and without limitation, hot flashes and night sweats (vasomotor symptoms), sleep disturbances, mood changes, vulvo-vaginal atrophy, and osteoporosis and other non-menopausal disease states treated with supplemental estrogen.

Various objects of the disclosure is to provide increased patient compliance secondary to ease of use in a single product kit having both progesterone and estradiol, and to reduce the metabolic and vascular side effects of the commonly used synthetic progestins in combination HRT (norethindrone acetate, medroxyprogesterone acetate, etc.) including, for example, stroke, heart attacks, blood clots and breast cancer.

FIG. 1 illustrates the cross section of a patch 10 comprising a backing layer 13, an adhesive matrix containing active hormone(s) 11, and a removal release layer 12. The arrows in FIG. 1 indicate the direction of migration of drug substance(s).

Figure 2:
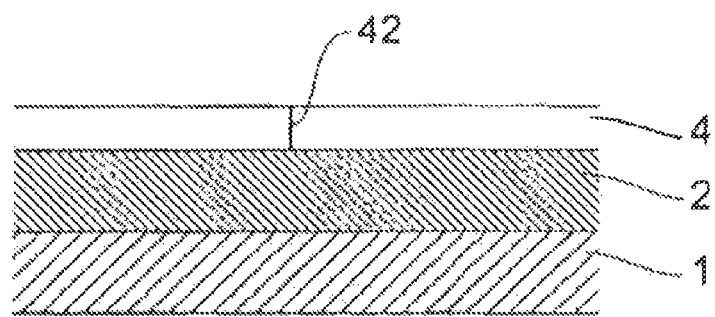
FIG. 2 illustrates a cross-sectional view of another embodiment of a transdermal patch in accordance with the present disclosure.

FIG. 2 illustrates another embodiment of a patch comprising a release layer 4 breakable across perforation or slit 42, and active adhesive layers 1 and 2.

Figure 3:
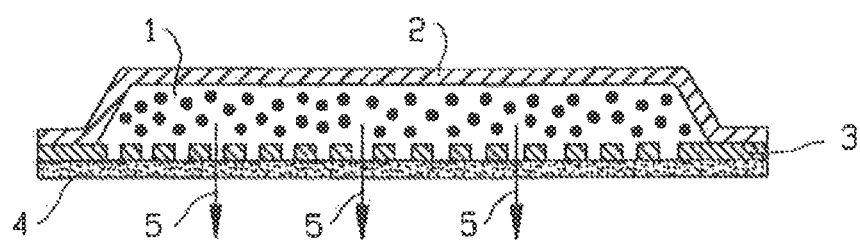
FIG. 3 illustrates a cross-sectional view of an embodiment of a transdermal reservoir in accordance with the present disclosure.

FIG. 3 illustrates the cross-sectional view of an embodiment of a liquid reservoir-type transdermal delivery device. The device comprises housing 2, a porous layer 3, a removable sealing film 4, and a liquid composition 1 containing the active hormone(s). The arrows 5 in FIG. 3 illustrate the direction of migration of the drug substance(s).

In various embodiments, systems can be worn for a one-week duration while others can be worn for a 3-4 day duration (e.g., approximately 2 systems per week). Still others can be configured to be worn for other durations of time that can be shorter than 3-4 days (e.g. 1 day), or longer than one week (e.g., 2-4 weeks).

According to various embodiments, a plurality of transdermal systems can be packaged together, whether cyclic/sequential or continuous-combined. The package may comprise a packaging system further configured to guide the application of the transdermal systems throughout the intended cycle; such as throughout the application days and/or weeks within an intended dosing cycle ("sequence control device"). Such sequence control devices offer improved patient compliance and reduce associated symptoms, among other advantages. By way of example, according to various embodiments, a 28-day or monthly regime of transdermal systems can be packaged in a sequence control device having application days and/or weeks identified. According to other embodiments, a 28-day or monthly regime of transdermal systems can be packaged in a plurality of sequence control devices, for example, 2 or 4.

Various sequence control devices may be used with transdermal systems to construct kits. Exemplary sequence control devices comprise a plurality of storage elements, wherein each storage element corresponds to one or more days and wherein each storage element encloses one or more transdermal systems therein for application during the corresponding days (e.g., on the first day of the corresponding days). A storage element may comprise a blister, a laminate, or another air-tight configuration, for enclosing one or more transdermal systems therein.

Exemplary sequence control devices can optionally also comprise a plurality of spacer elements arranged between storage elements, wherein each spacer element corresponds to one or more days during which no new application of a transdermal system is prescribed. A spacer element may correspond to a placebo transdermal system or the absence of any transdermal system. Spacer elements may be especially useful for embodiments wherein one storage element corresponds to one day, and the enclosed transdermal system(s) is/are configured to be worn for more than one day.

Exemplary sequence control devices can comprise storage elements, (and optional spacer elements) sequentially coupled to a common substrate and arranged thereon to be adjacent in rows and/or columns.

Additionally, or alternatively, exemplary sequence control devices can comprise storage elements (and optional spacer elements) sequentially stacked. The sequence of such stacked elements can be maintained in various ways, for example, each of the stacked elements being coupled at one of its edges to a common substrate, or the stacked elements being contained within a container having a dispensing edge configured to only be opened large enough to dispense a single storage or spacer element at a time. In such embodiments, the stacked elements are biased toward the dispensing edge, for example, mechanically or simply under the influence of gravity if the dispensing edge is situated at the bottom of the sequence control device.

For example, FIG. 4 illustrates a 28-day cyclic/sequential estrogen ("E") progesterone ("P") regime of transdermal systems packaged in a sequence control device, wherein storage elements are sequentially arranged on a common substrate to be variously adjacent in rows and columns. The substrate can comprise a plurality of scores, perforations or dividers between adjacent elements. In this embodiment, the transdermal systems are configured to be worn for 3-4 day duration and each storage element corresponds to 3-4 days as applicable.

Similar to FIG. 4, FIG. 5 illustrates another 28-day cyclic/sequential estrogen ("E") progesterone ("P") regime of transdermal systems packaged in a sequence control device, wherein storage and spacer elements are sequentially arranged on a common substrate to be variously adjacent in rows and columns. As above, the substrate can comprise a plurality of scores, perforations or dividers between adjacent elements. In this embodiment, the transdermal systems are configured to be worn for 3-4 day duration and each storage element corresponds to one day.

Figure 6:
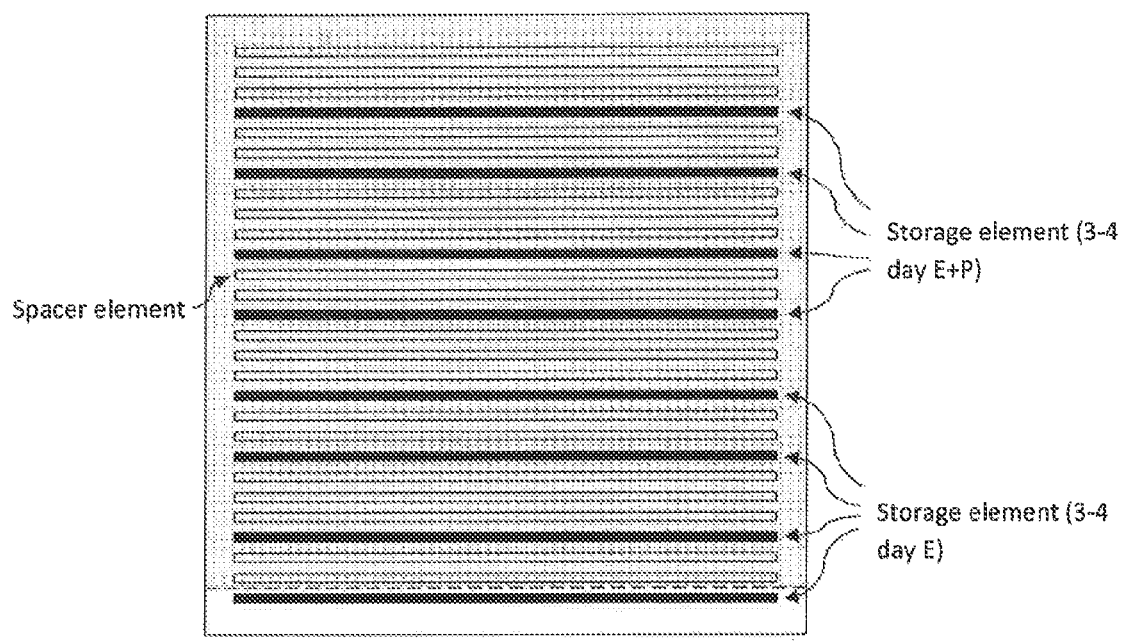

FIG. 6 illustrates another embodiment of a 28-day cyclic/sequential estrogen ("E") progesterone ("P") regime of transdermal systems packaged in a sequence control device, wherein storage and spacer elements are sequentially stacked, the stacked elements being contained within a container having a dispensing edge configured to only be opened at the bottom large enough to dispense a single storage or spacer element at a time. In this embodiment, the stacked elements are biased toward the dispensing edge under the influence of gravity. As above, in this embodiment, the transdermal systems are configured to be worn for 3-4 day duration and each storage element corresponds to one day.

Figure 7:
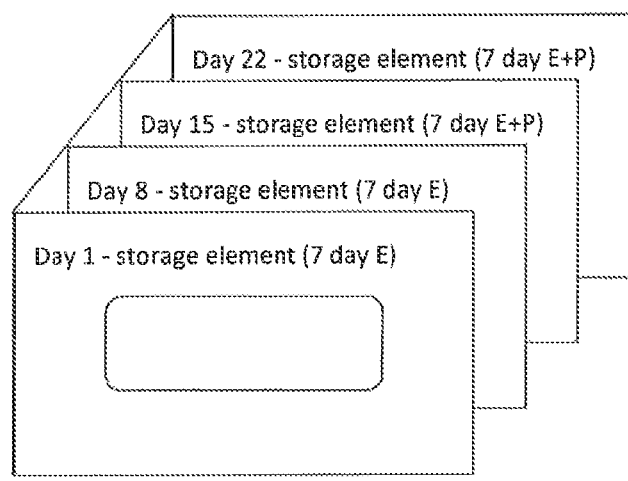

FIG. 7 illustrates another embodiment of a 28-day cyclic/sequential estrogen ("E") progesterone ("P") regime of transdermal systems packaged in a sequence control device, wherein storage elements are sequentially stacked, each of the stacked elements being coupled at one of its edges to a common substrate. In this embodiment, the transdermal systems are configured to be worn for a one-week duration and each storage element corresponds to one day.

EXAMPLES

The following examples illustrate formulations of solubilized progesterone and estradiol, compositions of adhesive, liquid matrix compositions, and reservoir technologies, that incorporate solubilized progesterone and estradiol, for transdermal HRT, particularly NHRT. The examples illustrate target loading of adhesive compositions onto release layers of various size for the preparation of transdermal patches. The examples further illustrate exemplary loading of liquid compositions of solubilized progesterone, optionally including estradiol, into reservoirs usable for liquid transdermal delivery systems. The flux of progesterone and estradiol through the skin delivered from any of the matrices described herein can be in a variety of ranges; in one embodiment in a range of from about 0.1 to about 20 µg/cm$^2$/hr. The flux depends on the type of matrix, i.e. adhesive or liquid compositions, the non-active ingredients, the inclusion of permeation enhancers, release-rate modifying mechanisms, crystallization inhibitors and the physiology of the mammal, typically human, subject.

Example 1

Solubilized Progesterone Master Batches with Optional Estradiol

TABLE A illustrates exemplary solubilized progesterone formulations. Exemplary formulas are prepared by heating various solubilizers and then adding micronized progesterone and optionally estradiol to the heated mixture. For example, Campul MCM is heated to between 30° C. to 50° C., more preferably from 35° C. to 45° C., and more preferably to 40° C.+/−2° C. Gelucire 44/14 is added to the Campul MCM and mixed until dissolved. The addition is performed all at once or may be divided in portions over a period of time. Heat is continuously applied during the mixing of the requisite solubilizers. Heating and mixing are performed under an inert or relatively inert gas atmosphere. In this example, nitrogen gas ($N^2$) is used. Mixing and/or heating is performed in any suitable vessel, such as a stainless steel vessel equipped with any suitable submerged mixer and optionally a vacuum may or may not be applied.

TABLE A

Solubilized Progesterone and Estradiol Formulations

| Ingredient (% w/w) | 1 | 2 | 3 |
|---|---|---|---|
| Progesterone, USP, micronized | 7.14 | 7.34 | 9.50 |
| 17β-Estradiol hemihydrate, USP | 0.29 | 1.2 | 1.2 |
| Monoglycerides/diglycerides/triglycerides of caprylic and capric acid (e.g. Capmul ® MCM, NF) | 82.57 | 91.46 | — |
| Lauroyl polyoxy-32-glycerides (e.g. Gelucire ® 44/14, NF) | 10.0 | — | — |
| Propylene glycol monocaprylate (e.g. Capmul ® PG8) | — | — | 89.30 |
| Total | 100 | 100 | 100 |

Example 2

Patch Adhesive Delivery Matrices

TABLE B illustrates adhesive matrices that are prepared by mixing appropriate polymers and then slowly mixing in the solubilized progesterone formulae from TABLE A. Volatile solvents, such as silicone fluids, low molecular weight alcohols, glycols or ethers, are added to adjust the viscosity of the adhesive composition and the tackiness of the dried adhesive. Any additional drug substance, such as estradiol, is be added to the mixture. The resulting adhesive mixture containing the drug substances are used to produce various transdermal products.

Out of the suitable polymers, the preferred polymers for a pressure sensitive adhesive (PSA) matrix, with solubilized estradiol and progesterone, include polysiloxane PSAs from Dow Corning Corporation (Midland, Mich.), polyacrylate, polyisobutylene, polyvinylpyrrolidone, and polyethylene/vinyl acetate co-polymer. A suitable adhesive matrix is formed from a medical silicone PSA without the need for additional polymers.

TABLE B

Adhesive Matrices

| Ingredient (% w/w) | 1 | 2 | 3 |
|---|---|---|---|
| Solubilized progesterone/estradiol (formula # from Table A) | 50(1) | 75(2) | 75(3) |
| Polyacrylate | 0-30 | 0-30 | 0-30 |
| Polysiloxane | 20-70 | 20-70 | 20-70 |
| Polyisobutylene | 0-45 | 0-45 | 0-45 |
| Polyvinylpyrrolidone | 0-20 | 0-20 | 0-20 |
| Polyethylene/vinyl acetate co-polymer | 0-40 | 0-40 | 0-40 |
| Volatile solvent (e.g. silicone fluid) | q.s. | q.s. | q.s. |
| Total | 100 | 100 | 100 |

TABLE B-continued

Adhesive Matrices

| Ingredient (% w/w) | 1 | 2 | 3 |
|---|---|---|---|
| % w/w progesterone in delivery matrix | 3.57 | 5.505 | 7.125 |
| % w/w estradiol in delivery matrix | 0.145 | 0.900 | 0.900 |

It is noted that compositions of TABLE A will have estradiol previously added, so no additional estradiol is added into the adhesive matrix above.

Example 3

Transdermal Patches

TABLE C illustrates transdermal delivery systems based on adhesive matrices exemplified in TABLE B. To prepare these exemplary transdermal patches, an exemplary composition from TABLE B is applied onto a release liner. The resulting product is dried if necessary to remove any volatiles. Lastly, a suitable backing material is applied such that the adhesive matrix is sandwiched between a release liner and a backing material. Suitable release liners are available from Dow Chemical Co. (Plaquemine, La.) and 3M (St. Paul, Minn.). Suitable backing material may comprise plastic films of polyethylene/, vinyl acetate resins, ethylene/vinyl acetate copolymers, polyvinyl chloride, polyurethane, and the like, or metal foils, nonwoven fabric, cloth, and various laminated films.

Resulting patch systems deliver progesterone alone, a combination of progesterone and estradiol, or estradiol alone.

TABLE C

Transdermal Patches

| Matrix Dimensions | | Matrix (from TABLE B) | Matrix weight per patch (mg) | Theoretical drug substance(s) per patch (mg) | |
|---|---|---|---|---|---|
| Area (cm²) | Thickness (mm) | | | Progesterone | Estradiol |
| 2.5 | 1 | Matrix 1 | 250 | 8.925 | 0.3625 |
| 2.5 | 2 | Matrix 3 | 500 | 35.625 | 4.50 |
| 5 | 1 | Matrix 1 | 500 | 17.85 | 0.725 |
| 5 | 2 | Matrix 2 | 1000 | 55.05 | 9.00 |
| 7 | 1 | Matrix 2 | 700 | 38.535 | 6.3 |
| 10 | 1 | Matrix 3 | 1000 | 71.25 | 9.00 |
| 16 | 1 | Matrix 3 | 1600 | 114.00 | 14.40 |

Example 4

Liquid Transdermal Delivery Matrix

TABLE D illustrates exemplary compositions usable in liquid transdermal reservoirs. The exemplified compositions incorporate the solubilized progesterone and estradiol formulations of TABLE A as indicated. One or more saccharides are used, such as methyl cellulose, ethyl cellulose, carboxymethylcellulose, carboxymethylethylcellulose, starch, carrageenan, and pectin. The compositions further include gums such as xanthan or guar, low molecular weight glycols, and preservatives.

The examples of TABLE D can be incorporated in delivery systems such as the embodiment generalized in FIG. 3.

TABLE D

Liquid Reservoir Compositions

| Ingredient (% w/w) | 1 | 2 | 3 |
|---|---|---|---|
| Solubilized progesterone/estradiol (formula # from Table A) | 50(1) | 50(2) | 50(3) |
| Saccharide (e.g. methyl cellulose, etc.) | 20-80 | 20-80 | 20-80 |
| Propylene glycol | 0-20 | 0-20 | 0-20 |
| Water | q.s. | q.s. | q.s. |
| Total | 100 | 100 | 100 |
| % w/w progesterone in liquid composition | 3.57 | 3.67 | 4.75 |
| % w/w estradiol in liquid composition | 0.145 | 0.60 | 0.60 |

Example 5

Particle Size Analysis

A particle size analysis for micronized estradiol was conducted by using a Beckman Coulter LS 13 320 Laser Diffraction Particle Size Analyzer (the "Beckman Device"). The Beckman Device uses laser diffraction and polarization intensity differential scattering (PIDS) technology to determine the particle size distribution of materials with an overall sizing range of 0.04 µm to 2000 µm in a single scan with no extrapolation. The analysis yields that a sample has an X50 value of 2.652 microns and an X90 value of 6.031 microns.

Approximately 0.01 g of a sample was dispersed with Coulter 1B dispersant then diluted with about 10 ml of deionized water. The sample dilution was then sonicated for 15 seconds and added to the Beckman Device to analyze for 90 seconds. The particle size distribution was determined using the Fraunhofer optical model.

Example 6

Particle Size Analysis

A particle size analysis for micronized progesterone was conducted also using the Beckman Device. A sample was prepared and analyzed. The Beckman Device particle sensor yields that the sample has an X50 of 6.67 micron, an X75 of 14.78 microns, and an X25 of 2.193 microns.

It will be apparent to those skilled in the art that various modifications and variations can be made to the present disclosure without departing from the spirit or scope of the disclosure. Thus, it is intended that the present disclosure covers the modifications and variations of this disclosure provided they fall within the scope of the appended claims and their equivalents.

Likewise, numerous characteristics and advantages have been set forth in the preceding description, including various alternatives together with details of the structure and function of the formulations, devices and/or methods. The disclosure is intended as illustrative only and as such is not intended to be exhaustive. It will be evident to those skilled in the art that various modifications may be made, especially in matters of structure, materials, elements, components, shape, size and arrangement of parts including combinations within the principles of the disclosure, to the full extent indicated by the broad, general meaning of the terms in which the appended claims are expressed. To the extent that these various modifications do not depart from the spirit and scope of the appended claims, they are intended to be encompassed therein.

We claim:

1. A transdermal pharmaceutical formulation comprising progesterone and a solubilizing agent, wherein the solubilizing agent comprises an oil containing a C6-C12 fatty acid, wherein the progesterone is solubilized in the solubilizing agent and wherein the solubilized progesterone is present in a transdermal patch.

2. The transdermal pharmaceutical formulation of claim 1, wherein the oil is a monoglyceride, a diglyceride, or a triglyceride containing a C6—C12 fatty acid, and combinations thereof.

3. The transdermal pharmaceutical formulation of claim 1, wherein the solubilizing agent is selected from the group consisting of Transcutol and Miglyol; Transcutol, Miglyol and Capmul PG8; Transcutol, Miglyol and Capmul PG10; Campul MCM; and Capmul MCM and Gelucire.

4. The transdermal pharmaceutical formulation of claim 1, wherein the solubilizing agent is Capmul MCM and a non-ionic surfactant.

5. The transdermal pharmaceutical formulation of claim 4, wherein the solubilizing agent is Capmul MCM and Gelucire.

6. The transdermal pharmaceutical formulation of claim 1, wherein the daily dose of progesterone is from about 10 mg to about 100 mg per patch.

7. The transdermal pharmaceutical formulation of claim 1, wherein the daily dose of progesterone is from about 20 mg to about 80 mg per patch.

8. The transdermal pharmaceutical formulation of claim 1, wherein the daily dose of progesterone is from about 20 mg to about 30 mg per patch.

9. The transdermal pharmaceutical formulation of claim 1, wherein the transdermal patch is from about 9 $cm^2$ to about 16 $cm^2$ in surface area.

10. The transdermal pharmaceutical formulation of claim 1, further comprising 17β-estradiol.

11. The transdermal pharmaceutical formulation of claims 10, wherein the 17β-estradiol is solubilized.

12. The transdermal pharmaceutical formulation of claim 10, wherein the daily dose of 17β-estradiol is from about 0.01 mg to about 0.1 mg per patch.

13. A method of treating at least one progesterone-deficient state in a mammal in need of treatment comprising administering an effective amount of a transdermal pharmaceutical formulation of claim 1.

14. A method of treating at least one progesterone-deficient state and at least one estrogen-deficient state in a mammal in need of treatment comprising administering an effective amount of a transdermal pharmaceutical formulation of claim 10.

15. The method of claim 14, wherein the progesterone and the 17β-estradiol drug substance are administered in a cyclic-sequential method.

16. The method of claim 14, wherein the progesterone and the 17β-estradiol drug substance are administered in a continuous-combined method.

17. A method of treating at least one progesterone-deficient state and at least one estrogen-deficient state in a mammal in need of treatment comprising administering an effective amount of a transdermal pharmaceutical formulation of claim 1, and an effective amount of at least one estrogen drug substance wherein the estrogen drug substance is administered via a method independent of the administration of progesterone in the transdermal pharmaceutical formulation.

18. The method of claim 17, wherein the progesterone and the estrogen drug substance are administered in a cyclic-sequential method.

19. The method of claim 17, wherein the progesterone and the estrogen drug substance are administered in a continuous combined method.

20. The method of claim 17, wherein the estrogen drug substance is estradiol administered via oral administration.

* * * * *